US009968671B2

(12) United States Patent
Sellers

(10) Patent No.: US 9,968,671 B2
(45) Date of Patent: May 15, 2018

(54) AVIAN REOVIRUS VACCINES

(71) Applicant: UNIVERSITY OF GEORGIA RESEARCH FOUNDATION, INC., Athens, GA (US)

(72) Inventor: Holly S. Sellers, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days. days.

(21) Appl. No.: 15/223,623

(22) Filed: Jul. 29, 2016

(65) Prior Publication Data

US 2017/0028055 A1 Feb. 2, 2017

Related U.S. Application Data

(63) Continuation-in-part of application No. PCT/US2015/013449, filed on Jan. 29, 2015.

(60) Provisional application No. 61/932,995, filed on Jan. 29, 2014.

(51) Int. Cl.
| | |
|---|---|
| *C07K 14/14* | (2006.01) |
| *A61K 39/15* | (2006.01) |
| *C12N 7/00* | (2006.01) |
| *A61K 39/12* | (2006.01) |
| *C07K 14/005* | (2006.01) |
| *C07K 16/10* | (2006.01) |
| *G01N 33/569* | (2006.01) |
| *A61K 39/00* | (2006.01) |

(52) U.S. Cl.
CPC .............. *A61K 39/15* (2013.01); *A61K 39/12* (2013.01); *C07K 14/005* (2013.01); *C07K 16/10* (2013.01); *C12N 7/00* (2013.01); *G01N 33/56983* (2013.01); *A61K 2039/552* (2013.01); *C12N 2720/12221* (2013.01); *C12N 2720/12222* (2013.01); *C12N 2720/12234* (2013.01); *C12N 2720/12264* (2013.01); *G01N 2333/14* (2013.01); *G01N 2469/00* (2013.01)

(58) Field of Classification Search
None
See application file for complete search history.

(56) References Cited

U.S. PATENT DOCUMENTS 6,951,650 B1 * 10/2005 van Loon .............. A61K 39/15 424/215.1

FOREIGN PATENT DOCUMENTS

| | | | |
|---|---|---|---|
| WO | WO 99/24582 A1 | | 5/1999 |
| WO | WO1999/24582 | * | 5/1999 |
| WO | WO 2009/093251 A2 | | 7/2009 |
| WO | WO 2009/093251 A3 | | 7/2009 |
| WO | WO 2015/116778 A1 | | 8/2015 |

OTHER PUBLICATIONS

GenBank: AJP74921.1. Sigma C, partial [Avian orthoreovirus]. Dated Dec. 31, 2015. (Year: 2015).*
Drastini et al. Chymotrypsin and Trypsin Sensitivities of Avian Reoviruses. Can J Vet Res 1994; 58: 75-78. (Year: 1994).*
EP Patent Application No. 15743978.7, filed Jan. 29, 2015; Supplementary European Search Report dated Aug. 11, 2017; 8 pages.

Goldenberg et al., "Genetic and antigenic characterization of sigma C protein from avian reovirus" *Avian Pathology*, Jun. 11, 2010; 39(3):189-99.

Shmulevitz et al., "Sequential Partially Overlapping Gene Arrangement in the Tricistronic S1 Genome Segments of Avian Reovirus and Nelson Bay Reovirus: Implications for Translation Initiation" *J Virol*, Jan. 2002; 76(2):609-18.

International Patent Application No. PCT/US2105/013449, filed Jan. 29, 2015; International Search Report and Written Opinion dated Jul. 10, 2015; 14 pages.

International Patent Application No. PCT/US2105/013449, filed Jan. 29, 2015; International Preliminary Report on Patentability dated Aug. 11, 2016; 9 pages.

National Center for Biotechnology Information, National Library of Medicine, National Institutes of Health, GenBank Locus AF354219, Accession No. AF354219, "Avian reovirus GEI10 97M sigma C protein gene, complete cds," [online]. Bethesda, MD [retrieved on Jun. 21, 2015]. Retrieved from the Internet: <URL:ncbi.nlm.nih.gov/nuccore/AF354219>; 1 page.

National Center for Biotechnology Information, National Library of Medicine, National Institutes of Health, GenBank Locus KJ803958, Accession No. KJ803958, "Avian orthoreovirus isolate 91955 Sigma C (S1) gene, partial cds," [online]. Bethesda, MD [retrieved on Jun. 17, 2017]. Retrieved from the Internet: <URL:_ncbi.nlm.nih.gov/nuccore/kj803958>; 2 pgs.

National Center for Biotechnology Information, National Library of Medicine, National Institutes of Health, GenBank Locus KJ803966, Accession No. KJ803966, "Avian orthoreovirus isolate 94594 Sigma C (S1) gene, partial cds," [online]. Bethesda, MD [retrieved on Jun. 17, 2017]. Retrieved from the Internet: <URL:_ncbi.nlm.nih.gov/nuccore/kj803966>; 2 pgs.

National Center for Biotechnology Information, National Library of Medicine, National Institutes of Health, GenBank Locus KJ803967, Accession No. KJ803967, "Avian orthoreovirus isolate 94826 Sigma C (S1) gene, partial cds," [online]. Bethesda, MD [retrieved on Jun. 17, 2017]. Retrieved from the Internet: <URL:ncbi.nlm.nih.gov/nuccore/kj803967>; 2 pgs.

National Center for Biotechnology Information, National Library of Medicine, National Institutes of Health, GenBank Locus KJ803974, Accession No. KJ803974, "Avian orthoreovirus isolate 95522 Sigma C (S1) gene, partial cds," [online]. Bethesda, MD [retrieved on Jun. 17, 2017]. Retrieved from the Internet: <URL:ncbi.nlm.nih.gov/nuccore/kj803974>; 2 pgs.

(Continued)

*Primary Examiner* — Nianxiang Zou

(74) *Attorney, Agent, or Firm* — Mueting, Raasch & Gebhardt, P.A.

(57) ABSTRACT

The present invention relates to novel strains of avian reovirus that were isolated from clinical cases of viral arthritis/tenosynovitis in chickens in the southeast United States. The invention is directed to these novel group 1 and group 2 avian reoviruses, diagnostic assays using antibodies and/or nucleotide- or amino acid-specific components of such viruses, such as the S1 gene encoding the sigma C protein, and to vaccines that protect chickens from disease caused by such viruses.

23 Claims, 15 Drawing Sheets

(56) References Cited

OTHER PUBLICATIONS

National Center for Biotechnology Information, National Library of Medicine, National Institutes of Health, GenBank Locus KJ803990, Accession No. KJ803990, "Avian orthoreovirus isolate 96139 Sigma C (S1) gene, partial cds," [online]. Bethesda, MD [retrieved on Jun. 17, 2017]. Retrieved from the Internet: <URL:ncbi.nlm.nih.gov/nuccore/kj803990>; 2 pgs.

National Center for Biotechnology Information, National Library of Medicine, National Institutes of Health, GenBank Locus KJ879647, Accession No. KJ879647, "Avian orthoreovirus isolate 97361 Sigma C (S1) gene, partial cds," [online]. Bethesda, MD [retrieved on Jun. 17, 2017]. Retrieved from the Internet: <URL:ncbi.nlm.nih.gov/nuccore/kj879647>; 2 pgs.

National Center for Biotechnology Information, National Library of Medicine, National Institutes of Health, GenBank Locus KJ879657, Accession No. KJ879657, "Avian orthoreovirus isolate 97594 Sigma C (S1) gene, partial cds," [online]. Bethesda, MD [retrieved on Jun. 17, 2017]. Retrieved from the Internet: <URL:ncbi.nlm.nih.gov/nuccore/kj879657>; 2 pgs.

National Center for Biotechnology Information, National Library of Medicine, National Institutes of Health, GenBank Locus KJ879673, Accession No. KJ879673, "Avian orthoreovirus isolate 98175 Sigma C (S1) gene, partial cds," [online]. Bethesda, MD [retrieved on Jun. 17, 2017]. Retrieved from the Internet: <URL:ncbi.nlm.nih.gov/nuccore/kj879673>; 2 pgs.

National Center for Biotechnology Information, National Library of Medicine, National Institutes of Health, GenBank Locus KJ879709, Accession No. KJ879709, "Avian orthoreovirus isolate 100557 Sigma C (S1) gene, partial cds," [online]. Bethesda, MD [retrieved on Jun. 17, 2017]. Retrieved from the Internet: <URL:ncbi.nlm.nih.gov/nuccore/kj879709>; 2 pgs.

National Center for Biotechnology Information, National Library of Medicine, National Institutes of Health, GenBank Locus KJ879710, Accession No. KJ879710, "Avian orthoreovirus isolate 100558 Sigma C (S1) gene, partial cds," [online]. Bethesda, MD [retrieved on Jun. 17, 2017]. Retrieved from the Internet: <URL:ncbi.nlm.nih.gov/nuccore/kj879710>; 2 pgs.

National Center for Biotechnology Information, National Library of Medicine, National Institutes of Health, GenBank Locus KJ879720, Accession No. KJ879720, "Avian orthoreovirus isolate 100970 Sigma C (S1) gene, partial cds," [online]. Bethesda, MD [retrieved on Jun. 17, 2017]. Retrieved from the Internet: <URL:ncbi.nlm.nih.gov/nuccore/kj879720>; 2 pgs.

National Center for Biotechnology Information, National Library of Medicine, National Institutes of Health, GenBank Locus KJ879723, Accession No. KJ879723, "Avian orthoreovirus isolate 101021 Sigma C (S1) gene, partial cds," [online]. Bethesda, MD [retrieved on Jun. 17, 2017]. Retrieved from the Internet: <URL:ncbi.nlm.nih.gov/nuccore/kj879723>; 2 pgs.

National Center for Biotechnology Information, National Library of Medicine, National Institutes of Health, GenBank Locus KJ879726, Accession No. KJ879726, "Avian orthoreovirus isolate 101279 Sigma C (S1) gene, partial cds," [online]. Bethesda, MD [retrieved on Jun. 17, 2017]. Retrieved from the Internet: <URL:ncbi.nlm.nih.gov/nuccore/kj879726>; 2 pgs.

National Center for Biotechnology Information, National Library of Medicine, National Institutes of Health, GenBank Locus KM282058, Accession No. KM282058, "Avian orthoreovirus isolate 101343 Sigma C (S1) gene, partial cds," [online]. Bethesda, MD [retrieved on Jun. 17, 2017]. Retrieved from the Internet: <URL:ncbi.nlm.nih.gov/nuccore/km282058>; 2 pgs.

National Center for Biotechnology Information, National Library of Medicine, National Institutes of Health, GenBank Locus KM282067, Accession No. KM282067, "Avian orthoreovirus isolate 101582 Sigma C (S1) gene, partial cds," [online]. Bethesda, MD [retrieved on Jun. 17, 2017]. Retrieved from the Internet: <URL:ncbi.nlm.nih.gov/nuccore/km282067>; 2 pgs.

Alvarado, et al., Abstract T97 "Evaluation of Progeny Protection against a Novel Reovirus Strain associated with Lameness and Poor Performance" International Poultry Scientific Forum. Abstract No. T97, Georgia World Congress Center, Atlanta, Georgia. Jan. 27-28, 2014, available online [Retrieved on May 24, 2015]. Retrieved from the Internet<ippexpo.org/ipsf/docs/2014%20IPSF%20Abstracts.pdf>]; 3 pages.

Alvarado, "Reovirus Outbreaks in Broilers and Broiler Breeders;" 2013 [Retrieved from the Internet May 20, 2015: <thepoultryfederation.com/public/userfiles/files/Reovirus%20in%20Broilers%20%20Broiler%20Breeders.pdf>] 35 pages.

Calvo et al., "Structure of the carboxy-terminal receptor-binding domain of avian reovirus fibre sigma C," *J Mol Biol*, Nov. 18, 2005; 354(1):137-49. Epub Sep. 30, 2005.

Kant et al., "Classification of Dutch and German avian reoviruses by sequencing the sigma C protein," *Vet Res*, Mar-Apr. 2003; 34(2):203-12.

Kool et al., "UniProtKB/TrEMBL Submission Q84144_9REOV. The S1 gene sequences of two Australian avian reoviruses," (Aug. 10, 2010) [Retrieved from the Internet May 22, 2015:<uniprot.org/uniprot/Q84144.txt?version=23>]; 1 page.

Li et al., "Development of a reliable assay protocol for identification of diseases (RAPID)-bioactive amplification with probing for detection of avian reovirus," *J Virol Methods*, Apr. 2008; 149(1):35-41. Epub Mar. 4, 2008.

Liu et al., "Molecular evolution of avian reovirus: evidence for genetic diversity and reassortment of the S-class genome segments and multiple cocirculating lineages" *Virology*, Sep. 15, 2003; 314(1):336-49.

Sellers, "Isolation and characterization of novel avian reoviruses in commercial broilers from clinical cases of tenosynovitis" Department of Population Health Poultry Diagnostic & Research center, College of Veterinary Medicine, University of Georgia, Feb. 7, 2013; 5 pages. Presented at Georgia World Congress Center, Atlanta, Georgia. Jan. 27-28, 2014.

van der Heide et al., "Development of an attenuated apathogenic reovirus vaccine against viral arthritis/tenosynovitis" *Avian Dis.*, 1983; 27(3):698-706.

Liu et al., "Rapid characterization of avian reoviruses using phylogenetic analysis, reverse transcription-polymerase chain reaction and restriction enzyme fragment length polymorphism" Avian Pathol, Apr. 2004; 33(2):171-80.

* cited by examiner

FIG. 1

ATGGACGGATTAACTCAACAGCAGCGAAGAGAAGTCGTGGGGTTGATAC
TGTCGTTGACTTCGAGCGTGAGTACAAGTTCTGGCGATTTGACGCAAAT
TCGTGAACGTCTTTCCGCTTTGGAATCTGCGACTGCGTCGTTGAACGAA
TCTATTAATACAGCTTTGTCTAAGTTAGTGGATTTGTCTGCATCGCTTG
ACAACGTGGCGGCCTCGTTAGCGGAGACGAAAGTGGAAGTGAACTCATT
GGTTTCCGACGTTCAGGGTTTGCGAACTTCTCTTGATTCTTCTGCTTCA
GAGCTGGCTTCTCTATCTTCGTTGGTGCGTGATCACGGCTCTTCGATTG
CTAGCCTACAGAAGAAGTAAGTGTCTTATCGGGTGAGGTAGGCAACCT
TAAAACCTCGGTATCATCGCAGGGCCTTACTATCACTAGCCTTGAGAAA
CGAGTGGAAGCTTTGGAAGGTGGTTCTAGTACGACTCTGTCATTTGCTG
ATCCTCTTAAGTTAGAGGCTGGGACCGTGTCACTCGAGGTAGATCCATA
TTTCTGCTCTGTAAATCGTAATCTGACGTCGTATTCTGCTAATGCTCAG
TTGATGCAATTTCAGTGGTCTGTGAAAGGGGAAGATGGCGCGGCCAACT
CTATTGATATGGACGTGAATGCTCACTCTCATGGTTCACGCACTGATTA
TCTGATGTCAACCAAGCAATCATTGACTGTTACAACGTCTCCCGCTACT
CTCGTCTTTGAACTGGATAGGATTGCTGCTCTTCCCTCTGACCTTTCTC
GCCTAATTCCATGTTATGGTTTTCAGCAAGCTACTTTTCCTGTTGATAT
CTCCTTCCAGCGAGATGGCGTCTCGCATACGTATCAAGTCTATGGGACG
TACACATCTTCTCGCGTCTTCAAGATTACGTTCTCGCCTGGCTCCTCGG

FIG. 2

MDGLTQQQRREVVGLILSLTSSVSTSSGDLTQIRERLSALESATASLNE
SINTALSKLVDLSASLDNVAASLAETKVEVNSLVSDVQGLRTSLDSSAS
ELASLSSLVRDHGSSIASLQKEVSVLSGEVGNLKTSVSSQGLTITSLEK
RVEALEGGSSTTLSFADPLKLEAGTVSLEVDPYFCSVNRNLTSYSANAQ
LMQFQWSVKGEDGAANSIDMDVNAHSHGSRTDYLMSTKQSLTVTTSPAT
LVFELDRIAALPSDLSRLIPCYGFQQATFPVDISFQRDGVSHTYQVYGT
YTSSRVFKITFSPGSS

FIG. 3

ATGGACGGATTAACTCAACAGCAGCGAAGAGAAGTCGTGGGGTTGATAC
TGTCGTTGACTTCGAGCGTGAGTACAAGTTCTGGCGATTTGACGCAAAT
TCGTGAACGTCTTTCCGCTTTGGAATCTGCGACTGCGTCGTTGAACGAA
TCTATTAATACAGCTTTATCTAAGTTAGTGGATTTGTCTGCATCGCTTG
ACAACGTGGCGGCCTCGTTAGCGGAGACGAAAGTGGAAGTGAACTCATT
GGTTTCCGACGTTCAGGGTTTGCGAACTTCTCTTGATTCTTCTGCTTCA
GAGCTGGCTTCTCTATCTTCGTTGGTGCGTGATCACGGCTCTTCGATTG
CTAGCCTACAGAAGAAGTAAGTGTCTTATCGGGTGAGGTAGGCAACCT
TAAAACCTCGGTATCATCGCAGGGCCTTACTATCACTAGCCTTGAGAAA
CGAGTGGAAGCTTTGGAAGGTGGTTCTAGTACGACTCTGTCATTTGCTG
ATCCTCTTAAGTTAGAGGCTGGGACCGTGTCACTCGAGGTAGATCCATA
TTTCTGCTCTGTAAATCGTAATCTGACGTCGTATTCTGCTAATGCTCAG
TTGATGCAATTTCAGTGGTCTGTGAAAGGGGAAGATGGCGCGGCCAACT
CTATTGATATGGACGTGAATGCTCACTCTCATGGTTCACGCACTGATTA
TCTGATGTCAACCAAGCAATCATTGACTGTTACAACGTCTCCCGCTACT
CTCGTCTTTGAACTGGATAGGATTGCTGCTCTTCCCTCTGACCTTTCTC
GCCTAATTCCATGTTATGGTTTTCAGCAAGCTACTTTTCCTGTTGATAT
CTCCTTCCAGCGAGATGGCGTCTCGCATACGTATCAAGTCTATGGGACG
TACACATCTTCTCGCGTCTTCAAGATTACGTTCTCGCCTGGCTCCTCAG

FIG. 4

MDGLTQQQRREVVGLILSLTSSVSTSSGDLTQIRERLSALESATASLNE
SINTALSKLVDLSASLDNVAASLAETKVEVNSLVSDVQGLRTSLDSSAS
ELASLSSLVRDHGSSIASLQKEVSVLSGEVGNLKTSVSSQGLTITSLEK
RVEALEGGSSTTLSFADPLKLEAGTVSLEVDPYFCSVNRNLTSYSANAQ
LMQFQWSVKGEDGAANSIDMDVNAHSHGSRTDYLMSTKQSLTVTTSPAT
LVFELDRIAALPSDLSRLIPCYGFQQATFPVDISFQRDGVSHTYQVYGT
YTSSRVFKITFSPGSS

FIG. 5

ATGGCGGGTCTCAGTCCATCACAGCGAAGAGAGGTCGTCAGCTTGATAC
TGTCATTGACTTCGAACGCGACTATAAGTCCTGGCGATTTGACGACAAT
CCATGAGCGGTTGACTAATTTGGAAGCGTCTACAGAATCACTATACCGC
TCCATCTCCAGCATGTCTGTTACTGTTTCCGACGTTTCTACAGATTTGC
AGAACGTGACTCGCGCTCTGGATGATGTGATCACCAACTTAAATGGTAT
GAGAGCCACCATTACTGCACTTCAAGATTCTGTTTCCACTCTCTCAACA
ACTGTGACCGACTTATCAAGCACTTCTTCTGCGCATTCGGAAACTCTAT
CTTCACTCCGAAATACAGTTAATGGGAACTCCACTACCATTGGTAATTT
GAAAAGTGATGTATCATCAAATGGCCTAGCTATCACAGACCTGCAGAGT
CGCGTTAAATCCTTGGAGTCTACTTCGAGTCACGGACTGTCCTTTTCTC
CTCCTCTTAGTGTCGCTGACGGCGTGGTGTCGTTGAATATGGACCCGTA
CTTTTGCTCTCAGCGAGTTTCCTTGACATCTTACTCAGCAGAGGCTCAA
CTAATGCAATTCCAATGGATGGCCAGAGGTTCTAACGGATCATCGGACA
ATATTGACATGAACGTTAACGCCCACTGTCATGGGAGACGCACTGACTA
TATAATGTCGTCTACGGGAGGTCTTACGGTTACTCGTAATGCCGTGTCC
TTAACCTTCGATTTGAGTTATATTACAAAGCTCCCATCGGACCTCTCAC
GTCTTATCCCCAGTGCGGGATTTCAAGCCGCGTCGTTTCCAGCGGATGT
ATCCTTCACCAGAGATTCCACAACCCATGCGTATCAAGCTTATGgAGTA
TATTCCAGCTCTCGCGTATTTACTATTACTTTCCCGACTGGTGGTGACG

FIG. 6

MAGLSPSQRREVVSLILSLTSNATISPGDLTTIHERLTNLEASTESLYR
SISSMSVTVSDVSTDLQNVTRALDDVITNLNGMRATITALQDSVSTLST
TVTDLSSTSSAHSETLSSLRNTVNGNSTTIGNLKSDVSSNGLAITDLQS
RVKSLESTSSHGLSFSPPLSVADGVVSLNMDPYFCSQRVSLTSYSAEAQ
LMQFQWMARGSNGSSDNIDMNVNAHCHGRRTDYIMSSTGGLTVTRNAVS
LTFDLSYITKLPSDLSRLIPSAGFQAASFPADVSFTRDSTTHAYQAYGV
YSSSRVFTITFPTGGD

AVIAN REOVIRUS VACCINES

CONTINUING APPLICATION DATA

This application is a continuation-in-part of International Application No. PCT/US2015/013449, filed Jan. 29, 2015, which claims the benefit of U.S. Provisional Application Ser. No. 61/932,995, filed Jan. 29, 2014, all of which are incorporated by reference herein in their entireties.

SEQUENCE LISTING

This application contains a Sequence Listing electronically submitted via EFS-Web to the United States Patent and Trademark Office as an ASCII text file entitled "235-02410120_sequence_listing_ST25" having a size of 56 kilobytes and created on Oct. 4, 2016. The information contained in the Sequence Listing is incorporated by reference herein.

BACKGROUND

Avian reoviruses are associated with several diseases in poultry, including malabsorption syndrome and runting and stunting syndrome (RSS), although their role as primary pathogens in these clinical syndromes is not clear. In contrast, the association of avian reoviruses with clinical cases of viral arthritis/tenosynovitis is quite clear, as reoviruses have been isolated from the tendons of affected birds. The control of reovirus-induced viral arthritis/tenosynovitis can be achieved by vaccination of broiler breeders with a combination of live and/or inactivated vaccines with maternal immunity passed on to progeny for early protection against field challenge. In broilers, live attenuated vaccines are available for use at day-of-hatch and for use in ovo. Current commercial vaccine strains (S1133, 1733, 2408, and 2177 to name a few) have been used for decades to control diseases associated with reovirus. However, these commercial vaccine strains were isolated in the 1960-1970s and do not provide protection against currently circulating reovirus isolates from confirmed cases of viral arthritis/tenosynovitis. Thus there is a need for the isolation and characterization of currently circulating avian reoviruses and the development of effective vaccines.

SUMMARY OF THE INVENTION

The present invention includes genetically and serologically distinct group 1 and group 2 avian reoviruses isolated from clinical cases of viral arthritis (VA)/tenosynovitis in chickens.

The present invention includes an isolated group 1 avian reovirus, wherein a group 1 avian reovirus includes a sigma C protein having an amino acid sequence with at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:2 and/or SEQ ID NO:4. In some aspects, a group 1 avian reovirus includes a sigma C protein having an amino acid sequence with at least about 99% sequence identity to SEQ ID NO:2. In some aspects, a group 1 avian reovirus includes a sigma C protein having an amino acid sequence with at least about 99% sequence identity to SEQ ID NO:4. In some aspects, a group 1 avian reovirus includes a sigma C protein having an amino acid sequence SEQ ID NO:2. In some aspects, a group 1 avian reovirus includes a sigma C protein having an amino acid sequence SEQ ID NO:4. In some aspects, a group 1 avian reovirus is attenuated, inactivated, or killed. In some aspects, a group 1 avian reovirus is attenuated by at least 25 passages in an egg or a host cell line.

The present invention includes an isolated group 1 avian reovirus, wherein a group 1 avian reovirus includes an S1 gene having a nucleotide sequence with at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:1 and/or SEQ ID NO:3. In some aspects, a group 1 avian reovirus includes an S1 gene having a nucleotide sequence having a nucleotide sequence with at least about 99% sequence identity to SEQ ID NO:1. In some aspects, a group 1 avian reovirus includes an S1 gene having a nucleotide sequence having a nucleotide sequence with at least about 99% sequence identity to SEQ ID NO:3. In some aspects, a group 1 avian reovirus includes an S1 gene having the nucleotide sequence SEQ ID NO:1. In some aspects, a group 1 avian reovirus includes an S1 gene having the nucleotide sequence SEQ ID NO:3. In some aspects, a group 1 avian reovirus includes a sigma C protein having an amino acid sequence with at least about 99% sequence identity to SEQ ID NO:4. In some aspects, a group 1 avian reovirus is attenuated, inactivated, or killed. In some aspects, a group 1 avian reovirus is attenuated by at least 25 passages in an egg or a host cell line.

The present invention includes an isolated group 2 avian reovirus, wherein a group 2 avian reovirus includes a sigma C protein having an amino acid sequence with at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:6. In some aspects, a group 2 avian reovirus includes a sigma C protein having an amino acid sequence with at least about 99% sequence identity to SEQ ID NO:6. In some aspects, a group 2 avian reovirus includes a sigma C protein having an amino acid sequence SEQ ID NO:6. In some aspects, a group 2 avian reovirus is attenuated, inactivated, or killed. In some aspects, a group 2 avian reovirus is attenuated by at least 25 passages in an egg or a host cell line.

The present invention includes an isolated group 1 avian reovirus, wherein a group 1 avian reovirus includes an S1 gene comprising a nucleotide sequence with at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:5. In some aspects, a group 2 avian reovirus includes an S1 gene having a nucleotide sequence having a nucleotide sequence with at least about 99% sequence identity to SEQ ID NO:5. In some aspects, a group 2 avian reovirus includes an S1 gene having the nucleotide sequence SEQ ID NO:5. In some aspects, a group 2 avian reovirus is attenuated, inactivated, or killed. In some aspects, a group 2 avian reovirus is attenuated by at least 25 passages in an egg or a host cell line.

In some aspects, the present invention includes a group 1 avian reovirus, wherein a group 1 avian reovirus includes avian reovirus strain 94594 and derivatives and progeny thereof. In some aspects, avian reovirus strain 94595 is killed, inactivated or attenuated by at least 25 passages in an egg or a host cell line.

In some aspects, the present invention includes a group 1 avian reovirus, wherein a group 1 avian reovirus includes avian reovirus strain 94826 and derivatives and progeny thereof. In some aspects, strain 948264 is killed, inactivated, or attenuated by at least 25 passages in an egg or a host cell line.

In some aspects, the present invention includes a group 2 avian reovirus, wherein the avian reovirus includes avian reovirus strain 96139 and derivatives and progeny thereof. In some aspects, avian reovirus strain 96139 is killed, inactivated, or attenuated by at least 25 passages in an egg or a host cell line.

Included in the present invention are compositions including one or more of the avian reoviruses as described herein. Such compositions may further include an adjuvant and/or an antigenic determinant from one or more additional pathogens infectious to poultry.

Included in the present invention are vaccines including one or more of the avian reoviruses of the present invention, as described herein. Such vaccines may further include an adjuvant and/or an antigenic determinant from one or more additional pathogens infectious to poultry.

Included in the present invention are immunological compositions for raising antibodies in poultry including one or more of the avian reoviruses described above and herein. Such compositions may further include an adjuvant and/or an antigenic determinant from one or more additional pathogens infectious to poultry.

The present invention includes a diagnostic kit including one or more of the avian reoviruses described above and herein.

The present invention includes a method of producing anti-reovirus antibodies in poultry, the method including administering an isolated avian reovirus, a composition, or a vaccine of the preset invention to the bird.

The present invention includes a method for protecting a bird of the order Galliformes against pathology or disease induced by an avian reovirus, the method including administering an isolated avian reovirus, a composition, or a vaccine of the present invention to the bird.

The present invention includes a method for reducing susceptibility of a bird of the order Galliformes against pathology or disease induced by an avian reovirus, the method including administering an isolated avian reovirus, a composition, or a vaccine of the present invention to the bird.

The present invention includes a method for reducing viral arthritis and/or tenosynovitis in a bird of the order Galliformes, the method including administering an isolated avian reovirus, a composition, or a vaccine of the present invention to the bird.

The present invention includes a method for preventing viral arthritis and/or tenosynovitis in a bird of the order Galliformes, the method including administering an isolated avian reovirus, a composition, or a vaccine of the present invention to the bird.

In some aspects of the methods of the present invention, the bird includes a chicken or turkey.

In some aspects of the methods of the present invention, administration includes administration before or after hatching.

In some aspects of the methods of the present invention, administration includes in ovo administration. In some aspects, in ovo administration includes administration at about 13 days, about 14 days, about 15 days, about 16 days, about 17 days, about 18 days, about 19 days, about 20 days, or any range thereof.

In some aspects of the methods of the present invention, administration includes administration to a breeder hen.

The present invention includes an antibody that binds to an avian reovirus a group 1 or group 2 avian reovirus, as described herein and does not bind to avian reovirus strain S1133, 1733, 2408, and/or 2177. In some aspects, the antibody is a monoclonal antibody.

The present invention includes a method of detecting exposure to an avian reovirus in a bird, the method including determining that an antisera sample obtained from the bird specifically binds to an avian reovirus of the present invention, or component thereof.

The present invention includes a method of detecting exposure to an avian reovirus in a bird, the method including determining that an antisera sample obtained from the bird specifically binds to a sigma C protein of a group 1 avian reovirus or group 2 avian reovirus of the present invention.

The present invention includes a method of detecting an avian reovirus infectious agent in a sample, the method including detecting the hybridization of a polynucleotide comprising SEQ ID NO:1, SEQ ID NO:3, or SEQ ID NO: 5, or a fragment thereof, to the sample.

The present invention includes a method of detecting an avian reovirus in a sample, the method including producing a polymerase chain reaction (PCR) amplification product with at least one primer derived from SEQ ID NO:1, SEQ ID NO:3, or SEQ ID NO:5.

BRIEF DESCRIPTION OF THE FIGURES

FIG. 1. S1 nucleotide sequence encoding the sigma C protein (base pairs 1-931) from group 1 2012 VA variant field isolate 94594 (SEQ ID NO:1).

FIG. 2. S1 amino acid sequence encoding sigma C (amino acids 1-310) from group 1 2012 VA variant field isolate 94594 (SEQ ID NO:2).

FIG. 3. S1 nucleotide sequence encoding the sigma C protein (base pairs 1-931) from group 1 2012 VA variant field isolate 94826 (SEQ ID NO:3).

FIG. 4. S1 amino acid sequence encoding sigma C (amino acids 1-310) from group 1 2012 VA variant field isolate 94826 (SEQ ID NO:4).

FIG. 5. S1 nucleotide sequence encoding the sigma C protein (base pairs 1-931) from group 2 2012 VA variant field isolate 96139 (SEQ ID NO:5).

FIG. 6. S1 amino acid sequence encoding the sigma C protein (amino acids 1-310) from group 2 2012 VA variant field isolate 96139 (SEQ ID NO:6).

FIG. 8. Percent identity and divergence based on multiple alignment generated using Clustal W algorithm.

FIG. 21. The alignment of reovirus Sigma C amino acid sequences for the vaccine strains S1133 (SEQ ID NO:9), 1733 (SEQ ID NO:10), Enterovax (SEQ ID NO:11), and 2177 (SEQ ID NO:12) with various Group 1 and Group 2 reovirus isolates. Group I isolates include Ck-Canada-97594Td-2013 (SEQ ID NO:13), Ck-GA-91955Td-2011 (SEQ ID NO:14), Ck-MS-101021Td-2013 (SEQ ID NO:15), Ck-NC-97361Td-2013 (SEQ ID NO:16), Ck-SC-101343Td-2013 (SEQ ID NO:17), Ck-TN-101279Td-2013 (SEQ ID NO:18), Ck-TX-100970Td-2013 (SEQ ID NO:19), and Ck-AR-100557Td-2013 (SEQ ID NO:20). Group 2 isolates include Ck-AR-100558Td-2013 (SEQ ID NO:21), Ck-GA-98175Td-2013 (SEQ ID NO:22), Ck-MO-101582Td-2013 (SEQ ID NO:23), and Ck-AL-95524Td-2012 (SEQ ID NO:24). Amino acids that match S1133 represented by a dot (.) and amino acids that are different have single letter AA representing substitution.

FIG. 23A and FIG. 23B are two sides of the Sigma C protein structure. Shaded knobs represent amino acid substitutions in the Sigma C protein of the group 1 reovirus compared to S1133.

FIG. 24A and FIG. 24B are two sides of the Sigma C protein structure. Shaded knobs represent amino acid substitutions in the Sigma C protein of the group 2 reovirus compared to S1133.

DETAILED DESCRIPTION OF ILLUSTRATIVE EMBODIMENTS

Figure 7:
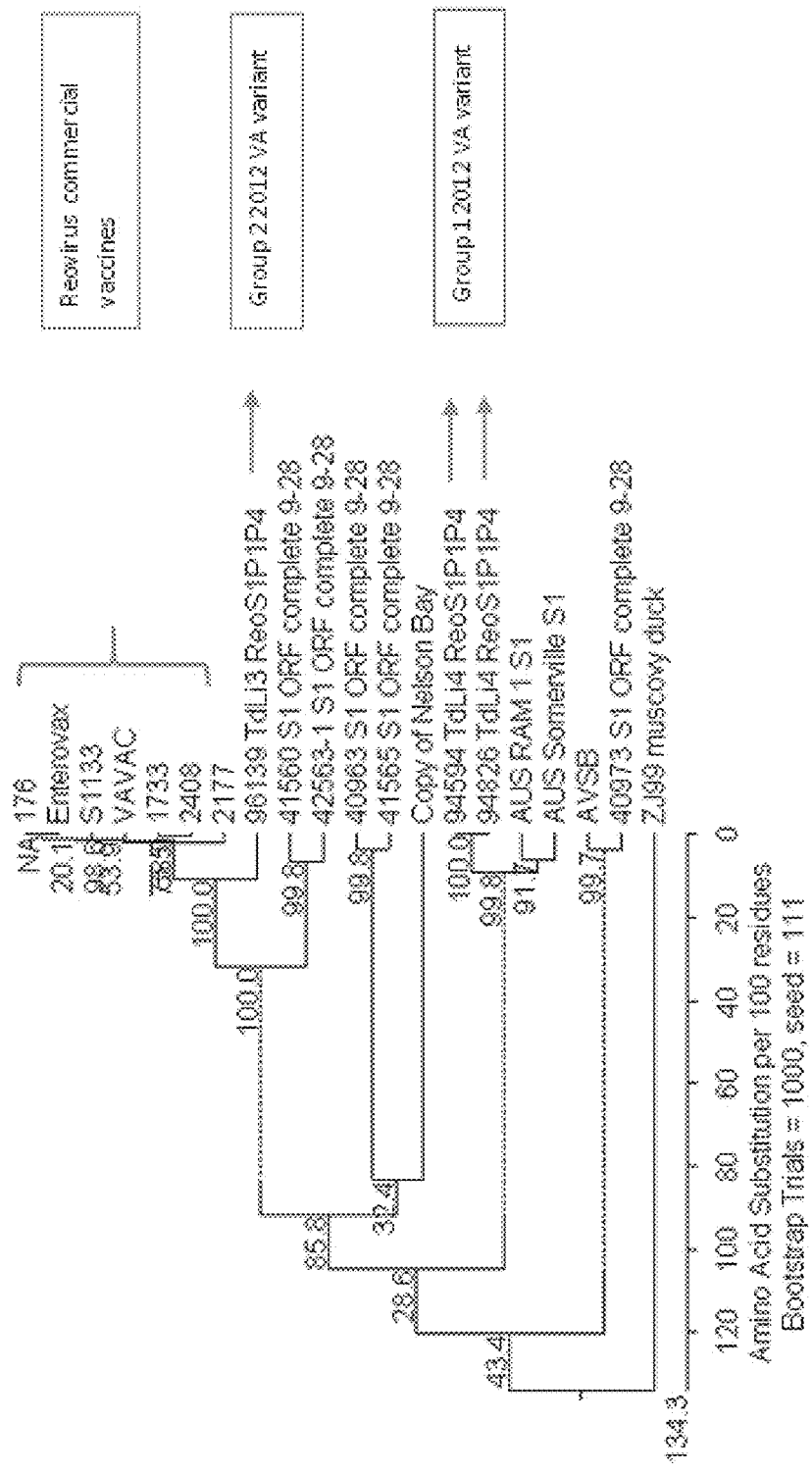
FIG. 7. Multiple alignment of sigma C amino acid sequences using Clustal W and resulting phylogenetic tree with 1000 bootstrap replicates. Bootstrap confidence levels indicated by numbers on each tree node.

With the present invention, two genetically and serologically distinct groups of avian reoviruses have been isolated from clinical cases of viral arthritis (VA)/tenosynovitis from across the US and Canada. Genetic analysis of the avian reovirus sigma C protein revealed novel group 1 and group 2 genotypes unrelated to current avian reovirus vaccine strains. Serological evaluation of the viruses revealed little to no cross neutralization with known antisera to current commercial reovirus vaccines. In addition, pathogenicity and progeny protection studies confirm that current commercial vaccines do not provide sufficient protection in progeny from vaccinated breeder hens. Current reovirus vaccine strains were isolated in the 1960-1970s and do not provide protection against currently circulating reovirus isolates from confirmed cases of viral arthritis/tenosynovitis.

Avian reoviruses, along with mammalian reoviruses, comprise the genus Orthoreovirus in the family Reoviridae. These viruses contain 10 dsRNA genome segments enclosed within a non-enveloped, icosahedral double capsid of approximately 80 nm. The genome segments can be separated based on electrophoretic mobility into three large (L1, L2, L3), three medium (M1, M2, M3) and four small (S1, S2, S3, S4) segments which code for proteins $\lambda 1$, $\lambda 2$, $\lambda 3$, $\mu 1$, $\mu 2$, $\mu NS$, $\sigma 3$, $\sigma 1$, $\sigma 2$, $\sigma NS$, respectively. The $\sigma 2$ protein is an outer capsid protein which carries group-specific neutralizing epitopes. It also binds double-stranded RNA and has been identified as a zinc metalloprotein. The sigma C protein, the minor outer capsid protein encoded by the $\sigma 1$ segment, is the target for molecular characterization of avian reoviruses and is responsible for cell attachment, as well as, induction of type-specific neutralizing antibodies.

An avian reovirus virion includes a capsid, a core, and a nucleoprotein complex. The virus capsid is not enveloped. The capsid/nucleocapsid is isometric with icosahedral symmetry and has a diameter of about 80-82 nm. The capsid shells of virions are composed of two layers. All shells are usually present, or the outer shell is often lost during preparation. Capsids appear round. The capsid surface structure reveals a regular pattern with distinctive features. The capsomer arrangement is clearly visible. Surface projections are not present. Inner capsids core has a diameter of about 60 nm. Virus preparations contain one particle component. The core is spherical and consists of the dsRNA genome with a diameter of about 49 nm. The ends of the fibers protrude almost through to the capsid surface.

In the avian reovirus vaccine strain S1133 the s1 mRNA transcript is 1644 nucleotide long and contains three out-of-phase and partially overlapping cistrons. The first cistron (ORF-1, nucleotides 25-319) expresses p10, the second cistron (ORF-2, nucleotides 293-731) expresses p17 and the third cistron (ORF-3, nucleotides 630-1608) expresses the cell attachment sigma protein C.

Analysis of the sigma C amino acid sequences of reovirus vaccine strains S1133, 1733, 2408 and 2177 reveals a >99% similarity among these vaccine strains. Genotypic characterization of reovirus field isolates includes comparison of field isolates to vaccine strains, as well as, all reovirus sequences available in the public domain and PDRC database. Similarity of the genotype is reported out for field isolates as the highest percentage similarity to another sequence whether a field isolate or vaccine strain.

With the present invention, two genetically and serologically distinct groups of avian reoviruses have been isolated from clinical cases of tenosynovitis. Genetic analysis of the avian reovirus sigma C protein revealed novel genotypes unrelated to current avian reovirus vaccine strains. Serological evaluation of the viruses revealed little to no cross neutralization with known antisera to current commercial reovirus vaccines. In addition, pathogenicity and progeny protection studies have been performed to confirm that current commercial vaccines do not provide sufficient protection in progeny from vaccinated breeder hens.

Figure 22:
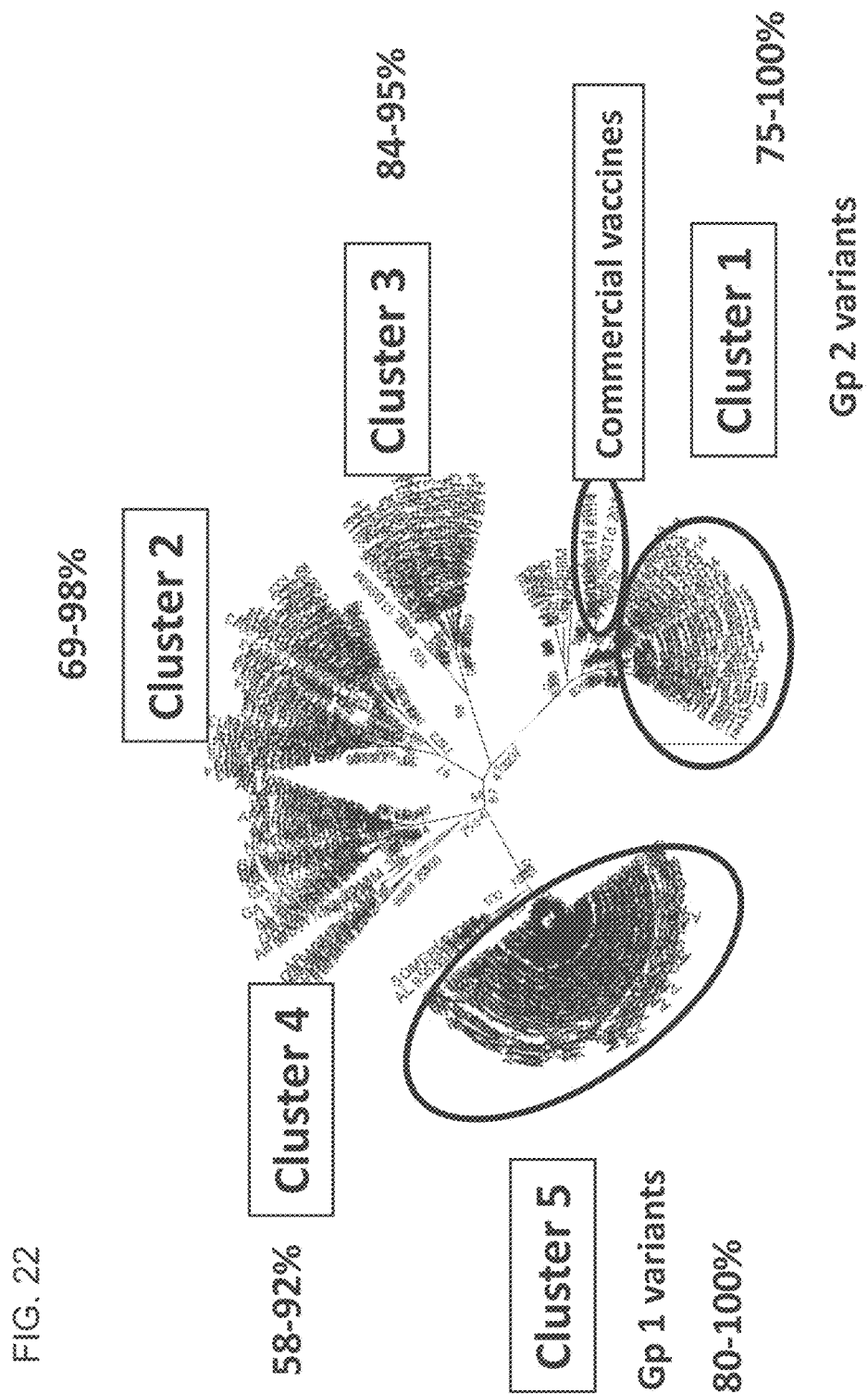
FIG. 22. Phylogenetic analysis of Sigma C.

The two genetic/serologic groups of field isolates described herein are called group 1 2012 VA variant (also referred to herein as "group 1 avian reovirus") and group 2 2012 VA variant (also referred to herein as "group 2 avian reovirus"). Following the nomenclature of Kant et al. ("Classification of Dutch and German avian reoviruses by sequencing the sigma C protein," Vet Res, 2003; 34(2):203-12), group 1 avian reovirus isolates are placed in Genotype Cluster 5 and group 2 avian reovirus are placed in Genotype Cluster 1. This is shown in FIG. 22.

Reoviruses from the group 1 2012 VA variant and/or group 2 2012 VA variant may be used in either live attenuated and/or killed/inactivated vaccines. In some aspects, such a vaccine may be an autogenous vaccine.

A group 1 avian reovirus of the present invention may have a C sigma protein with an amino acid sequence with at least about 50% sequence identity, at least about 55% sequence identity, at least about 60% sequence identity, at least about 65% sequence identity, at least about 70% sequence identity, at least about 75% sequence identity, at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:2. In some aspects, a group 1 avian reovirus of the present invention may have a C sigma protein having an amino acid sequence of SEQ ID NO:2. In some embodiments, a group 1 avian reovirus as described herein has a C sigma protein with at least one substitution modification relative to SEQ ID NO:2.

A group 1 avian reovirus of the present invention may have a C sigma protein with an amino acid sequence with at least about 50% sequence identity, at least about 55% sequence identity, at least about 60% sequence identity, at least about 65% sequence identity, at least about 70% sequence identity, at least about 75% sequence identity, at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:4. In some aspects, a group 1 avian reovirus of the present invention may have a C sigma protein having an amino acid sequence of SEQ ID NO:4. In some embodiments, a group 1 avian reovirus as described herein has a C sigma protein with at least one substitution modification relative to SEQ ID NO:4.

A group 1 avian reovirus of the present invention may have a C sigma protein with an amino acid sequence with at least about 50% sequence identity, at least about 55% sequence identity, at least about 60% sequence identity, at least about 65% sequence identity, at least about 70% sequence identity, at least about 75% sequence identity, at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:13, SEQ ID NO:14, SEQ ID NO:15, SEQ ID NO:16, SEQ ID NO:17, SEQ ID NO:18, SEQ ID NO:19, or SEQ ID NO:20. In some aspects, a group 1 avian reovirus of the present invention may have a C sigma protein having an amino acid sequence of SEQ ID NO:13, SEQ ID NO:14, SEQ ID NO:15, SEQ ID NO:16, SEQ ID NO:17, SEQ ID NO:18, SEQ ID NO:19, or SEQ ID NO:20. In some embodiments, a group 1 avian reovirus as described herein has a C sigma protein with at least one substitution modification relative to SEQ ID NO:13, SEQ ID NO:14, SEQ ID NO:15, SEQ ID NO:16, SEQ ID NO:17, SEQ ID NO:18, SEQ ID NO:19, or SEQ ID NO:20.

A group 1 avian reovirus of the present invention may have a C sigma protein encoded by a nucleotide sequence with at least about 50% sequence identity, at least about 55% sequence identity, at least about 60% sequence identity, at least about 65% sequence identity, at least about 70% sequence identity, at least about 75% sequence identity, at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:1. In some aspects, a group 1 avian reovirus of the present invention may have a C sigma protein encoded by a nucleotide sequence having SEQ ID NO:1. In some embodiments, a group 1 avian reovirus as described herein has a C sigma protein encoded by a nucleotide sequence with at least one substitution modification relative to SEQ ID NO:1.

A group 1 avian reovirus of the present invention may have a C sigma protein encoded by a nucleotide sequence with at least about 50% sequence identity, at least about 55% sequence identity, at least about 60% sequence identity, at least about 65% sequence identity, at least about 70% sequence identity, at least about 75% sequence identity, at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:3. In some aspects, a group 1 avian reovirus of the present invention may have a C sigma protein encoded by a nucleotide sequence having SEQ ID NO:3. In some embodiments, a group 1 avian reovirus as described herein has a C sigma protein encoded by a nucleotide sequence with at least one substitution modification relative to SEQ ID NO:3.

Figure 21:
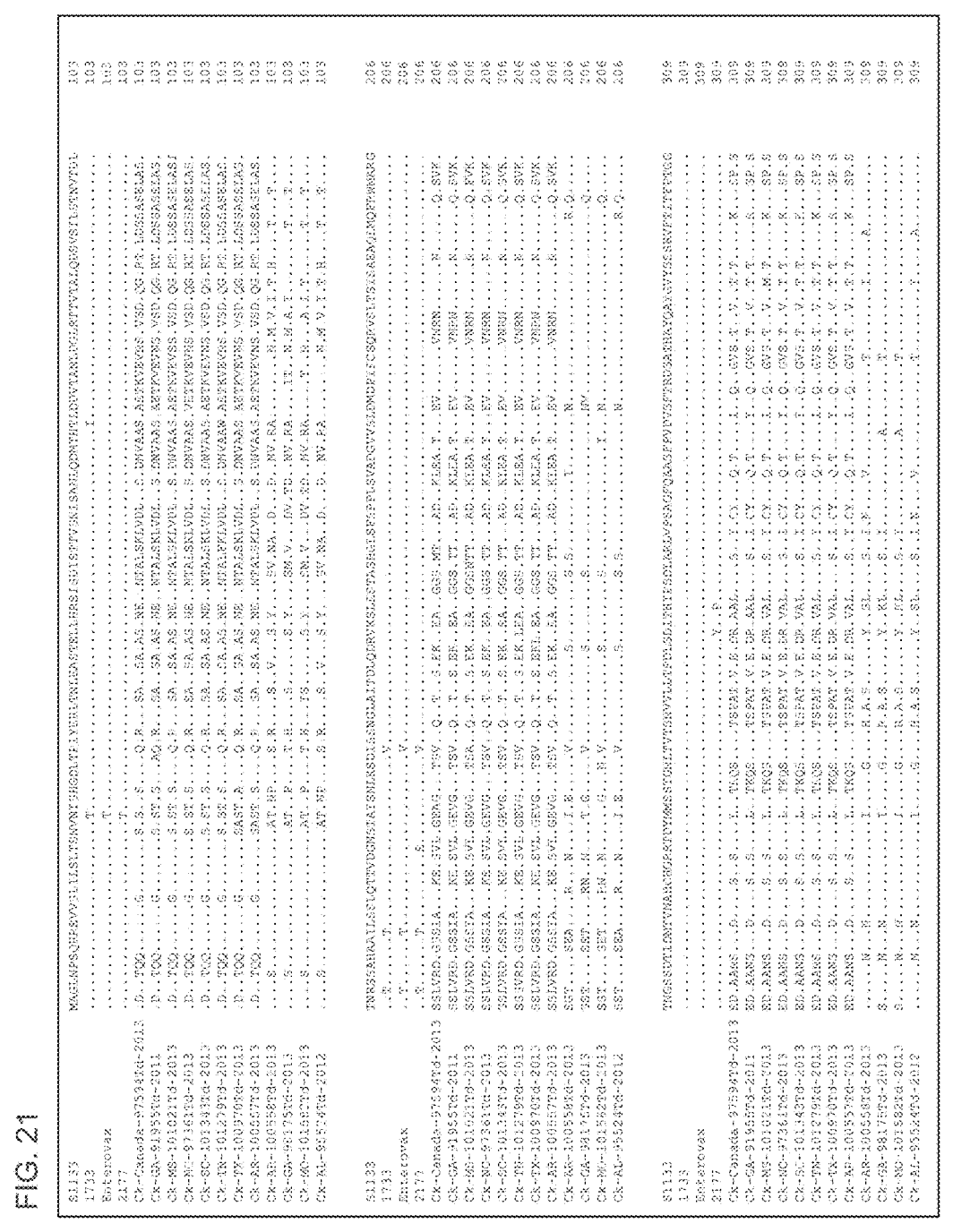

In some embodiments, a group 1 avian reovirus is one of those represented on Table 4 or FIG. 21, or a progeny, attenuation, or derivative thereof.

In some embodiments, a group 1 avian reovirus is avian reovirus CK/945494/Tendon/GA/2012 (also referred to herein as "group 1 2012 VA variant field isolate 94594," or "94594"), or a progeny, attenuation, or derivative thereof.

In some embodiments, a group 1 avian reovirus is avian reovirus CK/94826/Tendon/GA/2012 (also referred to herein as "group 1 2012 VA variant field isolate 94826," or "94826"), or a progeny, attenuation, or derivative thereof.

A group 2 avian reovirus of the present invention may have a C sigma protein with an amino acid sequence with at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:6. In some aspects, a group 2 avian reovirus of the present invention may have a C sigma protein having an amino acid sequence of SEQ ID NO:6. In some embodiments, a group 2 avian reovirus as described above has a C sigma protein with at least one substitution modification relative to SEQ ID NO:6.

A group 2 avian reovirus of the present invention may have a C sigma protein with an amino acid sequence with at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:21, SEQ ID NO:22, SEQ ID NO:23, or SEQ ID NO:24. In some aspects, a group 2 avian reovirus of the present invention may have a C sigma protein having an amino acid sequence of SEQ ID NO:21, SEQ ID NO:22, SEQ ID NO:23, or SEQ ID NO:24. In some embodiments, a group 2 avian reovirus as described above has a C sigma protein with at least one substitution modification relative to SEQ ID NO:21, SEQ ID NO:22, SEQ ID NO:23, or SEQ ID NO:24.

A group 2 avian reovirus of the present invention may have a C sigma protein encoded by a nucleotide sequence with at least at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:5. In some aspects, a group 1 avian reovirus of the present invention may have a C sigma protein encoded by a nucleotide sequence having SEQ ID NO:5. In some embodiments, a group 1 avian reovirus as described herein has a C sigma protein encoded by a nucleotide sequence with at least one substitution modification relative to SEQ ID NO:5.

In some embodiments, a group 2 avian reovirus is one of those represented on Table 4 or FIG. 21, or a progeny, attenuation, or derivative thereof.

In some embodiments, a group 2 avian reovirus is avian reovirus CK/96139/Tendon/GA/2012 (also referred to herein as "group 2 2012 VA variant field isolate 96139," or "96139"), or a progeny attenuation, or derivative thereof.

An avian reovirus as described herein, or cell line infected with such a virus, may be put on deposit with the American Type Culture Collection (ATCC®), 10801 University Boulevard, Manassas, Va. 20110-2209, USA. Such a deposit may be in accordance with the Budapest Treaty on the International Recognition of the Deposit of Microorganisms for the Purposes of Patent Procedure.

Avian reovirus according to the invention can be prepared by conventional methods, including, but not limited to, any of those described in the examples section included herewith. In brief, a substrate able to support the replication of an avian reovirus is inoculated with an avian reovirus of the present invention and propagated until the virus is replicated to a desired infectious titer, or antigen mass content. Reovirus containing material is then harvested. Suitable substrates may include primary (avian) cell cultures, such as, for example, chicken embryo liver cells, chicken embryo fibroblasts, or chicken kidney cells, mammalian cell lines, such as, for example, the VERO cell line or the BGM-70 cell line, or avian cell lines, such as, for example, QT-35, QM-7 or LMH. In some applications, embrynated eggs may be used.

The present invention includes a method of detecting exposure to a group 1 and/or group 2 avian reovirus in a bird, the method including a determination of whether or not an antisera sample obtained from the bird specifically binds to a virus, cell line, cell pellet, supernatant, and/or polypeptide of the present invention. For example, the present invention includes the use of one or more avian reoviruses of the present invention in methods of detecting exposure to an avian reovirus in a bird, the method including determining that an antisera sample obtained from the bird specifically binds to an avian reovirus of the present invention. Such an avian reovirus includes, any of those described herein, including, but not limited any of the avian reovirus strains listed in Table 4, including, but not limited to avian reovirus strain 94594, 94826, or 96139. Such an avian reovirus may be inactivated, killed, and/or lyophilized. The present invention also includes diagnostic kits including one or more of the avian reoviruses of the present invention. Such a kit may include as additional components, such as for example, a positive control virus, a negative control virus, a secondary antibody, and/or a detectable marker.

The present invention includes an isolated sigma C polypeptide having an amino acid sequence with at least about 50% sequence identity, with at least about 55% sequence identity, with at least about 60% sequence identity, with at least about 65% sequence identity, with at least about 70% sequence identity, with at least about 75% sequence identity, with at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:2, SEQ ID NO:4, and/or SEQ ID NO:6. In some aspects, the present invention includes an isolated sigma C polypeptide having an amino acid sequence with SEQ ID NO:2, SEQ ID NO:4, and/or SEQ ID NO:6. In some aspects, the present invention includes an isolated sigma C polypeptide having an amino acid sequence with at least one least one substitution modification relative to SEQ ID NO:2, SEQ ID NO:4, and/or SEQ ID NO:6.

The present invention includes an isolated sigma C polypeptide having an amino acid sequence with at least about 50% sequence identity, with at least about 55% sequence identity, with at least about 60% sequence identity, with at least about 65% sequence identity, with at least about 70% sequence identity, with at least about 75% sequence identity, with at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and/or SEQ ID NO:24. In some aspects, the present invention includes an isolated sigma C polypeptide having an amino acid sequence with SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and/or SEQ ID NO:24. In some aspects, the present invention includes an isolated sigma C polypeptide having an amino acid sequence with at least one least one substitution modification relative to SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and/or SEQ ID NO:24.

The present invention includes an isolated sigma C polypeptide having an amino acid sequence encoded by a nucleotide sequence with at least about 50% sequence identity, with at least about 55% sequence identity, with at least about 60% sequence identity, with at least about 65% sequence identity, with at least about 70% sequence identity, with at least about 75% sequence identity, with at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence identity to SEQ ID NO:1, SEQ ID NO:3, and/or SEQ ID NO:5. In some aspects, the present invention includes an isolated sigma C polypeptide having an amino acid sequence encoded by nucleotide sequence SEQ ID NO:1, SEQ ID NO:3, and/or SEQ ID NO:5. In some aspects, the present invention includes an isolated sigma C polypeptide having an amino acid sequence encoded by a nucleotide sequence with at least one least one substitution modification relative to SEQ ID NO:1, SEQ ID NO:3, and/or SEQ ID NO:5.

The present invention includes polypeptides as described herein, truncations and fragments thereof. Truncations include, but are not limited to, amino acid sequences in which one, two, three, four, five, six, seven, eight, nine, ten, or more amino acids are removed from the amino terminus of an amino acid sequence and/or one, two, three, four, five, six, seven, eight, nine, ten, or more amino acids are removed from the carboxy terminus of an amino acid sequence.

Fragments include, but are not limited to, for example, fragments having about 5, about 10, about 15, about 20, about 25, about 50, about 75, about 100, about 150, about 200, about 250, about 300, about 350, about 400, about 450, about 500, about 550, about 600, about 650, and about 700 consecutive amino acid residues of a sequence described herein. Fragments also include, for example, fragments of a size range of any combination of the above fragment sizes. Fragments include, but are not limited to, for example, fragments having at least 5, at least 10, at least 15, at least 20, at least 25, at least 50, at least 75, at least 100, at least 150, at least 200, at least 250, at least 300, at least 350, at least 400, at least 450, at least 500, at least 550, at least 600, at least 650, and at least 700 consecutive amino acid residues of a sequence described herein.

The present invention includes polypeptides having an amino acid sequence with one, two, three, four, five, six, seven, eight, nine, ten, eleven, twelve, thirteen, fourteen, fifteen, sixteen, seventeen, eighteen, nineteen, twenty, or more amino acid changes from an amino acid sequence described herein, or fragments thereof. Such amino acid changes include, but are not limited to, conservative amino acid changes.

The present invention includes the use of one or more polypeptides of the present invention in methods of detecting exposure to an avian reovirus in a bird, the method including determining that an antisera sample obtained from the bird specifically binds to a polypeptide of the present invention. Such polypeptides include, any of those described herein, including, but not limited to SEQ ID NO:2, SEQ ID NO:4, and SEQ ID NO:6, and derivatives and fragments thereof. The present invention also includes diagnostic kits including one or more of the polypeptides of the present invention. Such a kit may include as additional components, such as for example, a positive control polypeptide, a negative control polypeptide, a secondary antibody, a detectable marker. In some embodiments, the polypeptide is bound to a solid support, for example, a bead, a chip, a test stripe, or a microtiter plate.

The present invention includes an isolated polynucleotide sequence having at least about 50% sequence identity, at least about 55% sequence identity, at least about 60% sequence identity, at least about 65% sequence identity, at least about 70% sequence identity, at least about 75% sequence identity, at least about 75% sequence identity, at least about 80% sequence identity, at least about 85% sequence identity, at least about 90% sequence identity, at least about 95% sequence identity, at least about 98% sequence identity, or at least about 99% sequence identity to SEQ ID NO:1, SEQ ID NO:3, or SEQ ID NO:5. The present invention includes an isolated polynucleotide sequence having SEQ ID NO:1, SEQ ID NO:3, or SEQ ID NO:5, a truncation, or fragment thereof. In some aspects, the present invention includes an isolated polynucleotide sequence as described herein with at least one least one substitution modification relative to SEQ ID NO:1, SEQ ID NO:3, or SEQ ID NO:5.

The present invention includes an isolated polynucleotide sequence having at least about 50% sequence identity, at least about 55% sequence identity, at least about 60% sequence identity, at least about 65% sequence identity, at least about 70% sequence identity, at least about 75% sequence identity, at least about 75% sequence identity, at least about 80% sequence identity, at least about 85% sequence identity, at least about 90% sequence identity, at least about 95% sequence identity, at least about 98% sequence identity, or at least about 99% sequence identity to a nucleotide sequence encoding SEQ ID NO:2, SEQ ID NO:4, or SEQ ID NO:6. In some aspects, the present invention includes an isolated polynucleotide sequence having SEQ ID NO:2, SEQ ID NO:4, or SEQ ID NO:6. In some aspects, the present invention includes an isolated polynucleotide sequence as described herein encoding an amino acid sequence with at least one least one substitution modification relative to SEQ ID NO:2, SEQ ID NO:4, or SEQ ID NO:6.

The present invention includes an isolated polynucleotide sequence having at least about 50% sequence identity, at least about 55% sequence identity, at least about 60% sequence identity, at least about 65% sequence identity, at least about 70% sequence identity, at least about 75% sequence identity, at least about 75% sequence identity, at least about 80% sequence identity, at least about 85% sequence identity, at least about 90% sequence identity, at least about 95% sequence identity, at least about 98% sequence identity, or at least about 99% sequence identity to a nucleotide sequence encoding SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and/or SEQ ID NO:24. In some aspects, the present invention includes an isolated polynucleotide sequence having SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. In some aspects, the present invention includes an isolated polynucleotide sequence as described herein encoding an amino acid sequence with at least one least one substitution modification relative to SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

The present invention includes polynucleotide sequences that hybridize to a nucleotide sequence described herein under various conditions, and fragments thereof. Stringency conditions include, but are not limited to, moderate and high stringency. High stringency hybridization conditions may be, for example, 6×SSC, 5×Denhardt, 0.5% sodium dodecyl sulfate (SDS), and 100 ug/ml fragmented and denatured salmon sperm DNA hybridized overnight at 65° C. and washed in 2×SSC, 0.1% SDS at least one time at room temperature for about 10 minutes followed by at least one wash at 65° C. for about 15 minutes followed by at least one wash in 0.2×SSC, 0.1% SDS at room temperature for at least 3 to 5 minutes.

The present invention includes a polynucleotide sequence described herein having a substitution of one, two, three, four, five, six, seven, eight, nine, ten, eleven, twelve, thirteen, fourteen fifteen, twenty, or more nucleotides. The present invention also includes the polynucleotide sequences described herein in which codon usage has been adapted to optimize expression in a given host cell. For example, codon usage may be adapted to optimize for expression in host cells including, but not limited to, baculovirus, yeast, E. coli, poultry, or human cells. Such adaptation can be carried out by techniques know in the art.

The present invention includes primers, including, but not limited to, any of the primers described herein, and primers that can be used to generate a sequence described herein, or a fragment thereof, in a PCR reaction. In some embodiments, a primer may include at least 5, at least 10, at least 15, at least 20, at least 25, at least 30, at least 35, or at least 40 nucleotide residues. In some embodiments, a primer may include no more than 10, no more than 15, no more than 20, no more than 25, no more than 30, no more than 35, no more than 40, no more than 45, no more than 50, no more than 55, or no more than 60 nucleotide residues. Such nucleotides residues may be consecutive sequences or its complement. Also included are primer pairs including at least one of the primers described herein, complements thereof, or primers derived from such sequences. Also included in the present invention are the amplification products produced by such primers.

The present invention includes a vector including a polynucleotide sequence of the present invention. In some aspect the vector is a vaccine vector. The present invention includes an isolated polypeptide encoded by a polynucleotide of the present invention.

The present invention includes the use of one or more polynucleotide sequences of the present invention in methods of detecting an avian reovirus infectious agent in a sample. Such methods include, for example, methods that include detecting the hybridization of a polynucleotide sequence of the present invention to the sample and methods that include producing a polymerase chain reaction (PCR) amplification product with at least one primer derived from a polynucleotide sequence of the present invention. Such polynucleotide sequences include, any of those described herein, including, but not limited to SEQ ID NO:1, SEQ ID NO:3, and SEQ ID NO:5. The present invention also includes diagnostic kits including one or more of the polynucleotide sequences of the present invention. The present invention includes diagnostic kits including one or more of a virus, cell line, cell pellet, supernatant, polynucleotide sequence, vector, and/or polypeptide of the present invention.

An avian reovirus as described herein may be an inactivated or killed virus. The aim of inactivation of a virus is to prevent the viruses from replicating, and in general, this can be achieved by chemical or physical means. Chemical inactivation can be effected by treating the viruses with, for example, enzymes, formaldehyde, β-propiolactone, ethylene-imine or a derivative thereof. Physical inactivation can be carried out, for example, by subjecting the viruses to energetic radiation, such as UV light.

The present invention includes an inactivated or killed group 1 avian reovirus. In some embodiments, the present invention includes an inactivated or killed group 1 avian reovirus as shown in Table 4 or FIG. 21. In some embodiments, the present invention includes an inactivated or killed 94594 group 1 avian reovirus. In some embodiments, the present invention includes an inactivated or killed 94826 group 1 avian reovirus.

The present invention includes an inactivated or killed group 2 avian reovirus. In some embodiments, the present invention includes an inactivated or killed group 2 avian reovirus as shown in Table 4 or FIG. 21. In some embodiments, the present invention includes an inactivated or killed 96139 group 2 avian reovirus.

An avian reovirus as described herein may demonstrate reduced virulence and serve as a live attenuated virus for vaccination purposes. Attenuation of an avian reovirus useful in the practice of the present invention can be achieved by methods well known in the art for this purpose. For example, an isolated avian reovirus according to the invention can be attenuated by passage in embryonated chicken eggs, live animals or suitable cells lines. Such cell lines may include, for example, primary (avian) cell cultures, such as, for example, chicken embryo liver cells, chicken embryo fibroblasts, or chicken kidney cells, mammalian cell lines, such as, for example, the VERO cell line or the BGM-70 cell line, or avian cell lines, such as, for example, QT-35, QM-7 or LMH. Such a back passaged virus may be obtained, for example, with about 10 to about 100 passages. Such a back passaged virus may be obtained, for example, with one or more back passages, two or more back passages, three or more back passages, four or more back passages, five or more back passages, ten or more back passages, fifteen or more back passages, twenty or more back passages, twenty five or more back passages, fifty or more passages, seventy five or more passages, or one hundred or more passages. Such a back passaged virus may be obtained, for example, with about one back passages, about two back passages, about three back passages, about four back passages, about five back passages, about ten back passages, about fifteen back passages, about twenty back passages, about twenty five back passages, about fifty passages, about seventy five, about one hundred passages, or any range thereof.

For example, the present invention includes avian reoviruses attenuated by passage in embryonated chicken eggs following plaque purification. This process may be repeated, for example, about 10 (C10) to about 100 (C100) times, to attenuate the virus. Pathogenicity testing may be performed at various time points, for example, at passage 25 (C25), at passage 50 (C50), at passage 75 (C75), at passage 100 (C100), at passage 125 (C125), at passage 150 (C150), at passage 175 (C175), at passage 200 (C200), additional time points, or any range thereof. The 94826 or 94594 group 1 avian reoviruses or the 96139 group 2 avian reovirus may be passaged in such a manner.

In some embodiments, the present invention includes the 94826 group 1 avian reovirus or the 96139 group 2 avian reovirus passaged at least about 119 or more times in embryonated chicken eggs.

The present invention includes a 94826 group 1 avian reovirus has been passaged 39 times in embryonated chicken eggs (C39).

The present invention includes a 96139 group 2 avian reovirus has been passaged 31 times (C31) in embryonated chicken eggs.

An avian reovirus may be attenuated by passage in primary chicken embryo fibroblasts (CEF) following plaque purification. This process may be repeated, for example, about 10 to about 100 times, to attenuate the virus. In some embodiments, attenuation includes passage about 25 times, about 50 times, about 75 times, about 100 times or more. Pathogenicity testing may be performed at various time points, for example, at passage 25, at passage 50, at passage 75, at passage 100, and at additional time points.

In some embodiments, an avian reovirus may be attenuated by passage first in embryonated chicken eggs (for example, passaged 30, 31, 32, 33, 34, 35, 36, 37, 38, 39, 40 times, or more) followed by passage in primary chicken embryo fibroblasts (CEF) (for example, passaged 40, 41, 42, 43, 44, 45, 46, 47, 48, 49, 50, 51, 52, 53, 55, 56, 57, 58, 59, 60, or more times).

The present invention includes a 94826 group 1 avian reovirus first passaged 39 times in embryonated chicken eggs and then passaged in primary chicken embryo fibroblasts by, for example, 40, 41, 42, 43, 44, 45, 46, 47, 48, 49, 50, 51, 52, 53, 55, 56, 57, 58, 59, 60, or more times. In some embodiments, the 94826 group 1 avian reovirus has been passaged 39 times in embryonated chicken eggs (C39) and the passaged 50 times in primary chicken embryo fibroblasts (CEF 50). In some embodiments such a passaged 94826 group 1 avian reovirus has a sigma C polypeptide having at least one amino acid difference relative to SEQ ID NO:2 and/or SEQ ID NO:4.

The present invention includes a 96139 group 2 avian reovirus first passaged 31 times in embryonated chicken eggs and then passaged in primary chicken embryo fibroblasts by, for example, 40, 41, 42, 43, 44, 45, 46, 47, 48, 49, 50, 51, 52, 53, 55, 56, 57, 58, 59, 60, or more times. In some embodiments, the 96139 group 2 avian reovirus has been passaged 31 times in embryonated chicken eggs (C31) followed by passage 50 times in primary chicken embryo fibroblasts (CEF 50). In some embodiments such a passaged 96139 group 2 avian reovirus has a sigma C polypeptide having at least one amino acid difference relative to SEQ ID NO:6.

The present invention includes a method of producing an anti-group 1 and/or group 2 avian reovirus immune response in poultry, the method including administering an isolated virus, inactivated virus, killed virus, attenuated virus, cell line, cell pellet, supernatant, polynucleotide sequence, vector, and/or polypeptide of the present invention. In some aspects, immunity includes humoral and/or cellular immunity. In some aspects, immunity includes mucosal immunity.

The present invention includes a method of preventing an avian reovirus infection in poultry, the method including administering a composition including an isolated virus, inactivated virus, killed virus, attenuated virus, cell line, cell pellet, supernatant, polynucleotide sequence, vector, and/or polypeptide of the present invention.

In some aspects of the methods of the present invention, administration includes injection, spraying, oral administration, or respiratory administration. In some aspects of the methods of the present invention, administration induces mucosal immunity. In some aspects of the methods of the present invention, administration includes in ovo administration. In some aspects, in ovo administration includes administration at about 13 days, about 14 days, about 15 days, about 16 days, about 17 days, about 18 days, about 19 days, about 20 days, or any range thereof.

The present invention includes immunogenic compositions and vaccines including one or more of the isolated viruses, polynucleotide sequences, vectors, and/or polypeptides described herein. In some embodiments, the virus is live. In some embodiments, the virus is attenuated. In some embodiments, the virus is inactivated or killed. In some embodiments, the virus, compositions, or vaccine is lyophilized. In some embodiments, the virus, compositions, or vaccine is frozen.

Such a compositions and vaccine may be administered as the active component to immunize a bird to elicit an immune response to a group 1 and/or group 2 avian reovirus and/or induce immunity against such an avian reovirus. Immunity may include the induction of a higher level of protection in a population of birds after vaccination compared to an unvaccinated group. The immune response may, or may not, confer protective immunity. An immune response may, for example, include one or more of a cell mediated immune response, which involves the production of lymphocytes in response to exposure to the antigen and/or a humoral immune response, which involves production of plasma lymphocytes (B cells) in response to antigen exposure with subsequent antibody production. Immunization may result in the reduction, inhibition, or prevention of one or more of the symptoms of avian reovirus associated viral arthritis (VA)/tenosynovitis. Such symptoms may include one or more of body weight suppression, decrease in egg production, mortality, macroscopic lesions (including, but not limited to tendon swelling, tenosynovitits, tendon rupture, and hydropericardium), and histological changes (including, but not limited to lymphocytic tenosynovitis, lymphocytic epicarditis, and lymphocytic myocarditis).

An immunogenic composition or vaccine of the present invention may also include one or more compounds with adjuvant activity. Suitable compounds or compositions for this purpose include aluminum hydroxide, aluminum phosphate, aluminum oxide, plant oils, animal oils, oil-in-water or water-in-oil emulsion based on, for example a mineral oil, such as Bayol F™ or Marcol 52™, Complete Freund's adjuvant, incomplete Freund's adjuvant, or a vegetable oil such as vitamin E acetate, and saponins.

An immunogenic composition or vaccine of the present invention may include one or more suitable pharmaceutically acceptable carriers or diluents. An immunogenic composition or vaccine of the present invention may also contain one or more stabilizers. Any suitable stabilizer can be used including carbohydrates such as sorbitol, mannitol, starch, sucrose, dextrin, or glucose; proteins such as albumin or casein; and buffers such as alkaline metal phosphate and the like. A stabilizer is particularly advantageous when a dry vaccine preparation is prepared by lyophilization.

An immunogenic composition or vaccine of the present invention may further include one or more immunogens derived from other pathogens infectious to poultry. Such immunogens may be derived from, for example, Marek's disease virus (MDV), infectious bronchitis virus (IBV), Newcastle disease virus (NDV), egg drop syndrome (EDS) virus, turkey rhinotracheitis virus (TRTV), poxvirus, reovirus, chicken parvovirus, and avian nephritis virus (including, but not limited to ANV-1 and ANV-2).

An immunogenic composition or vaccine of the present invention may be administered by any suitable known method of inoculating poultry including nasally, ophthalmically, by injection, in drinking water, in the feed, by exposure, in ovo, maternally, by respiratory inhalation, and the like. The immunogenic composition or vaccine may be administered by mass administration techniques such as by placing the vaccine in drinking water or by spraying the environment. When administered by injection, the immunogenic composition or vaccine may be administered parenterally. Parenteral administration includes, for example, administration by intravenous, subcutaneous, intramuscular, or intraperitoneal injection.

In some embodiments, a live vaccine may be administered in a dose of not less than $10^2$ titration units (wherein titration units are defined in Title 9, Section 113.332, Code of Federal Regulations) per bird, and an inactivated vaccine may contain the antigenic equivalent of $10^4$-$10^{10}$ TCID$_{50}$ per bird (wherein TCID is an abbreviation for Tissue Culture Infective Dose).

Compositions and vaccines of the present invention may be substantially pure. As used herein, "substantially pure" will mean material essentially free of any similar macromolecules or other biological entities that would normally be found with it in nature.

Compositions and vaccines of the present invention may be administered to birds of any of a variety of avian species that are susceptible to infection with an avian reovirus, including, but not limited to, poultry, birds of the order Galliformes, and exotic bird species. Birds of the order Galliformes include, but are not limited to, chickens, turkeys, grouse, quails, and pheasants. As used herein, poultry includes domesticated birds that are kept for the purpose of collecting their eggs, or killing for their meat and/or feathers. These most typically are members of the superorder Galloanserae (fowl), especially the order Galliformes (which includes, for example, chickens, quail, turkeys, and grouse) and the family Anatidae (in order Anseriformes), commonly known as "waterfowl" (including, for example, ducks, geese, and swans). Poultry may also include other birds which are killed for their meat, such as pigeons or doves or birds considered to be game, like pheasants. Chickens include, but are not limited to, hens, roosters, broilers, roasters, layers, breeders, the offspring of breeder hens, and layers. As used herein, the term "susceptible to" means the possibility or actuality of a detrimental response to the referenced microorganism, such as, for example, reduced vigor or a failure to thrive, when compared to a non-susceptible individuals or groups, and/or one or more pathological state(s) indicative of avian virus infection.

The vaccine of the present invention may be administered to poultry before or after hatching. Poultry may receive a vaccine at a variety of ages. For example, broilers may be vaccinated in ovo, at one-day-old, or at 2-3 weeks of age. Laying stock or reproduction stock may be vaccinated, for example, at about 6-12 weeks of age and boosted at about 16-20 weeks of age. Such laying stock or reproduction stock may be vaccinated at about 6, at about 7, at about 8, at about 9, at about 10, at about 11, or at about 12 weeks of age. Such laying stock or reproduction stock may be boosted at about 16, at about 17, at about 18, at about 19, or at about 20 weeks of age. The offspring of such laying stock or reproduction stock may demonstrate an antibody titer to a polypeptide as described herein, which may prevent or mitigate the symptoms of an avian reovirus infection in the offspring. In ovo vaccination may take place, for example, at about 13 days, about 14 days, about 15 days, about 16 days, about 17 days, about 18 days, about 19 days, about 20 days, or at any range thereof.

Chickens may be vaccinated at any suitable age, and are usually about one to three days old before first vaccination. The chickens may be vaccinated only once. Or, if two doses of vaccine are used, the first is given, for example, when the chickens are 3 days to a week old and subsequently after a further 1-10 weeks.

Multiple doses of the composition can be administered throughout the life of the chicken. As maternal immunity is a primary source of providing protection to broiler progeny, breeder chickens are typically vaccinated, although broiler chickens can be vaccinated if so desired.

Also included in the present invention are antisera and antibodies that bind to a group 1 avian reovirus and/or a group 2 avian reovirus. In some aspects, an antisera or antibody does not to the current commercial vaccine strains of avian reovirus, such as, for example, avian reovirus strain S1133, 1733, 2408, and/or 2177. Antibodies useful in the practice of the present invention include monoclonal antibodies, polyclonal antibodies, single chain antibodies, humanized antibodies, chimeric antibodies, or fragment thereof, also including bispecific antibody, synthetic antibody, antibody fragment, such as Fab, Fv, F(ab)2, or scFv fragments, single chain antibodies, or a chemically modified derivative of any of these. Such antibodies may be used in diagnostic methods and diagnostic kits. In some aspects, an anti-avian reovirus antibody may be attached to a solid substrate.

Also included in the present invention are hyperimmune antisera that bind to a group 1 avian reovirus and/or a group 2 avian reovirus. In some embodiments, the hyperimmune antisera binds to the 94826 group 1 avian reovirus. In some embodiments, the hyperimmune antisera binds to the 96139 group 2 avian reovirus. In some embodiments, the hyperimmune antisera is produced by first immunizing chickens with whole, live virus, for example by eye drop application, followed by one or more immunizations with inactivated virus, for example by intramuscular injection in an oil adjuvant. Such hyperimmune serum may be used, for example, as positive control serum samples in diagnostic assays, such as, for example, a virus neutralization assay with plague purified virus, to determine if birds have been vaccinated or exposed to a Group 1 or Group 2 avian reovirus isolate.

The present invention provides methods for detecting and/or measuring the amount of a group 1 avian reovirus in a sample obtained from a bird. In some aspects, a group 1 avian reovirus includes a sigma C protein with an amino acid sequence as described herein, including, but not limited to a sigma C protein having SEQ ID NO:2 or SEQ ID NO:4, or a fragment or derivative thereof. In some aspects, a group 1 avian reovirus includes a sigma C protein with an amino acid sequence as described herein, including, but not limited to a sigma C protein having SEQ ID NO:13, SEQ ID NO:14, SEQ ID NO:15, SEQ ID NO:16, SEQ ID NO:17, SEQ ID NO:18, SEQ ID NO:19, or SEQ ID NO:20, or a fragment or derivative thereof.

The present invention provides methods for detecting and/or measuring the amount of a group 2 avian reovirus in a sample obtained from a bird. In some aspects, a group 2 avian reovirus includes a sigma C protein with an amino acid sequence as described herein, including, but not limited to a sigma C protein having SEQ ID NO:6, or a fragment or derivative thereof. In some aspects, a group 2 avian reovirus includes a sigma C protein with an amino acid sequence as described herein, including, but not limited to a sigma C protein having SEQ ID NO:21, SEQ ID NO:22, SEQ ID NO:23, or SEQ ID NO:24, or a fragment or derivative thereof.

Such a method may include contacting a sample with an antibody that selectively binds to an avian reovirus as described herein and/or a sigma C protein as described herein and measuring the amount of binding of the antibody to a virus or protein in the sample. The sample may be any biological material, such as tissue, bone, blood, urine or faeces. The methods of this aspect of the invention are useful, for example, for determining whether poultry are infected with an avian reovirus of the present invention. Infected animals can be killed in order to prevent spread of the reovirus to other animals.

As used herein, "isolated" refers to material removed from its original environment (e.g., the natural environment if it is naturally occurring), and thus is altered "by the hand of man" from its natural state.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

In several places throughout the application, guidance is provided through lists of examples, which examples can be used in various combinations. In each instance, the recited list serves only as a representative group and should not be interpreted as an exclusive list. It is to be understood that the particular examples, materials, amounts, and procedures are to be interpreted broadly in accordance with the scope and spirit of the invention as set forth herein.

The present invention is illustrated by the following examples. It is to be understood that the particular examples, materials, amounts, and procedures are to be interpreted broadly in accordance with the scope and spirit of the invention as set forth herein.

EXAMPLES

Example 1

Isolation and Characterization of Variant Reoviruses

This example describes the isolation of variant reoviruses from tendons in numerous clinical cases of tenosynovitis and/or lameness in broilers, ranging in age from 2.5-8 weeks submitted to the Poultry Diagnostic and Research Center. The avian reoviruses were characterized by sequencing the sigma C protein and serologic assays.

Materials and Methods

Virus Isolation. Reovirus field isolates Ck/94594 Tendon/GA/2012, Ck/94826 Tendon/GA/2012 and Ck/96139 Tendon/GA/2012 were isolated at the Poultry Diagnostic and Research Center at the University of Georgia, from the tendons of commercial broilers exhibiting clinical signs of viral arthritis and tenosynovitis. Tendons and synovial aspirates from clinically affected chickens were individually homogenized in virus transport media with antibiotics. The homogenized tissues were filtered through a 0.45 micron syringe filter. The filtrates were incubated with Reovirus S1133 antisera (Charles River, SPAFAS, Wilmington, Mass.) at 37° C. for 1 hour. Following neutralization, 0.2 ml homogenate was inoculated in primary chicken embryo liver cells for a total of four passages. Upon the development of 70-80% cytopathic effect, observed as syncytial formation, the cell cultures were frozen and stored at −80° C. Cell cultures were frozen and thawed three times prior to subsequent cell culture passage.

RNA extraction. Total viral RNA was extracted from primary chicken embryo liver cell passages using the RNeasy kit (Qiagen, Valencia, Calif.) according to the manufacturer's recommendations. Briefly, 48 hours post infection, cell culture media was decanted, the monolayer overlaid with 300 µl RLT buffer containing 0.143 M β-mercaptoethanol and scraped with a cell scraper as recommended by the manufacturer.

RT-PCR. A cDNA corresponding to the S1 gene was produced by reverse transcription and PCR using SUPER-SRIPT™ III RNase H-reverse transcriptase and PLATINUM®Taq DNA polymerase (Invitrogen, Carlsbad, Calif.) with previously published P1 (AGTATTTGTGAG-TACG ATTG (SEQ ID NO:7)) and P4 (GGCGCCACAC-CTTAGGT (SEQ ID NO:8)) primers (Kant et al., 2003, Vet Res; 34:203-212). The 1.1 kb amplified products were separated on a 1.0% agarose gel, stained with ethidium bromide and visualized with a UV transilluminator. The fragment was excised, purified with the QIAEX II gel extraction kit (Qiagen Inc., Valencia, Calif.), eluted in diethylpyrocarbonate (DEPC)-treated water, and stored at −80° C.

Nucleotide sequencing of amplified products and S1 clones. Gel-purified PCR products were sequenced directly using double-stranded DNA sequencing with fluorescently-labeled dideoxynucleotides and Taq polymerase and performed on an ABI 9700 automated sequencer (Applied Biosystems Inc., Foster City, Calif.). PCR primers P1 and P4 were used to sequence, as well as, conserved internal S1 gene primers as needed to complete sequencing. Primer sequences used for sequencing are available upon request. In addition, gel purified products were cloned into plasmid pCR2TOPO (Invitrogen) and transformed into *E. coli* according to the manufacturers recommendations. Several clones from each isolate containing plasmids with the 1.1 kb insert were identified by PCR using M13 forward and reverse primers. The clones were expanded and the plasmid purified using a plasmid miniprep kit (Qiagen, Valencia, Calif.) according to methods of the manufacturer. M13 universal forward and reverse primers were used for sequencing along with internal S1 primers as needed to complete sequencing. At least three clones or PCR products from three amplifications containing the S1 gene were sequenced in both directions and used to obtain the consensus. Nucleotide and amino acid sequences for isolates 94594, 94826 and 96139 are identified in FIGS. 1-6.

Sequence analysis. Nucleotide, predicted amino acid sequence analysis and multiple alignments of the S1 gene and sigma C protein were performed using CLUSTAL W (Lasergene, v. 5.0, DNASTAR, Madison, Wis.). Sequences for the S1 genes of previously published avian reoviruses were obtained from GenBank.

Aligned sequences were compared and a phylogenetic tree was generated using Neighbor-Joining clustering and 1000 bootstrap replicates (confidence levels listed in parentheses) in a heuristic search using the Phylogenetic Analysis Using Parsimony v 4.10b software (PAUP).

GenBank Accession Numbers. Sequences obtained for chicken isolates 94594, 94826 and 96139 have been submitted to GenBank and assigned the following accession numbers: KJ803966, KJ803967, and KJ803990, respectively.

Results and Discussion

Figure 8:
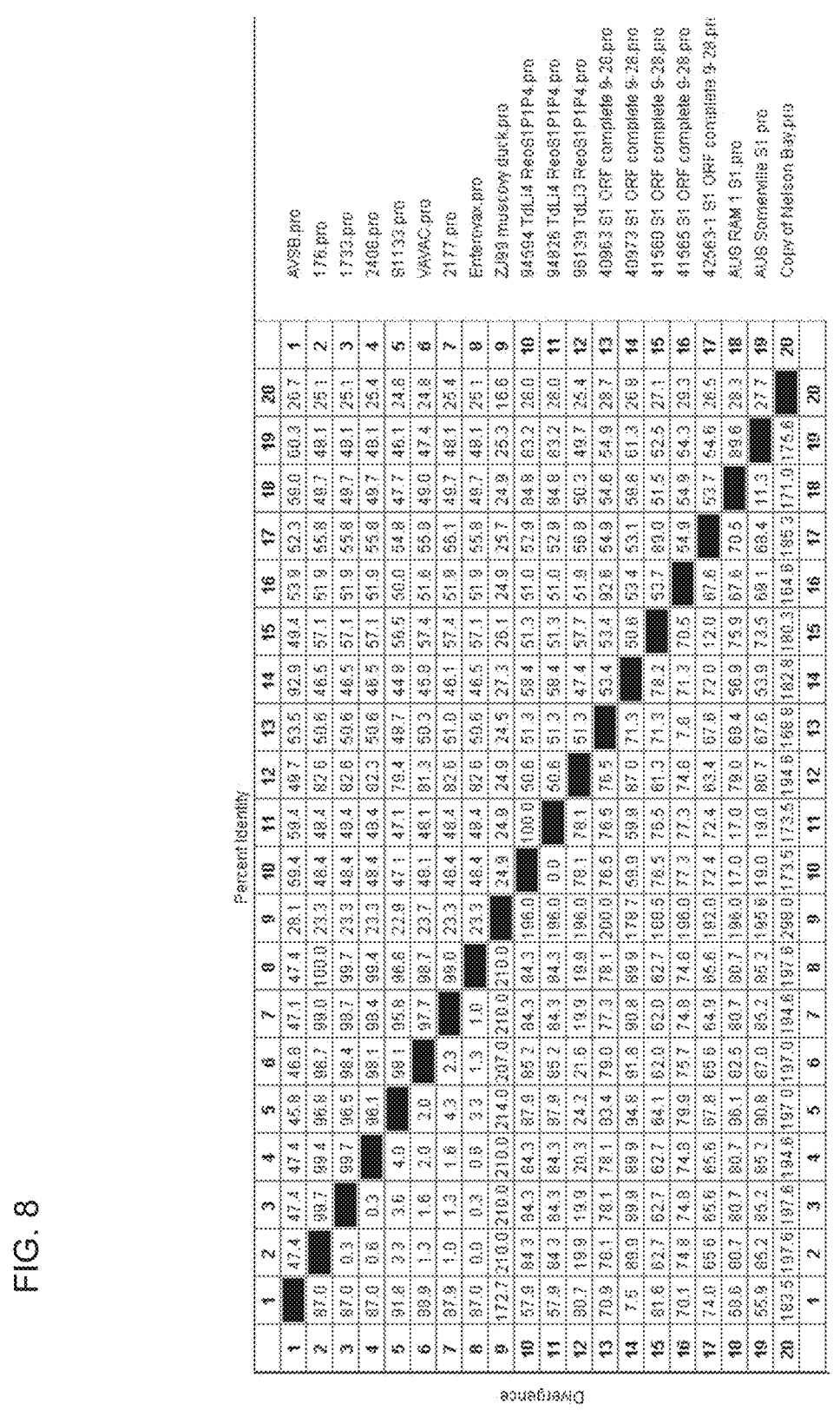

To date, two primary variant genotypes of reovirus field isolates have emerged from the clinical cases of VA/tenosynovitis and are characterized as variant genotypes due to the lack of similarity with current reovirus vaccine strains (S1133, 1733, 2408, 2177) and other viruses in the databases (FIG. 7). The majority of field isolates belong to group 1 (identified as group 1 2012 VA variants). The sigma C amino acid sequences of reoviruses belonging to this genotype are >99% similar to each other and <50% similar to vaccine strains when compared to sequences in the public domain and PDRC database (FIG. 8). Reoviruses in group 2 (identified as group 2 2012 VA variants) are >99% similar to each other and <50% similar to the group 1 2012 VA variants (FIG. 8). The sigma C similarity between group 2 2012 VA variants and vaccine strains is 80% (FIG. 8). Although this group shares a higher sequence similarity, it was not clear whether the 80% similarity would translate into some level of cross protection with current vaccine strains. Serological evaluation of field isolates from both groups was performed to provide necessary information on the serological relatedness of the viruses.

Representative viruses from group 1 and 2 variants were evaluated in a one-way cross neutralization assay using antisera to S1133, 2408 and a hyper-immune serum prepared against a group 1 2012 VA variant. VN titers between the field isolates and the serum panel were between 2 and 16, providing evidence that the field isolates are not serologically related to S1133, 2408 or each other.

Example 2

Pathogenicity and Progeny Protection Studies for Group 1 Variant Reovirus

This example determined the pathogenicity of the reovirus variant group 1 2012 VA isolates 94826 and 94594 in chickens.

Experiment #1

This experiment was to determine if Company A's breeder vaccination program provides adequate protection against variant group 1 2012 VA isolate in progeny challenged with reovirus field isolate 94826.

Chickens. 80 1-day-old commercial broilers from Company A's vaccinated breeders were used.

TABLE 1

Treatment groups

| No. of chicks | Group ID | Group Treatment |
|---|---|---|
| 20 chicks | 1 | Bled for Reovirus ELISA (IDEXX) |
| 20 chicks | 2 | Inoculated with S1133 |
| 20 chicks | 3 | Inoculated with isolate 94826 |
| 20 chicks | 4 | Inoculated with sterile PBS |

Virus. Field isolate 94826 was propagated and titrated in primary chicken embryo liver cells and was used for foot pad inoculation of day-old chicks at a challenge dose of $10^3$ TCID50/bird. S1133 stock also titrated in primary chicken embryo liver cells will be used for foot pad inoculation of day-old chicks at a dose of $10^3$ TCID50/bird. Negative controls will be mock challenged via foot pad with sterile PBS.

Reovirus challenge. Sixty commercial broilers were received at day-of-hatch and divided into 3 groups of 20 and placed into Horsfall Bauer isolation units. Chicks from group 1 were bled for reovirus ELISA (IDEXX) and terminated. Chicks from Groups 2-4 were inoculated via the footpad with 1) sterile PBS, 2) S1133, or 3) 94826. This is detailed in Table 1. Birds were observed daily and hock swelling was measured with digital calipers in each treatment group and recorded every 2 days. On day 14, all birds were euthanized, weighed and necropsied. Birds were examined for any macroscopic lesions and hock joints were examined for swelling, hemorrhage and/or rupture. Parameters for protection included day-of-hatch serology, clinical signs, mortality, body weight, macroscopic lesions and evaluation/measurement of hock swelling throughout study.

Experiment #2

This experiment was to determine if Company B's breeder vaccination program provides adequate protection against viral arthritis in progeny challenged with a recent Company B farm's reovirus field isolate and whether or not use of a commercial reovirus vaccine at day-of-age provides any protection.

Chickens. 100 1-day-old commercial broilers from Company B vaccinated breeders were used.

TABLE 2

Treatment Groups

| No. of chicks | Group ID | Group Treatment |
|---|---|---|
| 20 chicks | 1 | Bled for Reovirus ELISA (IDEXX) |
| 20 chicks | 2 | Inoculate with sterile PBS |
| 20 chicks | 3 | VA ChickVac full dose at 1 d then challenge w/94594 |
| 20 chicks | 4 | VA ChickVac ½ dose at 1 d then challenge w/94594 |
| 20 chicks | 5 | Challenge with Sanderson field isolate 94594 |

Virus. The reovirus field isolate 94594 was propagated and titrated in primary chicken embryo liver cells prior to the study. VA ChickVac (Zoetis) was used for day-of-hatch vaccination per manufacturer's recommendations. Negative controls were mock challenged with sterile PBS.

Reovirus challenge. One hundred commercial chicks were received at day-of-hatch and divided into 5 equal groups of 20 chicks each. Group 1 was bled for reovirus ELISA (IDEXX). The remaining 4 groups of chicks were placed into Horsfall Bauer isolation units under forced air positive pressure. On the day-of-hatch, Group 3 was vaccinated with VA ChickVac at full dose by subcutaneous administration while Group 4 was vaccinated with VA ChickVac at half dose by subcutaneous administration. This is detailed in Table 2. On day 10, footpad measurements were obtained for all chicks. On day 10, Group 2 was inoculated via footpad with 0.1 ml sterile phosphate buffered saline while chicks in Groups 3-5 were challenged via footpad inoculation with field isolate 94594 at $10^3$ TCID50 per bird. Birds were monitored daily and measurements of hocks were obtained every 2 days starting at 10 days of age. At 22 days of age, the study was terminated. Parameters used for protection were day-of-hatch serology, clinical signs, mortality, body weight, macroscopic lesions.

Results and Discussion

Figure 9:
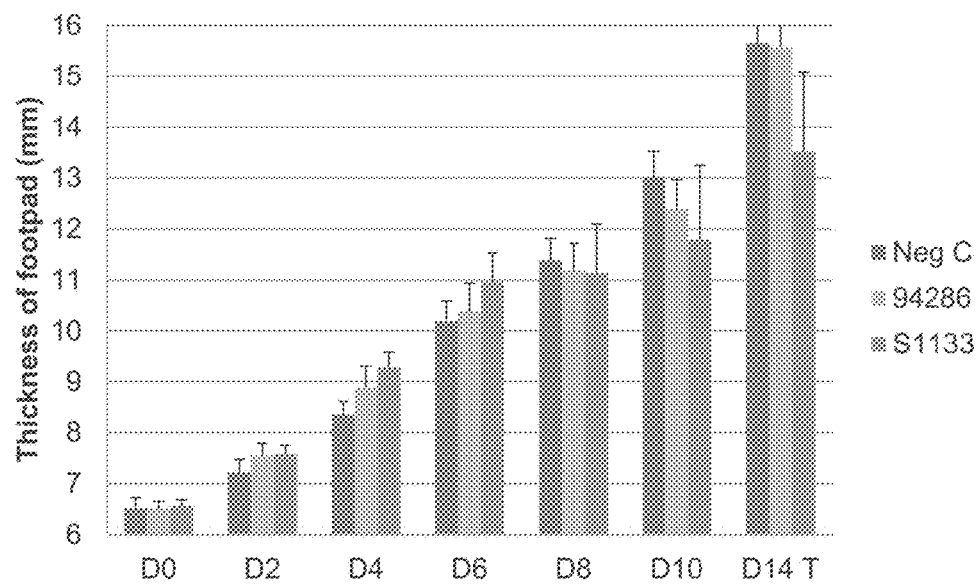
FIG. 9. Mean footpad measurement in millimeters at days indicated on the X axis. Starting at seven days of age, a noticeable difference was observed in the size of birds in the S1133 and 94286 challenged groups compared to the negative controls. Standard deviation indicated by bars for each group.
Figure 10:
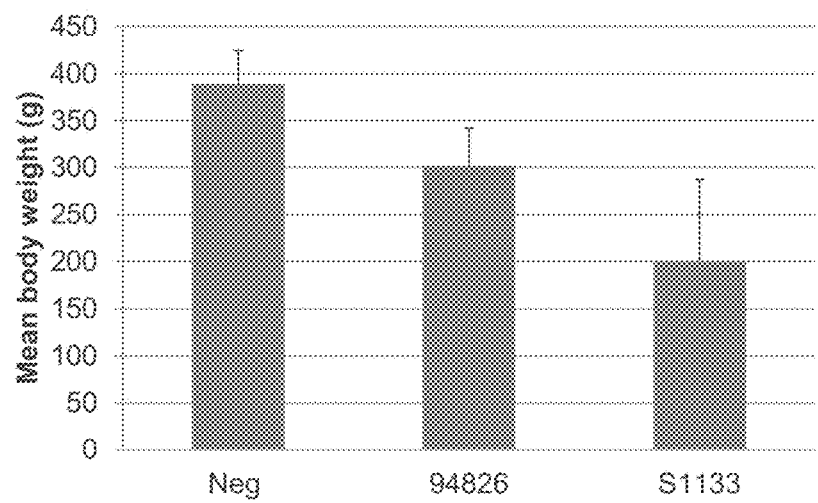
FIG. 10. Mean body weights at day of termination (14 days of age). Standard deviation indicated by bars for each group.
Figure 11:
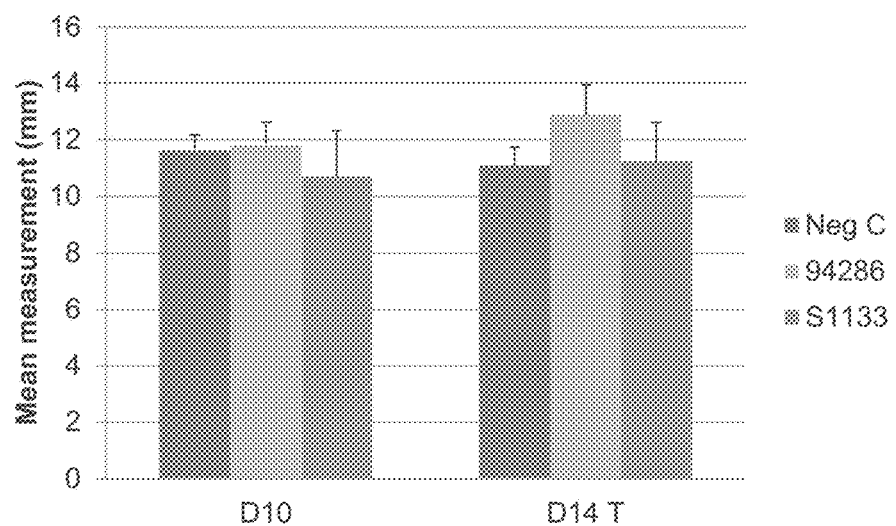
FIG. 11. Measurements were taken over the digital flexor tendon, just below the hock joint, at 10 days of age and again on the day of termination, 14 days of age. Obvious swelling was observed in the 94286 challenged group at 14 days. Standard deviation indicated by bars for each group.
Figure 12:
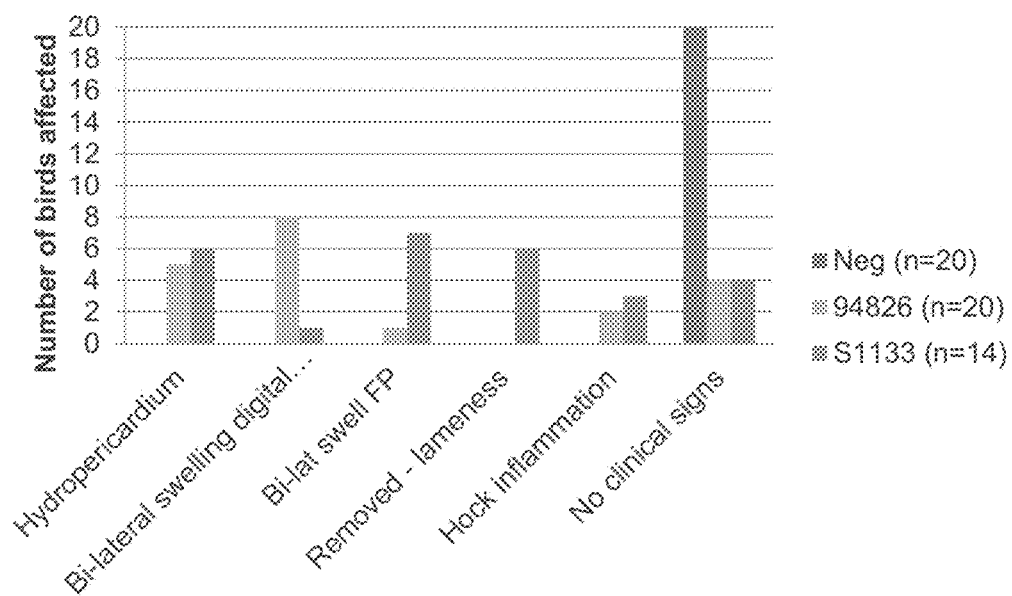
FIG. 12. Clinical signs recorded on the day of termination. Note that 6 birds were removed on day 10 from the S1133 group due to lameness and inability to get to feed or water.

Pathogenicity and progeny protection studies were performed in commercial broilers using representative strains from the group 1 2012 VA variant genotype. In the first study, day-of-hatch chicks were challenged by foot pad with either S1133 or a group 1 2012 VA variant isolate and one group was placed for negative controls. In addition, a separate group of twenty day-of-hatch chicks were bled for reovirus ELISA. All chicks were placed in floor pens in separate isolation houses on fresh shavings and given free access to feed and water. Footpad measurements were taken every 2 days and birds were monitored daily for clinical signs up to the termination of the experiment on day 14 (FIG. 9). The Reovirus ELISA geometric mean titer (GMT) for the flock was 1,212, which is considered low for day-of-hatch chicks. Clinical tenosynovitis and significant body weight suppression was observed in both the S1133 and variant reovirus challenged groups (FIGS. 10 and 12). While S1133 chicks were more severely affected by lameness than those challenged with the variant, there was a higher incidence of swelling around the digital flexor tendon in the variant challenged group (FIG. 11). Other clinical signs observed in the challenged groups included hydropericardium and hock inflammation (FIG. 12). The reovirus day-of-hatch titers were low and thus the maternal derived antibodies from Company A's vaccination program did not provide sufficient protection against challenge with the Group 1 variants. In addition, the field isolate reproduced the clinical disease observed in the field and was confirmed as the causative agent of disease.

Figure 13:
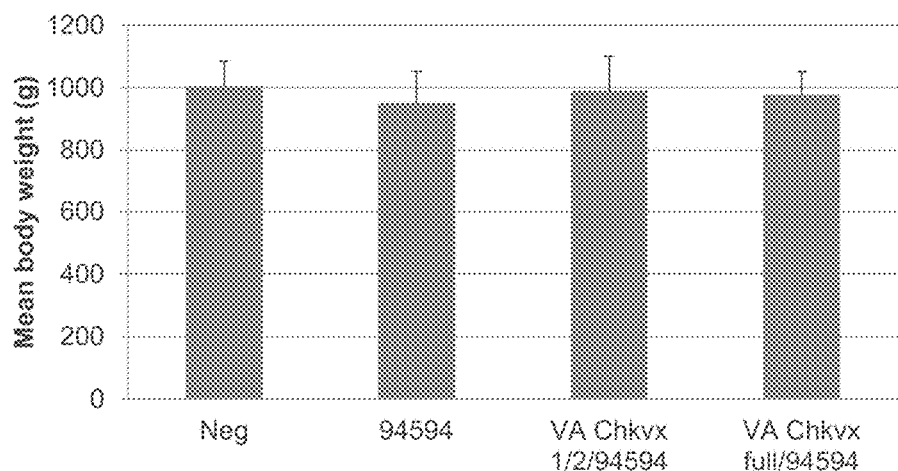
FIG. 13. Mean body weight in grams at termination of the study (23 days of age). Standard deviation is represented by the capped line.
Figure 14:
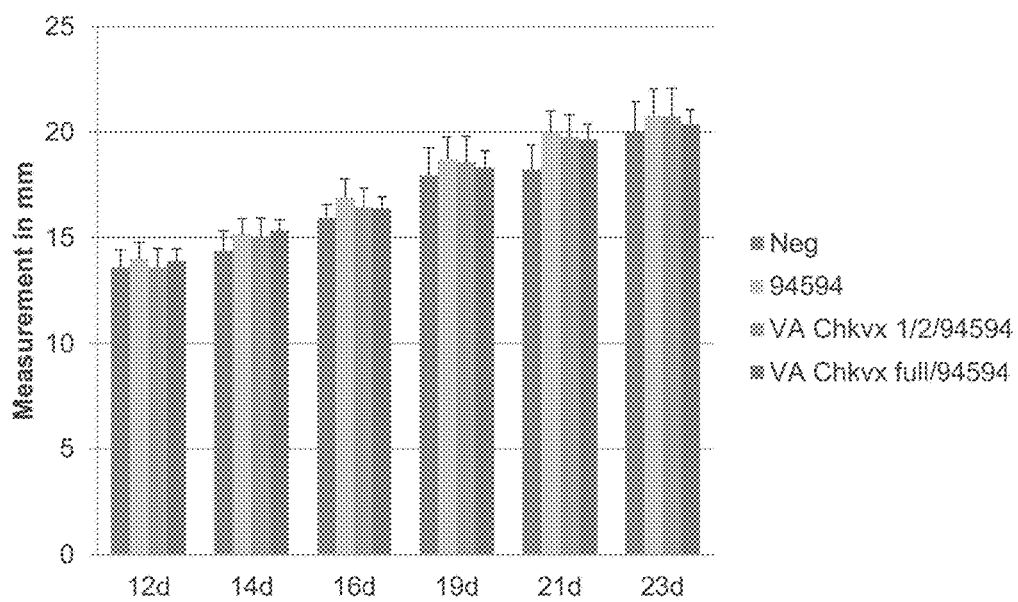
FIG. 14. Mean footpad measurements in millimeters taken at 12, 14, 16, 19, 21, and 23 days of age. The first measurement was taken at 12 days of age, just prior to challenge.
Figure 15:
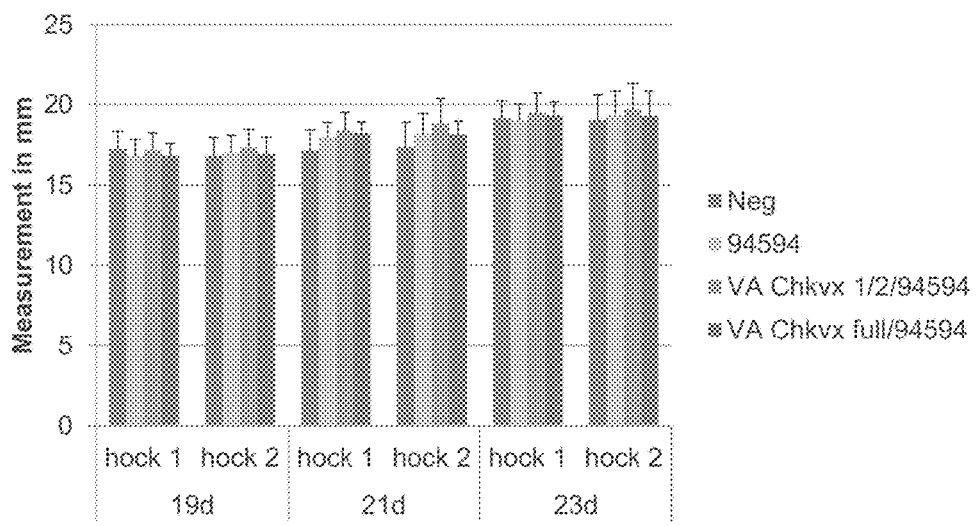
FIG. 15. Mean hock measurements in millimeters taken at 19, 21, and 23 days of age. The hock 1 measurement was taken at the hock joint and the hock 2 measurement was taken over the digital flexor tendon just below the hock joint.
Figure 16:
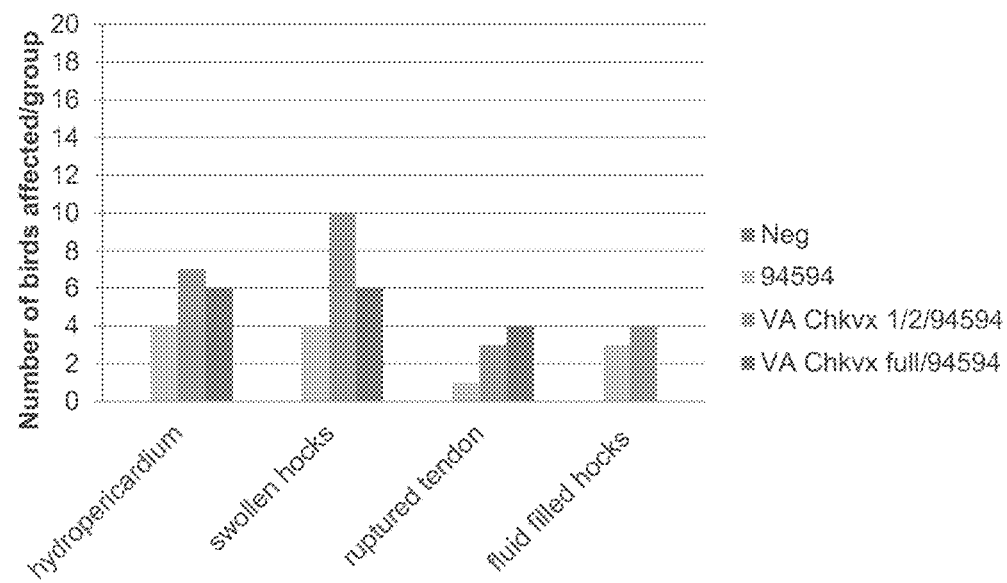
FIG. 16. Clinical signs and lesions at day of termination (23 days).
Figure 17:
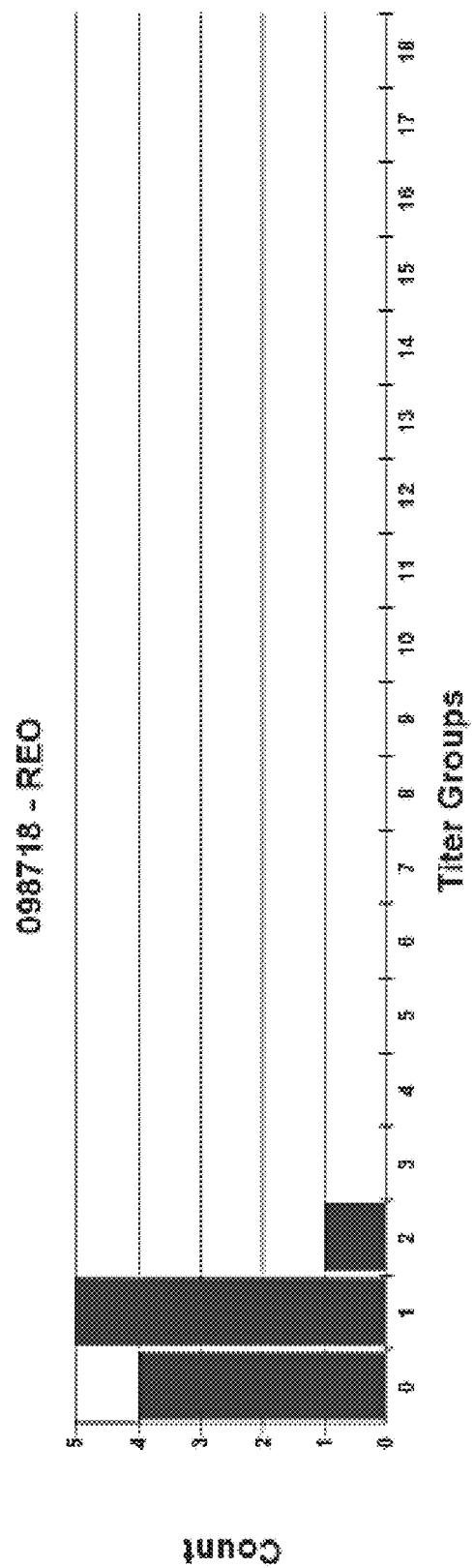
FIG. 17. Day of hatch serology.

In the second study, commercial broiler chicks were challenged with a Group 1 variant at 12 days-of-age by footpad and the study was terminated at 23 days of age. The reovirus ELISA GMT obtained from serum collected at day-of-hatch was 4,900. In this study, mean body weights were only slightly lower in the challenged group compared to the negative controls (FIG. 13). However, the challenged group showed clinical signs and macroscopic lesions characteristic of viral arthritis/tenosynovitis (FIG. 14). As in the first study, swelling around the digital flexor tendon as well as hydropericardium was observed in the challenged birds (FIGS. 12 and 13). From this study, one can conclude that chicks with higher levels of maternal derived reovirus antibodies were not protected against challenge with a group 1 variant.

In addition, the use of a commercial reovirus vaccine administered subcutaneously at full dose and half dose in day-of-hatch commercial broilers followed by challenge with a Group 1 variant at 12 days of age was evaluated. Using the same parameters as in the previous studies, we observed clinical signs and macroscopic lesions characteristic of VA/tenosynovitis in all challenged groups. Interestingly, the incidence of hydropericardium and swollen hocks was higher in the groups that were vaccinated and challenged, regardless of the dosage, compared to the challenge only group (FIG. 14).

In summary, variant reoviruses have been isolated from clinical cases of viral arthritis/tenosynovitis and are genetically and antigenically distinct from current reovirus vaccine strains. Two distinct groups have been identified as Group 1 and Group 2 2012 variant VA reoviruses based on genetic and serologic characterization. In vivo studies suggest that current commercial vaccines do not provide protection against challenge with Group 1 2012 variants in chicks with maternal derived reovirus antibodies. In vivo studies with a representative Group 2 isolate are given below, in Example 3. Group 1 and 2 variant reoviruses have been isolated or detected from clinical cases of tenosynovitis from numerous states within the US and from Canada with the number of isolates belonging to Group 1 exceeding that of Group 2. The origin of these viruses is not known.

Example 3

Pathogenicity Studies for Group 2 Variant Reovirus

Procedures described in more detail in Example 2 were used to characterize the pathogenicity of a Group 2 variant reovirus in commercial broilers. A representative strain from the Group 2 2012 VA variant genotype was used (Ck/96139 Tendon/GA/2012). The treatment groups are as described in Table 3.

TABLE 3

| Treatment groups | |
| --- | --- |
| Groups | Treatment |
| 10 1-day old commercial broilers | Bled for Reovirus ELISA (IDEXX) |
| 10 1-day old commercial broilers | Inoculated with Group 2 Variant |
| 10 1-day old commercial broilers | Inoculated with sterile PBS |

Chicks were inoculated via footpad with 0.1 ml sterile phosphate buffered saline or field isolate 996139 at $10^3$ TCID50 per bird. Parameters used for protection were day-of-hatch serology, clinical signs, mortality, body weight, and macroscopic lesions. Foot pad swelling and tendon swelling were evaluated and measured throughout the study.

Results and Discussion

Day of hatch serology by Reovirus ELISA (IDEXX) is shown in Figured 17. Specifically, the mean is 511, the GMT is 385, the SD is 343, and the % CV is 66.8%.

Figure 18:
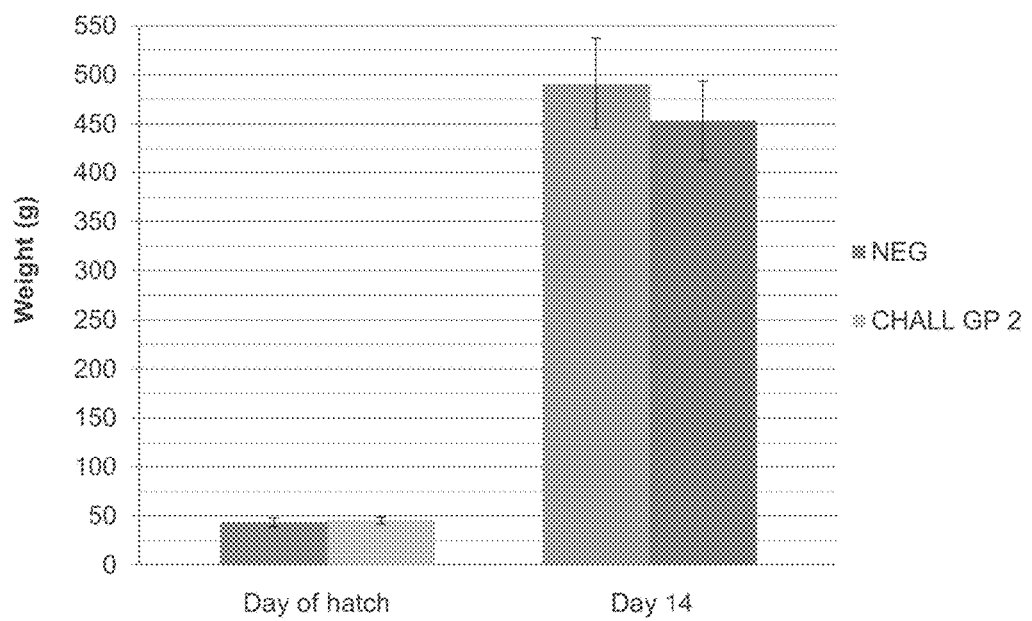
FIG. 18. Body weights in Group 2 challenged birds.

As shown in FIG. 18, Group 2 challenge decreases body weight. Specifically, a 8% body weight suppression was observed in Group 2 challenged birds.

Figure 19:
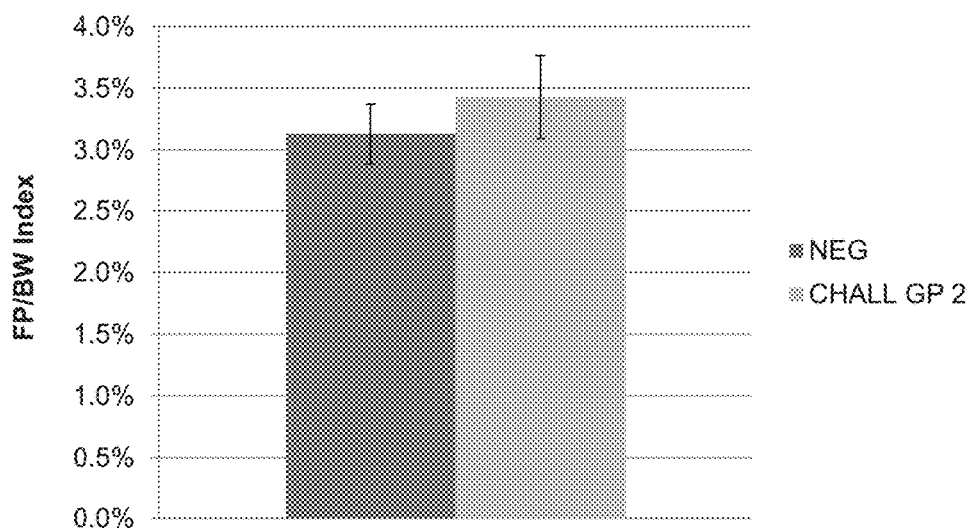
FIG. 19. Day 14 measurement of footpad swelling as a percentage of body weight for Group 2 challenged birds.
Figure 20:
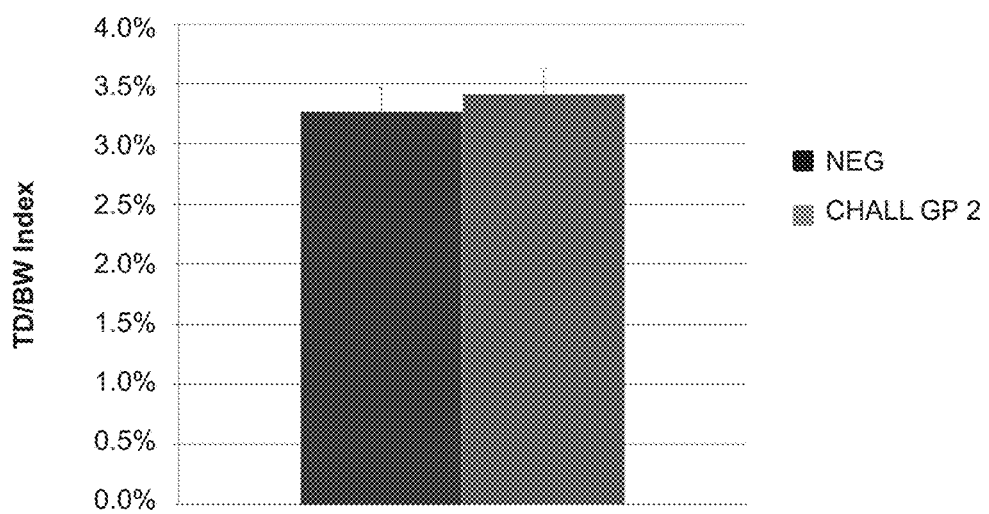
FIG. 20. Measurement of tendon swelling as a percentage of body weight for Group 2 challenged birds.

FIG. 19 shows day 14 measurements of footpad swelling as a percentage of body weight while FIG. 20 shows measurements of tendon swelling as a percentage of body weight for Group 2 challenged birds.

Necropsy and histological findings for Group 2 challenged birds are as follows: 2/10 birds with ruptured tendons; 5/10 birds with lymphocytic tenosynovitis (tendon sheath); 2/10 birds with hydropericardium; and 2/10 birds with lymphocytic epicarditis and myocarditis. No significant lesions were observed in the liver or duodenum.

Thus, Group 2 challenge resulted in subtle weight suppression. Hydropericardium, swollen tendons, and a few ruptured tendons were observed in Group 2 challenged birds. And, histological lesions consistent with reovirus were observed in the heart and tendons.

In conclusion, both Group 1 and Group 2 variants are isolated from clinical cases of viral arthritis in commercial broilers. Both Group 1 and Group 2 variants reproduce tenosynovitis, including hydropericardium and tendon swelling observed grossly and histological changes consistent with reovirus were observed in hearts and tendons. Group 1 variants are more prevalent. Current commercial vaccines do not appear to provide adequate protection in broilers. Thus, an autogenous vaccination appears to be the only current option for control.

Example 4

Plaque Assay for Avian Reovirus

Seeding Chicken Embryo Liver cells in 35 mm plate:
  Previous day before doing the assay, add Chicken Embryo Liver Cells (CELiC) in 35 petri dishes (2 ml/petri dish).
  Place the 35 mm plates in the incubator at 37° C. (overnight, at least more than 12 hours).
Procedure for Plaque Assay:
  Remove the medium (M199/F10+10% FBS) from the confluent CELiCs.
  Add 200 µl of the virus ($10^2$ $TCID_{50}$) to the plate.
  Thirty minutes later, add 2 ml of M199/F10+2% CS with diluted virus to the plate and swirl the plate gently.
  Incubate the plate for 3-4 hours at 37° C.
  During that time prepare 2 ml per plate: 1 ml (2× concentration of M199/F10+5% CS)+ and 1 ml of 3% SeaPlaque Agarose in cell culture grade $H_2O$.
  After 3-4 hours take the plate from the incubator and remove the supernatant (1,200 µl).
  Now 2 ml/well of the prepared overlay, and incubate for 2-3 days at 37° C.
Staining after 2-3 days (Generally try to stain 2 days after inoculation, if more than 3 days cells will start to die and the plaques may not be good):
  Prepare 10% filtered Neutral red diluted in cell culture grade water.
  Add 1 ml/plate.
  Incubate for at least 2 hours (2-4 hours) in the incubator.
  After couple of hours, the plaques will appear clearly.
Results: Live cells will stain red. Plaques will remain unstained.

Example 5

Group I and Group 2 Sigma C Protein Sequences

Following procedures described in more detail in Example 1, the nucleotide sequences encoding the sigma C protein and the encoded sigma C amino acid sequences of 122 Group 1 and Group 2 variant avian reoviruses were determined. Table 4 below shows the GenBank Accession Number, Sequence ID, isolate designation, and tissue type from which viruses was isolated, collection date, state and country of isolation, and isolation source for the 122 isolates. Chicken embryo liver cells serve as a lab host for all 122 isolates.

TABLE 4

Group 1 and Group 2 Avian Reoviruses

| Accession No. | Sequence ID | Isolate | Tissue type | Collection Date | Country | Isolation source |
|---|---|---|---|---|---|---|
| KJ803958* | GA_91955Td_2011 | 91955 | Tendon | 8-Dec-2011 | USA: GA | Broiler |
| KJ803959* | GA_92715Td_2012 | 92715 | Tendon | 9-Feb-2012 | USA: GA | Broiler |
| KJ803962* | GA_93116Td_2012 | 93116 | Tendon | 5-Mar-2012 | USA: GA | Broiler |
| KJ803963* | GA_93117Td_2012 | 93117 | Tendon | 5-Mar-2012 | USA: GA | Broiler |
| KJ803964* | GA_94592Td_2012 | 94592 | Tendon | 7-Jun-2012 | USA: GA | Broiler |
| KJ803965* | GA_94593Td_2012 | 94593 | Tendon | 7-Jun-2012 | USA: GA | Broiler |
| KJ803966* | GA_94594Td_2012 | 94594 | Tendon | 7-Jun-2012 | USA: GA | Broiler |
| KJ803967* | GA_94826Td_2012 | 94826 | Tendon | 15-Jun-2012 | USA: GA | Broiler |
| KJ803968* | AR_95212Td_2012 | 95212 | Tendon | 26-Jul-2012 | USA: AR | Broiler |
| KJ803970* | GA_95432Td_2012 | 95432 | Tendon | 20-Aug-2012 | USA: GA | Broiler |
| KJ803971* | AL_95436Td_2012 | 95436 | Tendon | 21-Aug-2012 | USA: AL | Broiler |
| KJ803972** | AL_95437Ht_2012 | 95437 | Heart | 21-Aug-2012 | USA: AL | Broiler |
| KJ803973* | AL_95438Td_2012 | 95438 | Tendon | 21-Aug-2012 | USA: AL | Broiler |
| KJ803974* | AL_95522Td_2012 | 95522 | Tendon | 24-Aug-2012 | USA: AL | Broiler |
| KJ803975* | AL_95523Td_2012 | 95523 | Tendon | 24-Aug-2012 | USA: AL | Broiler |
| KJ803976** | AL_95524Td_2012 | 95524 | Tendon | 24-Aug-2012 | USA: AL | Broiler |
| KJ803977* | AL_95583Td_2012 | 95583 | Tendon | 30-Aug-2012 | USA: AL | Broiler |
| KJ803978** | AL_95647Td_2012 | 95647 | Tendon | 5-Sep-2012 | USA: AL | Broiler |
| KJ803980** | AL_95873Td_2012 | 95873 | Tendon | 25-Sep-2012 | USA: AL | Broiler |
| KJ803981* | AL_95930Td_2012 | 95930 | Tendon | 2-Oct-2012 | USA: AL | Broiler |
| KJ803982* | AL_95931Td_2012 | 95931 | Tendon | 2-Oct-2012 | USA: AL | Broiler |
| KJ803983* | AL_95932Td_2012 | 95932 | Tendon | 2-Oct-2012 | USA: AL | Broiler |
| KJ803984* | AL_95933Td_2012 | 95933 | Tendon | 2-Oct-2012 | USA: AL | Broiler |
| KJ803987** | NC_96034Td_2012 | 96034 | Tendon | 9-Oct-2012 | USA: NC | Broiler |
| KJ803990** | GA_96139Td_2012 | 96139 | Tendon | 17-Oct-2012 | USA: GA | Broiler |
| KJ803991* | GA_96317Td_2012 | 96317 | Tendon | 5-Nov-2012 | USA: GA | Broiler |
| KJ803995* | AR_96670Td_2012 | 96670 | Tendon | 7-Dec-2012 | USA: AR | Broiler Breeder |
| KJ804002* | NC_96824Td_2012 | 96824 | Tendon | 17-Dec-2012 | USA: NC | Broiler |
| KJ804003* | NC_96828Td_2012 | 96828 | Tendon | 17-Dec-2012 | USA: NC | Broiler |
| KJ804004** | KY_96837Td_2012 | 96837 | Tendon | 18-Dec-2012 | USA: KY | Broiler |
| KJ804006** | GA_96916Td_2012 | 96916 | Tendon | 20-Dec-2012 | USA: GA | Broiler |
| KJ804007** | GA_96917Td_2012 | 96917 | Tendon | 20-Dec-2012 | USA: GA | Broiler |
| KJ879626** | GA_96985Td_2013 | 96985 | Tendon | 3-Jan-2013 | USA: GA | Broiler |
| KJ879627** | GA_96986Td_2013 | 96986 | Tendon | 3-Jan-2013 | USA: GA | Broiler |
| KJ879628* | NC_97037Td_2013 | 97037 | Tendon | 4-Jan-2013 | USA: NC | Broiler |
| KJ879630* | NC_97039Td_2013 | 97039 | Tendon | 4-Jan-2013 | USA: NC | Broiler |
| KJ879631* | NC_97040Td_2013 | 97040 | Tendon | 4-Jan-2013 | USA: NC | Broiler |

TABLE 4-continued

Group 1 and Group 2 Avian Reoviruses

| Accession No. | Sequence ID | Isolate | Tissue type | Collection Date | Country | Isolation source |
|---|---|---|---|---|---|---|
| KJ879632* | NC_97041Td_2013 | 97041 | Tendon | 4-Jan-2013 | USA: NC | Broiler |
| KJ879633* | NC_97042Td_2013 | 97042 | Tendon | 4-Jan-2013 | USA: NC | Broiler |
| KJ879634* | NC_97043Td_2013 | 97043 | Tendon | 4-Jan-2013 | USA: NC | Broiler |
| KJ879637* | AR_97224Td_2013 | 97224 | Tendon | 17-Jan-2013 | USA: AR | Broiler |
| KJ879638* | AR_97225Td_2013 | 97225 | Tendon | 17-Jan-2013 | USA: AR | Broiler |
| KJ879639* | AR_97227Td_2013 | 97227 | Tendon | 17-Jan-2013 | USA: AR | Broiler |
| KJ879640* | AR_97230Td_2013 | 97230 | Tendon | 17-Jan-2013 | USA: AR | Broiler |
| KJ879647* | NC_97361Td_2013 | 97361 | Tendon | 24-Jan-2013 | USA: NC | Broiler |
| KJ879649* | AR_97407Td_2013 | 97407 | Tendon | 29-Jan-2013 | USA: AR | Broiler |
| KJ879650* | GA_97415Td_2013 | 97415 | Tendon | 29-Jan-2013 | USA: GA | Broiler |
| KJ879654* | FL_97480Td_2013 | 97480 | Tendon | 6-Feb-2013 | USA: FL | Broiler |
| KJ879655* | AB_97590Tdsw_2013 | 97590 | Tendon fluid swab | 12-Feb-2013 | Canada: AB | Broiler |
| KJ879657* | AB_97594Tdsw_2013 | 97594 | Tendon fluid swab | 12-Feb-2013 | Canada: AB | Broiler |
| KJ879658* | AB_97595Tdsw_2013 | 97595 | Tendon fluid swab | 12-Feb-2013 | Canada: AB | Broiler |
| KJ879659* | AB_97596Tdsw_2013 | 97596 | Tendon fluid swab | 12-Feb-2013 | Canada: AB | Broiler |
| KJ879662* | TX_97925Td_2013 | 97925 | Tendon | 5-Mar-2013 | USA: TX | Broiler |
| KJ879663* | TX_97926Td_2013 | 97926 | Tendon | 5-Mar-2013 | USA: TX | Broiler |
| KJ879666* | NC_97970Td_2313 | 97970 | Tendon | 6-Mar-2013 | USA: NC | Broiler |
| KJ879668** | MS_97993Td_2013 | 97993 | Tendon | 7-Mar-2013 | USA: MS | Broiler |
| KJ879669* | MS_98000Td_2013 | 98000 | Tendon | 8-Mar-2013 | USA: MS | Broiler |
| KJ879670* | SC_98005Td_2313 | 98005 | Tendon | 8-Mar-2013 | USA: SC | Broiler |
| KJ879671* | AB_98098Td_2013 | 98098 | Tendon | 13-Mar-2013 | Canada: AB | Broiler |
| KJ879672* | AB_98099Td_2013 | 98099 | Tendon | 13-Mar-2013 | Canada: AB | Broiler |
| KJ879673** | GA_98175Td_2013 | 98175 | Tendon | 18-Mar-2013 | USA: GA | Broiler |
| KJ879675* | SC_98694Td_2013 | 98694 | Tendon | 17-Apr-2013 | USA: SC | Broiler |
| KJ879678* | MS_98953Td_2013 | 98953 | Tendon | 30-Apr-2013 | USA: MS | Broiler |
| KJ879679* | MS_98955Td_2013 | 98955 | Tendon | 30-Apr-2013 | USA: MS | Broiler |
| KJ879680* | SC_99112Td_2013 | 99112 | Tendon | 9-May-2013 | USA: SC | Broiler |
| KJ879684* | NC_99272Td_2013 | 99272 | Tendon | 17-May-2013 | USA: NC | Broiler |
| KJ879687* | TN_99845Td_2013 | 99845 | Tendon | 21-Jun-2013 | USA: TN | Broiler |
| KJ879692** | GA_99952Td_2013 | 99952 | Tendon | 27-Jun-2013 | USA: GA | Broiler |
| KJ879695* | MS_10042Td_2013 | 100042 | Tendon | 3-Jul-2013 | USA: MS | Broiler |
| KJ879702* | MS_100201Td_2013 | 100201 | Tendon | 11-Jul-2013 | USA: MS | Broiler |
| KJ879709* | AR_100557Td_2013 | 100557 | Tendon | 1-Aug-2013 | USA: AR | Broiler breeder |
| KJ879710** | AR_100558Td_2013 | 100558 | Tendon | 1-Aug-2013 | USA: AR | Broiler breeder |
| KJ879711** | AR_100560Td_2013 | 100560 | Tendon | 1-Aug-2013 | USA: AR | Broiler breeder |
| KJ879712** | AR_100561Td_2013 | 100561 | Tendon | 1-Aug-2013 | USA: AR | Broiler breeder |
| KJ879713* | MS_100697Td_2013 | 100697 | Tendon | 9-Aug-2013 | USA: MS | Broiler |
| KJ879714* | MS_100782Td_2013 | 100782 | Tendon | 15-Aug-2013 | USA: MS | Broiler |
| KJ879715* | MS_100783Td_2013 | 100783 | Tendon | 15-Aug-2013 | USA: MS | Broiler |
| KJ879716* | MS_100810Td_2013 | 100810 | Tendon | 16-Aug-2013 | USA: MS | Broiler |
| KJ879717* | MS_100946Td_2013 | 100946 | Tendon | 29-Aug-2013 | USA: MS | Broiler |
| KJ879718* | MS_100947Td_2013 | 100947 | Tendon | 29-Aug-2013 | USA: MS | Broiler |
| KJ879719* | MS_100948Td_2013 | 100948 | Tendon | 29-Aug-2013 | USA: MS | Broiler |
| KJ879720* | TX_100970Td_2013 | 100970 | Tendon | 30-Aug-2013 | USA: TX | Broiler |
| KJ879723* | MS_101021Td_2013 | 101021 | Tendon | 5-Sep-2013 | USA: MS | Broiler |
| KJ879724* | MS_101039Td_2013 | 101039 | Tendon | 6-Sep-2013 | USA: MS | Broiler |
| KJ879725* | TX_101078Td_2013 | 101078 | Tendon | 10-Sep-2013 | USA: TX | Broiler |
| KJ879726* | TN_101279Td_2013 | 101279 | Tendon | 24-Sep-2013 | USA: TN | Broiler |
| KJ879728* | TN_101282Td_2013 | 101282 | Tendon | 24-Sep-2013 | USA: TN | Broiler |
| KJ879729* | TN_101291Td_2013 | 101291 | Tendon | 25-Sep-2013 | USA: TN | Broiler |
| KM282057* | TN_101293Td_2013 | 101293 | Tendon | 25-Sep-2013 | USA: TN | Broiler |
| KM282058* | SC_101343Td_2013 | 101343 | Tendon | 27-Sep-2013 | USA: SC | Broiler |
| KM282059* | TN_101490Td_2013 | 101490 | Tendon | 4-Oct-2013 | USA: TN | Broiler |
| KM282060* | TN_101491Td_2013 | 101491 | Tendon | 4-Oct-2013 | USA: TN | Broiler |
| KM282061* | TN_101492Td_2013 | 101492 | Tendon | 4-Oct-2013 | USA: TN | Broiler |
| KM282062* | TN_101493Td_2013 | 101493 | Tendon | 4-Oct-2013 | USA: TN | Broiler |
| KM282063* | TN_101494Td_2013 | 101494 | Tendon | 4-Oct-2013 | USA: TN | Broiler |
| KM282064* | AR_101548Td_2013 | 101548 | Tendon | 9-Oct-2013 | USA: AR | Broiler |
| KM282065* | AR_101549Td_2013 | 101549 | Tendon | 9-Oct-2013 | USA: AR | Broiler |
| KM282066* | AR_101550Td_2013 | 101550 | Tendon | 9-Oct-2013 | USA: AR | Broiler |
| KM282067** | MO_101582Td_2013 | 101582 | Tendon | 10-Oct-2013 | USA: MO | Broiler |
| KM282068* | AR_101604Td_2013 | 101604 | Tendon | 11-Oct-2013 | USA: AR | Broiler |
| KM282069* | AR_101605Td_2013 | 101605 | Tendon | 11-Oct-2013 | USA: AR | Broiler |
| KM282070* | AR_101606Td_2013 | 101606 | Tendon | 11-Oct-2013 | USA: AR | Broiler |
| KM282071* | AR_101607Td_2013 | 101607 | Tendon | 11-Oct-2013 | USA: AR | Broiler |
| KM282072* | AR_101608Td_2013 | 101608 | Tendon | 11-Oct-2013 | USA: AR | Broiler |
| KM282073* | AR_101609Td_2013 | 101609 | Tendon | 11-Oct-2013 | USA: AR | Broiler |
| KM282074* | AR_101610Td_2013 | 101610 | Tendon | 11-Oct-2013 | USA: AR | Broiler |
| KM282076* | TX_101782Td_2013 | 101782 | Tendon | 22-Oct-2013 | USA: TX | Broiler |
| KM282079* | MS_102033Td_2013 | 102033 | Tendon | 5-Nov-2013 | USA: MS | Broiler |
| KM282080* | MS_102036Td_2013 | 102036 | Tendon | 5-Nov-2013 | USA: MS | Broiler |
| KM282081* | GA_102492Td_2013 | 102492 | Tendon | 5-Dec-2013 | USA: GA | Broiler |
| KM282082** | AR_103077Td_2014 | 103077 | Tendon | 8-Jan-2014 | USA: AR | Broiler |
| KM282083* | MS_103097Td_2014 | 103097 | Tendon | 9-Jan-2014 | USA: MS | Broiler |
| KM282084* | MS_103124Td_2014 | 103124 | Tendon | 10-Jan-2014 | USA: MS | Broiler |

TABLE 4-continued

Group 1 and Group 2 Avian Reoviruses

| Accession No. | Sequence ID | Isolate | Tissue type | Collection Date | Country | Isolation source |
|---|---|---|---|---|---|---|
| KM282088* | GA_103671Td_2014 | 103671 | Tendon | 5-Feb-2014 | USA: GA | Broiler |
| KM282089* | AR_103754Td_2014 | 103754 | Tendon | 7-Feb-2014 | USA: AR | Broiler |
| KM282090* | TN_103959Td_2014 | 103959 | Tendon | 19-Feb-2014 | USA: TN | Broiler |
| KM282091** | GA_104190Td_2014 | 104190 | Tendon | 27-Feb-2014 | USA: GA | Broiler |
| KM282092* | TN_104248Td_2014 | 104248 | Tendon | 28-Feb-2014 | USA: TN | Broiler |
| KM282093* | OH_104254Td_2014 | 104254 | Tendon | 3-Mar-2014 | USA: OH | Broiler |
| KM282095* | KY_104414Td_2014 | 104414 | Tendon | 14-Mar-2014 | USA: KY | Broiler |
| KM282096* | KY_104415Td_2014 | 104415 | Tendon | 14-Mar-2014 | USA: KY | Broiler |
| KM282097** | IN_104533Td_2014 | 104533 | Tendon | 18-Mar-2014 | USA: IN | Broiler |

*Group 1 avian reovirus
**Group 2 avian reovirus

Example 6

Further Analysis of Group 1 and Group 2 Sigma C Protein Sequences

FIG. 21 shows the alignment of reovirus Sigma C amino acid sequences for the vaccine strains S1133 (SEQ ID NO:9), 1733 (SEQ ID NO:10), Enterovax (SEQ ID NO:11), and 2177 (SEQ ID NO:12) with various Group 1 and Group 2 reovirus isolates. Group I isolates include Ck-Canada-97594Td-2013 (SEQ ID NO:13), Ck-GA-91955Td-2011 (SEQ ID NO:14), Ck-MS-101021Td-2013 (SEQ ID NO:15), Ck-NC-97361Td-2013 (SEQ ID NO:16), Ck-SC-101343Td-2013 (SEQ ID NO:17), Ck-TN-101279Td-2013 (SEQ ID NO:18), Ck-TX-100970Td-2013 (SEQ ID NO:19), and Ck-AR-100557Td-2013 (SEQ ID NO:20). Group 2 isolates include Ck-AR-100558Td-2013 (SEQ ID NO:21), Ck-GA-98175Td-2013 (SEQ ID NO:22), Ck-MO-101582Td-2013 (SEQ ID NO:23), and Ck-AL-95524Td-2012 (SEQ ID NO:24). Amino acids (AA) that match S1133 represented by a dot (.) and AA that are different have single letter AA representing substitution.

Following the nomenclature of Kant et al. ("Classification of Dutch and German avian reoviruses by sequencing the sigma C protein," Vet Res, 2003; 34(2):203-12), Group 1 avian reovirus isolates, including isolate 94826, are placed in Genotype Cluster 5 and Group 2 avian reovirus, including isolate 96139, are placed in Genotype Cluster 1. This is shown in FIG. 22.

Figure 23B:
FIGS. 23A and 23B. Comparison of 94826 (group 1-cluster 5 reovirus) with S1133 (amino acids 120-310). Published crystal structure of S1133 used as backbone for PyMOL analysis (The PyMOL Molecular Graphics System, Version 1.3, Schrödinger, LLC. Reference: PDB IB 2JJL). A monomer of the Sigma C trimer is shown.
Figure 23A:
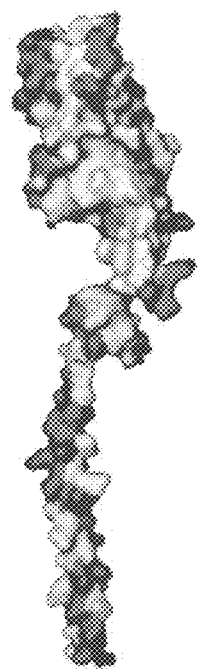
Figure 24B:
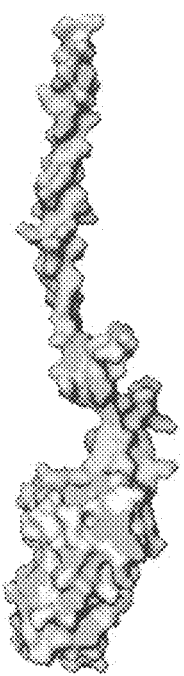
FIGS. 24A and 24B. Comparison of 96139 (group 2-cluster 1 reovirus) with S1133 (amino acids 120-310). Published crystal structure of S1133 used as backbone for PyMOL analysis (The PyMOL Molecular Graphics System, Version 1.3, Schrödinger, LLC. Reference: PDB IB 2JJL). A monomer of the Sigma C trimer is shown.
Figure 24A:
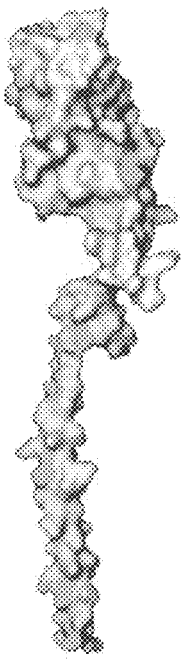

FIGS. 23A and 23B show a comparison of amino acids 120-310 of the Sigma C protein the Group 1 isolate 94826 compared to the vaccine strain S1133. FIGS. 24A and 24B show a comparison of amino acids 120-310 of the Sigma C protein the Group 2 isolate 96139 compared to the vaccine strain S1133. For this analysis, the published crystal structure of S1133 was used as backbone for PyMOL analysis (The PyMOL Molecular Graphics System, Version 1.3, Schrödinger, LLC. Reference: PDB IB 2JJL).

Example 7

Attenuation of Group 1 and Group 2 Variant Avian Reoviruses

The Group 1 and Group 2 avian reovirus isolates listed in Table 4, including, but not limited to the 94826 and 94594 isolates (both Group 1 isolates) and the 96139 isolate (a Group 2 isolate), will be attenuated by passage in eggs or cell lines, such as for example, chicken embryo liver cells (CELiC). A clonal, plaque purified virus preparation will be prepared after each passage and used for the next round of attenuation. The pathogenicity and vaccine effectiveness of an isolate will be tested after about every 25 passages, for example after about 25, about 50, about 75, about 100, and about 125 passages. The amino acid sequence of the C sigma protein will be obtained for attenuated strains.

Example 8

Attenuation of Group 1 and Group 2 Variant Avian Reoviruses

The 94826 Group 1 avian reovirus isolate has been passaged 119 times in chicken embryos. Passaging will continue twice weekly. The $39^{th}$ embryo passage has been passaged 44 times in chicken embryo fibroblast (CEF) cells. Passaging will continue twice weekly. The $50^{th}$ CEF passage will be assayed for attenuation.

The 96139 Group 2 avian reovirus isolate has been passaged 119 times in chicken embryos. Passaging will continue twice weekly. The $31^{st}$ embryo passage has been passaged 45 times in CEF cells. Passaging will continue twice weekly. The $50^{th}$ CEF passage will be assayed for attenuation.

This is shown in Table 5 below.

TABLE 5

Passage numbers for attenuation in specific pathogen free (SPF) embryos and primary chicken embryo fibroblast (CEF) cells prepared from SPF embryos.

| Reovirus isolate | Embryo passage | Embryo passage inoculated into CEF | CEF passage |
|---|---|---|---|
| 94826 - Group 1 variant | 119 | C39 | CEF 44 |
| 96139 - Group 2 variant | 119 | C31 | CEF 45 |

Example 9

Preparation of Hyperimmune Sera to Group 1 and Group 2 Variant Avian Reoviruses

Hyperimmune serum has been prepared for both the 94826 Group 1 avian reovirus isolate and the 96139 Group 2 avian reovirus isolate. Briefly, whole virus was used to immunize 3-week-old Specific Pathogen Free (SPF) chickens at 10(3) tissue culture infectious dose 50/bird via eye drop application. At 6 weeks-of-age, birds were injected with 0.5 ml inactivated virus in an oil adjuvant via intramuscular injection. Birds were bled at 9 weeks-of-age and reovirus serology (ELISA and virus neutralizations) was performed. In samples with good titers, birds were exsanguinated per IACUC approved protocols. If titers were not adequate, a second inactivated/oil adjuvant injection was administered via intramuscular injection. Final bleed at 13 weeks of age.

Such hyperimmune serum may be used as positive control serum samples in diagnostic assays, such as, for example, a virus neutralization assay with plaque purified virus, to determine if birds have been vaccinated or exposed to a Group 1 or Group 2 avian reovirus isolate.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Sequence Free Listing

SEQ ID NO:1 S1 nucleotide sequence encoding the sigma C protein (base pairs 1-931) from group 1 2012 VA variant field isolate 94594
SEQ ID NO:2 S1 amino acid sequence of the sigma C (amino acids 1-310) from group 1 2012 VA variant field isolate 94594
SEQ ID NO:3 S1 nucleotide sequence encoding the sigma C protein (base pairs 1-931) from group 1 2012 VA variant field isolate 94826
SEQ ID NO:4 S1 amino acid sequence of the sigma C (amino acids 1-310) from group 1 2012 VA variant field isolate 94826
SEQ ID NO:5 S1 nucleotide sequence encoding the sigma C protein (base pairs 1-931) from group 2 2012 VA variant field isolate 96139
SEQ ID NO:6 S1 amino acid sequence of the sigma C protein (amino acids 1-310) from group 2 2012 VA variant field isolate 96139
SEQ ID NO:7 P1 PCR primer
SEQ ID NO:8 P4 PCR primer
SEQ ID NO:9 Amino acid sequence of sigma C protein of the S1133 avian reovirus vaccine
SEQ ID NO:10 Amino acid sequence of sigma C protein of the 1733 avian reovirus vaccine
SEQ ID NO:11 Amino acid sequence of sigma C protein of the Enterovax avian reovirus vaccine
SEQ ID NO:12 Amino acid sequence of sigma C protein of the 2177 avian reovirus vaccine
SEQ ID NO:13 Amino acid sequence of sigma C protein of avian reovirus Group 1 isolate Ck-Canada-97594Td-2013
SEQ ID NO:14 Amino acid sequence of sigma C protein of avian reovirus Group 1 isolate Ck-GA-91955Td-2011
SEQ ID NO:15 Amino acid sequence of sigma C protein of avian reovirus Group 1 isolate Ck-MS-101021Td-2013
SEQ ID NO:16 Amino acid sequence of sigma C protein of avian reovirus Group 1 isolate Ck-NC-97361Td-2013
SEQ ID NO:17 Amino acid sequence of sigma C protein of avian reovirus Group 1 isolate Ck-SC-101343Td-2013
SEQ ID NO:18 Amino acid sequence of sigma C protein of avian reovirus Group 1 isolate Ck-TN-101279Td-2013
SEQ ID NO:19 Amino acid sequence of sigma C protein of avian reovirus Group 1 isolate Ck-TX-100970Td-2013
SEQ ID NO:20 Amino acid sequence of sigma C protein of avian reovirus Group 1 isolate Ck-AR-100557Td-2013
SEQ ID NO:21 Amino acid sequence of sigma C protein of avian reovirus Group 2 isolate Ck-AR-100558Td-2013
SEQ ID NO:22 Amino acid sequence of sigma C protein of avian reovirus Group 2 isolate Ck-GA-98175Td-2013
SEQ ID NO:23 Amino acid sequence of sigma C protein of avian reovirus Group 2 isolate Ck-MO-101582Td-2013
SEQ ID NO:24 Amino acid sequence of sigma C protein of avian reovirus Group 2 isolate Ck-AL-95524Td-2012

What is claimed is:

1. An isolated avian reovirus, wherein the avian reovirus comprises:
a sigma C protein comprising an amino acid sequence with at least 99% sequence identity to SEQ ID NO:4 and comprising at least one amino acid difference from SEQ ID NO:4,
wherein the avian reovirus is attenuated relative to an avian reovirus comprising a sigma C protein with an amino acid sequence comprising SEQ ID NO:4 by at least 25 passages in an egg or a host cell line.

2. An avian reovirus of claim 1, wherein the avian reovirus is inactivated or killed.

3. The avian reovirus of claim 2, wherein the avian reovirus is chemically inactivated or killed by subjecting to energetic radiation.

4. A composition comprising an avian reovirus of claim 1.

5. A composition of claim 4, further comprising an adjuvant.

6. A diagnostic kit comprising a virus of claim 1.

7. A method of producing anti-reovirus antibodies in poultry, the method comprising administering an isolated avian reovirus of claim 1 to the bird.

8. The method of claim 7, wherein the bird is a chicken or turkey.

9. A method of claim 7, wherein administration comprises in ovo administration.

10. A method of claim 7, wherein administration comprises administration to a breeder hen.

11. A method of detecting exposure to an avian reovirus in a bird, the method comprising determining that an antisera sample obtained from the bird specifically binds to an avian reovirus of claim 1.

12. The avian reovirus of claim 1, wherein the avian reovirus is attenuated by at least 100 passages in an egg or a host cell line.

13. An isolated avian reovirus, wherein the avian reovirus comprises:
a sigma C protein comprising an amino acid sequence with at least 99% sequence identity to SEQ ID NO:4 and comprising at least one amino acid difference from SEQ ID NO:4;
wherein the avian reovirus is attenuated relative to an avian reovirus comprising a sigma C protein with an amino acid sequence comprising SEQ ID NO:4.

14. An avian reovirus of claim 13, wherein the avian reovirus is inactivated or killed.

15. The avian reovirus of claim 14, wherein the avian reovirus is chemically inactivated or killed by subjecting to energetic radiation.

16. A composition comprising an avian reovirus of claim 13.

17. A composition of claim 16, further comprising an adjuvant.

18. A diagnostic kit comprising a virus of claim 13.

19. A method of producing anti-reovirus antibodies in poultry, the method comprising administering an isolated avian reovirus of claim 13 to the bird.

20. The method of claim 19, wherein the bird is a chicken or turkey.

21. A method of claim 19, wherein administration comprises in ovo administration.

22. A method of claim 19, wherein administration comprises administration to a breeder hen.

23. A method of detecting exposure to an avian reovirus in a bird, the method comprising determining that an antisera sample obtained from the bird specifically binds to an avian reovirus of claim 13.

* * * * *

SEQUENCE LISTING

```
<160> NUMBER OF SEQ ID NOS: 24

<210> SEQ ID NO 1
<211> LENGTH: 931
<212> TYPE: DNA
<213> ORGANISM: Avian reovirus

<400> SEQUENCE: 1
atggacggat taactcaaca gcagcgaaga gaagtcgtgg ggttgatact gtcgttgact      60
tcgagcgtga gtacaagttc tggcgatttg acgcaaattc gtgaacgtct ttccgctttg     120
gaatctgcga ctgcgtcgtt gaacgaatct attaatacag ctttgtctaa gttagtggat     180
ttgtctgcat cgcttgacaa cgtggcggcc tcgttagcgg agacgaaagt ggaagtgaac     240
tcattggttt ccgacgttca gggtttgcga acttctcttg attcttctgc ttcagagctg     300
gcttctctat cttcgttggt gcgtgatcac ggctcttcga ttgctagcct acagaaagaa     360
gtaagtgtct tatcgggtga ggtaggcaac cttaaaacct cggtatcatc gcagggcctt     420
actatcacta gccttgagaa acgagtggaa gctttggaag gtggttctag tacgactctg     480
tcatttgctg atcctcttaa gttagaggct gggaccgtgt cactcgaggt agatccatat     540
```

-continued

```
ttctgctctg taaatcgtaa tctgacgtcg tattctgcta atgctcagtt gatgcaattt    600
cagtggtctg tgaaggggga agatggcgcg gccaactcta ttgatatgga cgtgaatgct    660
cactctcatg gttcacgcac tgattatctg atgtcaacca agcaatcatt gactgttaca    720
acgtctcccg ctactctcgt ctttgaactg gataggattc tgctcttcc ctctgacctt     780 tctcgcctaa ttccatgtta tggttttcag caagctactt ttcctgttga tatctccttc    840
cagcgagatg gcgtctcgca tacgtatcaa gtctatggga cgtacacatc ttctcgcgtc    900
ttcaagatta cgttctcgcc tggctcctcg g                                   931
```

<210> SEQ ID NO 2
<211> LENGTH: 310
<212> TYPE: PRT
<213> ORGANISM: Avian reovirus

<400> SEQUENCE: 2

```
Met As

Phe Ser Pro Gly Ser Ser
305                 310

<210> SEQ ID NO 3
<211> LENGTH: 931
<212> TYPE: DNA
<213> ORGANISM: Avian reovirus

<400> SEQUENCE: 3
atggacggat taactcaaca gcagcgaaga gaagtcgtgg ggttgatact gtcgttgact    60
tcgagcgtga gtacaagttc tggcgatttg acgcaaattc gtgaacgtct ttccgctttg   120
gaatctgcga ctgcgtcgtt gaacgaatct attaatacag ctttatctaa gttagtggat   180
ttgtctgcat cgcttgacaa cgtggcggcc tcgttagcgg agacgaaagt ggaagtgaac   240
tcattggttt ccgacgttca gggtttgcga acttctcttg attcttctgc ttcagagctg   300
gcttctctat cttcgttggt gcgtgatcac ggctcttcga ttgctagcct acagaaagaa   360
gtaagtgtct tatcgggtga ggtaggcaac cttaaaacct cggtatcatc gcagggcctt   420
actatcacta gccttgagaa acgagtggaa gctttggaag gtggttctag tacgactctg   480
tcatttgctg atcctcttaa gttagaggct gggaccgtgt cactcgaggt agatccatat   540
ttctgctctg taaatcgtaa tctgacgtcg tattctgcta atgctcagtt gatgcaattt   600
cagtggtctg tgaaggggga agatggcgcg gccaactcta ttgatatgga cgtgaatgct   660
cactctcatg gttcacgcac tgattatctg atgtcaacca agcaatcatt gactgttaca   720
acgtctcccg ctactctcgt ctttgaactg ataggattc tgctcttcc ctctgacctt   780 tctcgcctaa ttccatgtta tggttttcag caagctactt ttcctgttga tatctccttc   840
cagcgagatg cgctctcgca tacgtatcaa gtctatggga cgtacacatc ttctcgcgtc   900
ttcaagatta cgttctcgcc tggctcctca g                                  931

<210> SEQ ID NO 4
<211> LENGTH: 310
<212> TYPE: PRT
<213> ORGANISM: Avian reovirus

<400> SEQUENCE: 4

Met Asp Gly Leu Thr Gln Gln Gln Arg Arg Glu Val Val Gly Leu Ile
1               5                   10                  15

Leu Ser Leu Thr Ser Ser Val Ser Thr Ser Ser Gly Asp Leu Thr Gln
            20                  25                  30

Ile Arg Glu Arg Leu Ser Ala Leu Glu Ser Ala Thr Ala Ser Leu Asn
        35                  40                  45

Glu Ser Ile Asn Thr Ala Leu Ser Lys Leu Val Asp Leu Ser Ala Ser
    50                  55                  60

Leu Asp Asn Val Ala Ala Ser Leu Ala Glu Thr Lys Val Glu Val Asn
65                  70                  75                  80

Ser Leu Val Ser Asp Val Gln Gly Leu Arg Thr Ser Leu Asp Ser Ser
                85                  90                  95

Ala Ser Glu Leu Ala Ser Leu Ser Ser Leu Val Arg Asp His Gly Ser
            100                 105                 110

Ser Ile Ala Ser Leu Gln Lys Glu Val Ser Val Leu Ser Gly Glu Val
        115                 120                 125

Gly Asn Leu Lys Thr Ser Val Ser Ser Gln Gly Leu Thr Ile Thr Ser
    130                 135                 140

```
Leu Glu Lys Arg Val Glu Ala Leu Glu Gly Gly Ser Ser Thr Thr Leu
145                 150                 155                 160

Ser Phe Ala Asp Pro Leu Lys Leu Glu Ala Gly Thr Val Ser Leu Glu
                165                 170                 175

Val Asp Pro Tyr Phe Cys Ser Val Asn Arg Asn Leu Thr Ser Tyr Ser
            180                 185                 190

Ala Asn Ala Gln Leu Met Gln Phe Gln Trp Ser Val Lys Gly Glu Asp
        195                 200                 205

Gly Ala Ala Asn Ser Ile Asp Met Asp Val Asn Ala His Ser His Gly
    210                 215                 220

Ser Arg Thr Asp Tyr Leu Met Ser Thr Lys Gln Ser Leu Thr Val Thr
225                 230                 235                 240

Thr Ser Pro Ala Thr Leu Val Phe Glu Leu Asp Arg Ile Ala Ala Leu
                245                 250                 255

Pro Ser Asp Leu Ser Arg Leu Ile Pro Cys Tyr Gly Phe Gln Gln Ala
            260                 265                 270

Thr Phe Pro Val Asp Ile Ser Phe Gln Arg Asp Gly Val Ser His Thr
        275                 280                 285

Tyr Gln Val Tyr Gly Thr Tyr Thr Ser Ser Arg Val Phe Lys Ile Thr
290                 295                 300

Phe Ser Pro Gly Ser Ser
305             310

<210> SEQ ID NO 5
<211> LENGTH: 931
<212> TYPE: DNA
<213> ORGANISM: Avian reovirus

<400> SEQUENCE: 5
atggcgggtc tcagtccatc acagcgaaga gaggtcgtca gcttgatact gtcattgact    60
tcgaacgcga ctataagtcc tggcgatttg acgacaatcc atgagcggtt gactaatttg   120
gaagcgtcta cagaatcact ataccgctcc atctccagca tgtctgttac tgtttccgac   180
gtttctacag atttgcagaa cgtgactcgc gctctggatg atgtgatcac caacttaaat   240
ggtatgagag ccaccattac tgcacttcaa gattctgttt ccactctctc aacaactgtg   300
accgacttat caagcacttc ttctgcgcat tcggaaactc tatcttcact ccgaaataca   360
gttaatggga actccactac cattggtaat ttgaaaagtg atgtatcatc aaatggccta   420
gctatcacag acctgcagag tcgcgttaaa tccttggagt ctacttcgag tcacggactg   480 tcctttctc ctcctcttag tgtcgctgac ggcgtggtgt cgttaatat ggacccgtac   540 ttttgctctc agcgagtttc cttgacatct tactcagcag aggctcaact aatgcaattc   600
caatggatgg ccagaggttc taacggatca tcggacaata ttgacatgaa cgttaacgcc   660
cactgtcatg ggagacgcac tgactatata atgtcgtcta cgggaggtct tacggttact   720
cgtaatgccg tgtccttaac cttcgatttg agttatatta caaagctccc atcggacctc   780
tcacgtctta tccccagtgc gggatttcaa gccgcgtcgt ttccagcgga tgtatccttc   840
accagagatt ccacaaccca tgcgtatcaa gcttatggag tatattccag ctctcgcgta   900
tttactatta ctttcccgac tggtggtgac g                                  931

<210> SEQ ID NO 6
<211> LENGTH: 310
<212> TYPE: PRT
<213> ORGANISM: Avian reovirus
```

<400> SEQUENCE: 6

```
Met Ala Gly Leu Ser Pro Ser Gln Arg Arg Glu Val Val Ser Leu Ile
1               5                   10                  15

Leu Ser Leu Thr Ser Asn Ala Thr Ile Ser Pro Gly Asp Leu Thr Thr
            20                  25                  30

Ile His Glu Arg Leu Thr Asn Leu Glu Ala Ser Thr Glu Ser Leu Tyr
        35                  40                  45

Arg Ser Ile Ser Ser Met Ser Val Thr Val Ser Asp Val Ser Thr Asp
    50                  55                  60

Leu Gln Asn Val Thr Arg Ala Leu Asp Asp Val Ile Thr Asn Leu Asn
65                  70                  75                  80

Gly Met Arg Ala Thr Ile Thr Ala Leu Gln Asp Ser Val Ser Thr Leu
                85                  90                  95

Ser Thr Thr Val Thr Asp Leu Ser Thr Ser Ser Ala His Ser Glu
            100                 105                 110

Thr Leu Ser Ser Leu Arg Asn Thr Val Asn Gly Asn Ser Thr Thr Ile
            115                 120                 125

Gly Asn Leu Lys Ser Asp Val Ser Ser Asn Gly Leu Ala Ile Thr Asp
130                 135                 140

Leu Gln Ser Arg Val Lys Ser Leu Glu Ser Thr Ser Ser His Gly Leu
145                 150                 155                 160

Ser Phe Ser Pro Leu Ser Val Ala Asp Gly Val Val Ser Leu Asn
                165                 170                 175

Met Asp Pro Tyr Phe Cys Ser Gln Arg Val Ser Leu Thr Ser Tyr Ser
            180                 185                 190

Ala Glu Ala Gln Leu Met Gln Phe Gln Trp Met Ala Arg Gly Ser Asn
        195                 200                 205

Gly Ser Ser Asp Asn Ile Asp Met Asn Val Asn Ala His Cys His Gly
    210                 215                 220

Arg Arg Thr Asp Tyr Ile Met Ser Ser Thr Gly Gly Leu Thr Val Thr
225                 230                 235                 240

Arg Asn Ala Val Ser Leu Thr Phe Asp Leu Ser Tyr Ile Thr Lys Leu
                245                 250                 255

Pro Ser Asp Leu Ser Arg Leu Ile Pro Ser Ala Gly Phe Gln Ala Ala
            260                 265                 270

Ser Phe Pro Ala Asp Val Ser Phe Thr Arg Asp Ser Thr His Ala
        275                 280                 285

Tyr Gln Ala Tyr Gly Val Tyr Ser Ser Ser Arg Val Phe Thr Ile Thr
    290                 295                 300

Phe Pro Thr Gly Gly Asp
305                 310
```

<210> SEQ ID NO 7
<211> LENGTH: 20
<212> TYPE: DNA
<213> ORGANISM: artificial
<220> FEATURE:
<223> OTHER INFORMATION: synthetic oligonucleotide primer

<400> SEQUENCE: 7
agtatttgtg agtacgattg                                          20

<210> SEQ ID NO 8
<211> LENGTH: 17
<212> TYPE: DNA
<213> ORGANISM: artificial

```
<220> FEATURE:
<223> OTHER INFORMATION: synthetic oligonucleotide primer

<400> SEQUENCE: 8
ggcgccacac cttaggt                                                  17

<210> SEQ ID NO 9
<211> LENGTH: 309
<212> TYPE: PRT
<213> ORGANISM: artificial
<220> FEATURE:
<223> OTHER INFORMATION: vaccine strain S1133

<400> SEQUENCE: 9
```

Met Ala Gly Leu Asn Pro Ser Gln Arg Arg Glu Val Val Ser Leu Ile
1               5                   10                  15

Leu Ser Leu Thr Ser Asn Val Asn Ile Ser His Gly Asp Leu Thr Pro
            20                  25                  30

Ile Tyr Glu Arg Leu Thr Asn Leu Glu Ala Ser Thr Glu Leu Leu His
        35                  40                  45

Arg Ser Ile Ser Asp Ile Ser Thr Thr Val Ser Asn Ile Ser Ala Asn
    50                  55                  60

Leu Gln Asp Met Thr His Thr Leu Asp Val Thr Ala Asn Leu Asp
65                  70                  75                  80

Gly Leu Arg Thr Thr Val Thr Ala Leu Gln Asp Ser Val Ser Ile Leu
                85                  90                  95

Ser Thr Asn Val Thr Asp Leu Thr Asn Arg Ser Ser Ala His Ala Ala
            100                 105                 110

Ile Leu Ser Ser Leu Gln Thr Thr Val Asp Gly Asn Ser Thr Ala Ile
        115                 120                 125

Ser Asn Leu Lys Ser Asp Ile Ser Ser Asn Gly Leu Ala Ile Thr Asp
    130                 135                 140

Leu Gln Asp Arg Val Lys Ser Leu Glu Ser Thr Ala Ser His Gly Leu
145                 150                 155                 160

Ser Phe Ser Pro Pro Leu Ser Val Ala Asp Gly Val Val Ser Leu Asp
                165                 170                 175

Met Asp Pro Tyr Phe Cys Ser Gln Arg Val Ser Leu Thr Ser Tyr Ser
            180                 185                 190

Ala Glu Ala Gln Leu Met Gln Phe Arg Trp Met Ala Arg Gly Thr Asn
        195                 200                 205

Gly Ser Ser Asp Thr Ile Asp Met Thr Val Asn Ala His Cys His Gly
    210                 215                 220

Arg Arg Thr Asp Tyr Met Met Ser Ser Thr Gly Asn Leu Thr Val Thr
225                 230                 235                 240

Ser Asn Val Val Leu Thr Phe Asp Leu Ser Asp Ile Thr His Ile
                245                 250                 255

Pro Ser Asp Leu Ala Arg Leu Val Pro Ser Ala Gly Phe Gln Ala Ala
            260                 265                 270

Ser Phe Pro Val Asp Val Ser Phe Thr Arg Asp Ser Ala Thr His Ala
        275                 280                 285

Tyr Gln Ala Tyr Gly Val Tyr Ser Ser Ser Arg Val Phe Thr Ile Thr
    290                 295                 300

Phe Pro Thr Gly Gly
305

```
<210> SEQ ID NO 10
```

```
<211> LENGTH: 309
<212> TYPE: PRT
<213> ORGANISM: artificial
<220> FEATURE:
<223> OTHER INFORMATION: vaccine strain 1733

<400> SEQUENCE: 10
```

| Met | Ala | Gly | Leu | Asn | Pro | Ser | Gln | Arg | Arg | Glu | Val | Val | Ser | Leu | Ile |
|---|---|---|---|---|---|---|---|---|---|---|---|---|---|---|---|
| 1 | | | | 5 | | | | | 10 | | | | | 15 | |

| Leu | Ser | Leu | Thr | Ser | Asn | Val | Thr | Ile | Ser | Thr | Gly | Asp | Leu | Thr | Pro |
|---|---|---|---|---|---|---|---|---|---|---|---|---|---|---|---|
| | | | 20 | | | | | 25 | | | | | 30 | | |

| Ile | Tyr | Glu | Arg | Leu | Thr | Asn | Leu | Glu | Ala | Ser | Thr | Glu | Leu | Leu | His |
|---|---|---|---|---|---|---|---|---|---|---|---|---|---|---|---|
| | | | 35 | | | | | 40 | | | | | 45 | | |

| Arg | Ser | Ile | Ser | Asp | Ile | Ser | Thr | Thr | Val | Ser | Asn | Ile | Ser | Ala | Asn |
|---|---|---|---|---|---|---|---|---|---|---|---|---|---|---|---|
| | 50 | | | | | 55 | | | | | 60 | | | | |

| Leu | Gln | Asp | Met | Thr | His | Ile | Leu | Asp | Asp | Val | Thr | Ala | Asn | Leu | Asp |
|---|---|---|---|---|---|---|---|---|---|---|---|---|---|---|---|
| 65 | | | | | 70 | | | | | 75 | | | | | 80 |

| Gly | Leu | Arg | Thr | Thr | Val | Thr | Ala | Leu | Gln | Asp | Ser | Val | Ser | Ile | Leu |
|---|---|---|---|---|---|---|---|---|---|---|---|---|---|---|---|
| | | | | 85 | | | | | 90 | | | | | 95 | |

| Ser | Thr | Asn | Val | Thr | Asp | Leu | Thr | Asn | Thr | Ser | Ser | Ala | His | Ala | Ala |
|---|---|---|---|---|---|---|---|---|---|---|---|---|---|---|---|
| | | | | 100 | | | | | 105 | | | | | 110 | |

| Thr | Leu | Ser | Ser | Leu | Gln | Thr | Thr | Val | Asp | Gly | Asn | Ser | Thr | Ala | Ile |
|---|---|---|---|---|---|---|---|---|---|---|---|---|---|---|---|
| | | | 115 | | | | | 120 | | | | | 125 | | |

| Ser | Asn | Leu | Lys | Ser | Asp | Val | Ser | Ser | Asn | Gly | Leu | Ala | Ile | Thr | Asp |
|---|---|---|---|---|---|---|---|---|---|---|---|---|---|---|---|
| | 130 | | | | | 135 | | | | | 140 | | | | |

| Leu | Gln | Asp | Arg | Val | Lys | Ser | Leu | Glu | Ser | Thr | Ala | Ser | His | Gly | Leu |
|---|---|---|---|---|---|---|---|---|---|---|---|---|---|---|---|
| 145 | | | | | 150 | | | | | 155 | | | | | 160 |

| Ser | Phe | Ser | Pro | Pro | Leu | Ser | Val | Ala | Asp | Gly | Val | Val | Ser | Leu | Asp |
|---|---|---|---|---|---|---|---|---|---|---|---|---|---|---|---|
| | | | | 165 | | | | | 170 | | | | | 175 | |

| Met | Asp | Pro | Tyr | Phe | Cys | Ser | Gln | Arg | Val | Ser | Leu | Thr | Ser | Tyr | Ser |
|---|---|---|---|---|---|---|---|---|---|---|---|---|---|---|---|
| | | | | 180 | | | | | 185 | | | | | 190 | |

| Ala | Glu | Ala | Gln | Leu | Met | Gln | Phe | Arg | Trp | Met | Ala | Arg | Gly | Thr | Asn |
|---|---|---|---|---|---|---|---|---|---|---|---|---|---|---|---|
| | | | 195 | | | | | 200 | | | | | 205 | | |

| Gly | Ser | Ser | Asp | Thr | Ile | Asp | Met | Thr | Val | Asn | Ala | His | Cys | His | Gly |
|---|---|---|---|---|---|---|---|---|---|---|---|---|---|---|---|
| | 210 | | | | | 215 | | | | | 220 | | | | |

| Arg | Arg | Thr | Asp | Tyr | Met | Met | Ser | Ser | Thr | Gly | Asn | Leu | Thr | Val | Thr |
|---|---|---|---|---|---|---|---|---|---|---|---|---|---|---|---|
| 225 | | | | | 230 | | | | | 235 | | | | | 240 |

| Ser | Asn | Val | Val | Leu | Leu | Thr | Phe | Asp | Leu | Ser | Asp | Ile | Thr | His | Ile |
|---|---|---|---|---|---|---|---|---|---|---|---|---|---|---|---|
| | | | | 245 | | | | | 250 | | | | | 255 | |

| Pro | Ser | Asp | Leu | Ala | Arg | Leu | Val | Pro | Ser | Ala | Gly | Phe | Gln | Ala | Ala |
|---|---|---|---|---|---|---|---|---|---|---|---|---|---|---|---|
| | | | 260 | | | | | 265 | | | | | 270 | | |

| Ser | Phe | Pro | Val | Asp | Val | Ser | Phe | Thr | Arg | Asp | Ser | Ala | Thr | His | Ala |
|---|---|---|---|---|---|---|---|---|---|---|---|---|---|---|---|
| | | 275 | | | | | 280 | | | | | 285 | | | |

| Tyr | Gln | Ala | Tyr | Gly | Val | Tyr | Ser | Ser | Ser | Arg | Val | Phe | Thr | Ile | Thr |
|---|---|---|---|---|---|---|---|---|---|---|---|---|---|---|---|
| | 290 | | | | | 295 | | | | | 300 | | | | |

| Phe | Pro | Thr | Gly | Gly |
|---|---|---|---|---|
| 305 | | | | |

```
<210> SEQ ID NO 11
<211> LENGTH: 309
<212> TYPE: PRT
<213> ORGANISM: artificial
<220> FEATURE:
<223> OTHER INFORMATION: vaccine strain Enterovax

<400> SEQUENCE: 11
```

| Met | Ala | Gly | Leu | Asn | Pro | Ser | Gln | Arg |

```
  1               5                  10                 15
Leu Ser Leu Thr Ser Asn Val Thr Ile Ser His Gly Asp Leu Thr Pro
                 20                 25                 30

Ile Tyr Glu Arg Leu Thr Asn Leu Glu Ala Ser Thr Glu Leu Leu His
             35                 40                 45

Arg Ser Ile Ser Asp Ile Ser Thr Thr Val Ser Asn Ile Ser Ala Asn
         50                 55                 60

Leu Gln Asp Met Thr His Thr Leu Asp Asp Val Thr Ala Asn Leu Asp
 65                 70                 75                 80

Gly Leu Arg Thr Thr Val Thr Ala Leu Gln Asp Ser Val Ser Ile Leu
                 85                 90                 95

Ser Thr Asn Val Thr Asp Leu Thr Asn Thr Ser Ser Ala His Ala Ala
                100                105                110

Thr Leu Ser Ser Leu Gln Thr Thr Val Asp Gly Asn Ser Thr Ala Ile
            115                120                125

Ser Asn Leu Lys Ser Asp Val Ser Ser Asn Gly Leu Ala Ile Thr Asp
        130                135                140

Leu Gln Asp Arg Val Lys Ser Leu Glu Ser Thr Ala Ser His Gly Leu
145                150                155                160

Ser Phe Ser Pro Pro Leu Ser Val Ala Asp Gly Val Val Ser Leu Asp
                165                170                175

Met Asp Pro Tyr Phe Cys Ser Gln Arg Val Ser Leu Thr Ser Tyr Ser
            180                185                190

Ala Glu Ala Gln Leu Met Gln Phe Arg Trp Met Ala Arg Gly Thr Asn
        195                200                205

Gly Ser Ser Asp Thr Ile Asp Met Thr Val Asn Ala His Cys His Gly
210                215                220

Arg Arg Thr Asp Tyr Met Met Ser Ser Thr Gly Asn Leu Thr Val Thr
225                230                235                240

Ser Asn Val Val Leu Leu Thr Phe Asp Leu Ser Asp Ile Thr His Ile
                245                250                255

Pro Ser Asp Leu Ala Arg Leu Val Pro Ser Ala Gly Phe Gln Ala Ala
            260                265                270

Ser Phe Pro Val Asp Val Ser Phe Thr Arg Asp Ser Ala Thr His Ala
        275                280                285

Tyr Gln Ala Tyr Gly Val Tyr Ser Ser Ser Arg Val Phe Thr Ile Thr
        290                295                300

Phe Pro Thr Gly Gly
305

<210> SEQ ID NO 12
<211> LENGTH: 309
<212> TYPE: PRT
<213> ORGANISM: artificial
<220> FEATURE:
<223> OTHER INFORMATION: vaccine strain 2177

<400> SEQUENCE: 12

Met Ala Gly Leu Asn Pro Ser Gln Arg Arg Glu Val Val Ser Leu Ile
 1               5                  10                 15

Leu Ser Leu Thr Ser Asn Val Thr Ile Ser His Gly Asp Leu Thr Pro
                 20                 25                 30

Ile Tyr Glu Arg Leu Thr Asn Leu Glu Ala Ser Thr Glu Leu Leu His
             35                 40                 45

Arg Ser Ile Ser Asp Ile Ser Thr Thr Val Ser Asn Ile Ser Ala Asn
```

```
Leu Gln Asp Met Thr His Thr Leu Asp Asp Val Thr Ala Asn Leu Asp
 65                  70                  75                  80

Gly Leu Arg Thr Thr Val Thr Ala Leu Gln Asp Ser Val Ser Ile Leu
                 85                  90                  95

Ser Thr Asn Val Thr Asp Leu Thr Asn Thr Ser Ser Ala His Ala Ala
             100                 105                 110

Thr Leu Ser Ser Leu Gln Thr Thr Val Asp Glu Asn Ser Thr Ala Ile
         115                 120                 125

Ser Asn Leu Lys Ser Asp Val Ser Ser Asn Gly Leu Ala Ile Thr Asp
     130                 135                 140

Leu Gln Asp Arg Val Lys Ser Leu Glu Ser Thr Ala Ser His Gly Leu
145                 150                 155                 160

Ser Phe Ser Pro Pro Leu Ser Val Ala Asp Gly Val Val Ser Leu Asp
                 165                 170                 175

Met Asp Pro Tyr Phe Cys Ser Gln Arg Val Ser Leu Thr Ser Tyr Ser
             180                 185                 190

Ala Glu Ala Gln Leu Met Gln Phe Arg Trp Met Ala Arg Gly Thr Asn
         195                 200                 205

Gly Ser Ser Asp Thr Ile Asp Met Thr Val Asn Ala His Cys His Gly
     210                 215                 220

Arg Arg Thr Asp Tyr Met Met Ser Ser Thr Gly Asn Leu Thr Val Thr
225                 230                 235                 240

Ser Asn Val Val Leu Leu Thr Phe Asp Leu Ser Tyr Ile Thr Pro Ile
                 245                 250                 255

Pro Ser Asp Leu Ala Arg Leu Val Pro Ser Ala Gly Phe Gln Ala Ala
             260                 265                 270

Ser Phe Pro Val Asp Val Ser Phe Thr Arg Asp Ser Ala Thr His Ala
         275                 280                 285

Tyr Gln Ala Tyr Gly Val Tyr Ser Ser Arg Val Phe Thr Ile Thr
     290                 295                 300

Phe Pro Thr Gly Gly
305

<210> SEQ ID NO 13
<211> LENGTH: 309
<212> TYPE: PRT
<213> ORGANISM: artificial
<220> FEATURE:
<223> OTHER INFORMATION: Group 1 isolate Ck- Canada-97594 Td-2013

<400> SEQUENCE: 13

Met Asp Gly Leu Thr Gln Gln Arg Glu Val Val Gly Leu Ile
  1               5                  10                  15

Leu Ser Leu Thr Ser Ser Val Ser

```
                  100                 105                 110
Ser Ile Ala Ser Leu Gln Lys Glu Val Ser Val Leu Ser Gly Glu Ala
            115                 120                 125

Gly Asn Leu Lys Thr Ser Val Ser Ser Gln Gly Leu Thr Ile Thr Ser
        130                 135                 140

Leu Glu Lys Arg Val Glu Ala Leu Glu Gly Ser Ser Met Thr Leu
145                 150                 155                 160

Ser Phe Ala Asp Pro Leu Lys Leu Glu Ala Gly Thr Val Ser Leu Glu
                    165                 170                 175

Val Asp Pro Tyr Phe Cys Ser Val Asn Arg Asn Leu Thr Ser Tyr Ser
                180                 185                 190

Ala Asn Ala Gln Leu Met Gln Phe Gln Trp Ser Val Lys Gly Glu Asp
            195                 200                 205

Gly Ala Ala Asn Ser Ile Asp Met Asp Val Asn Ala His Ser His Gly
        210                 215                 220

Ser Arg Thr Asp Tyr Le

```
                145                 150                 155                 160
Ser Phe Ala Asp Pro Leu Lys Leu Glu Ala Gly Thr Val Ser Leu Glu
                165                 170                 175

Val Asp Pro Tyr Phe Cys Ser Val Asn Arg Asn Leu Thr Ser Tyr Ser
                180                 185                 190

Ala Asn Ala Gln Leu Met Gln Phe Gln Trp Ser Val Lys Gly Glu Asp
                195                 200                 205

Gly Ala Ala Asn Ser Ile Asp Met Asp Val Asn Ala His Ser His Gly
                210                 215                 220

Ser Arg Thr Asp Tyr Leu Met Ser Thr Lys Gln Ser Leu Thr Val Thr
225                 230                 235                 240

Thr Ser Pro Ala Thr Leu Val Phe Glu Leu Asp Arg Ile Ala Ala Leu
                245                 250                 255

Pro Ser Asp Leu Ser Arg Leu Ile Pro Cys Tyr Gly Phe Gln Gln Ala
                260                 265                 270

Thr Phe Pro Val Asp Ile Ser Phe Gln Arg Asp Gly Val Ser His Thr
                275                 280                 285

Tyr Gln Val Tyr Gly Thr Tyr Thr Ser Ser Arg Val Phe Lys Ile Thr
                290                 295                 300

Phe Ser Pro Gly Ser
305

<210> SEQ ID NO 15
<211> LENGTH: 309
<212> TYPE: PRT
<213> ORGANISM: artificial
<220> FEATURE:
<223> OTHER INFORMATION: Group 1 isolate Ck-MS-101021 Td-2013

<400> SEQUENCE: 15

Met Asp Gly Leu Thr Gln Gln Arg Arg Glu Val Val Gly Leu Ile
1               5                   10                  15

Leu Ser Leu Thr Ser Ser Val

```
                195                 200                 205
Gly Ala Ala Asn Ser Ile Asp Met Asp Val Asn Ala His Ser His Gly
            210                 215                 220
Ser Arg Thr Asp Tyr Leu Met Ser Thr Lys Gln Ser Leu Thr Val Thr
225                 230                 235                 240
Thr Ser Pro Ala Thr Leu Val Phe Glu Leu Asp Arg Ile Val Ala Leu
                245                 250                 255
Pro Ser Asp Leu Ser Arg Leu Ile Pro Cys Tyr Gly Phe Gln Gln Ala
            260                 265                 270
Thr Phe Pro Val Asp Ile Ser Phe Gln Arg Asp Gly Val Ser His Thr
        275                 280                 285
Tyr Gln Val Tyr Gly Met Tyr Thr Ser Ser Arg Val Phe Lys Ile Thr
    290                 295                 300
Phe Ser Pro Gly Ser
305

<210> SEQ ID NO 16
<211> LENGTH: 309
<212> TYPE: PRT
<213> ORGANISM: artificial
<220> FEATURE:
<223> OTHER INFORMATION: Group 1 isolate Ck-NC-97361 Td-2013

<400> SEQUENCE: 16

Met Asp Gly Leu Thr Gln Gln Gln Arg Arg Glu Val Val Gly Leu Ile
1               5                   10                  15
Leu Ser Leu Thr Ser Ser Val Ser Thr Ser Ser Gly Asp Leu Thr Gln
            20                  25                  30
Ile Arg Glu Arg Leu Ser Ala Leu Glu Ser Ala Thr Ala Ser Leu Asn
        35                  40                  45
Glu Ser Ile Asn Thr Ala Leu Ser Lys Leu Val Asp Leu Ser Ala Ser
    50                  55                  60
Leu Asp Asn Val Ala Ala Ser Leu Val Glu Thr Lys Val Glu Val Asn
65                  70                  75                  80
Ser Leu Val Ser Asp Val Gln Gly Leu Arg Thr Ser Leu Asp Ser Ser
                85                  90                  95
Ala Ser Glu Leu Ala Ser Leu Ser Ser Leu Val Arg Asp His Gly Ser
            100                 105                 110
Ser Ile Ala Ser Leu Gln Lys Glu Val Ser Val Leu Ser Gly Glu Val
        115                 120                 125
Gly Asn Leu Lys Thr Ser Val Ser Ser Gln Gly Leu Thr Ile Thr Ser
    130                 135                 140
Leu Glu Lys Arg Val Glu Ala Leu Glu Gly Gly Ser Ser Thr Thr Leu
145                 150                 155                 160
Ser Phe Ala Asp Pro Leu Lys Leu Glu Ala Gly Thr Val Ser Leu Glu
                165                 170                 175
Val Asp Pro Tyr Phe Cys Ser Val Asn Arg Asn Leu Thr Ser Tyr Ser
            180                 185                 190
Ala Asn Ala Gln Leu Met Gln Phe Gln Trp Ser Val Lys Gly Glu Asp
        195                 200                 205
Gly Ala Ala Asn Ser Ile Asp Met Asp Val Asn Ala His Ser His Gly
    210                 215                 220
Ser Arg Thr Asp Tyr Leu Met Ser Thr Lys Gln Ser Leu Thr Val Thr
225                 230                 235                 240
Thr Ser Pro Ala Thr Leu Val Phe Glu Leu Asp Arg Ile Val Ala Leu
```

```
                        245                 250                 255
Pro Ser Asp Leu Ser Arg Leu Ile Pro Cys Tyr Gly Phe Gln Gln Ala
            260                 265                 270

Thr Phe Pro Val Asp Ile Ser Phe Gln Arg Asp Gly Val Ser His Thr
        275                 280                 285

Tyr Gln Val Tyr Gly Thr Tyr Thr Ser Ser Arg Val Phe Lys Ile Thr
    290                 295                 300

Phe Ser Pro Gly Ser
305

<210> SEQ ID NO 17
<211> LENGTH: 309
<212> TYPE: PRT
<213> ORGANISM: artificial
<220> FEATURE:
<223> OTHER INFORMATION: Group 1 isolate Ck-SC-101343 Td-2013

<400> SEQUENCE: 17

Met Asp Gly Leu Thr Gln Gln Arg Glu Val Val Gly Leu Ile
1               5                   10                  15

Leu Ser Leu Thr Ser Ser Val Ser Thr Ser Ser Gly Asp Leu Thr Gln
            20                  25                  30

Ile Arg Glu Arg Leu Ser Ala Leu Glu Ser Ala Thr Ala Ser Leu Asn
        35                  40                  45

Glu Ser Ile Asn Thr Ala Leu Ser Lys Leu Val Asp Leu Ser Ala Ser
    50                  55                  60

Leu Asp Asn Val Ala Ala Ser Leu Ala Glu Thr Lys Val Glu Val Asn
65                  70                  75                  80

Ser Leu Val Ser Asp Val Gln Gly Leu Arg Thr Ser Leu Asp Ser Ser
                85                  90                  95

Ala Ser Glu Leu Ala Ser Leu Ser Ser Leu Val Arg Asp His Gly Ser
            100                 105                 110

Ser Ile Ala Ser Leu Gln Lys Glu Val Ser Val Leu Ser Gly Glu Val
        115                 120                 125

Gly Asn Leu Lys Thr Ser Val Ser Ser Gln Gly Leu Thr Ile Thr Ser
    130                 135                 140

Leu Glu Lys Arg Val Glu Ala Leu Glu Gly Gly Ser Ser Thr Thr Leu
145                 150                 155                 160

Ser Phe Ala Asp Pro Leu Lys Leu Glu Ala Gly Thr Val Ser Leu Glu
                165                 170                 175

Val Asp Pro Tyr Phe Cys Ser Val Asn Arg Asn Leu Thr Ser Tyr Ser
            180                 185                 190

Ala Asn Ala Gln Leu Met Gln Phe Gln Trp Ser Val Lys Gly Glu Asp
        195                 200                 205

Gly Ala Ala Asn Ser Ile Asp Met Asp Val Asn Ala His Ser His Gly
    210                 215                 220

Ser Arg Thr Asp Tyr Leu Met Ser Thr Lys Gln Ser Leu Thr Val Thr
225                 230                 235                 240

Thr Ser Pro Ala Thr Leu Val Phe Glu Leu Asp Arg Ile Val Ala Leu
                245                 250                 255

Pro Ser Asp Leu 290                 295                 300

Phe Ser Pro Gly Ser
305

<210> SEQ ID NO 18
<211> LENGTH: 309
<212> TYPE: PRT
<213> ORGANISM: artificial
<220> FEATURE:
<223> OTHER INFORMATION: Group 1 isolate Ck-TN-101279 Td-2013

<400> SEQUENCE: 18

Met Asp Gly Leu Thr Gln Gln Arg Arg Glu Val Val Gly Leu Ile
1               5                   10                  15

Leu Ser Leu Thr Ser

<213> ORGANISM: artificial
<220> FEATURE:
<223> OTHER INFORMATION: Group 1 isolate Ck-TX-100970 Td-2013

<400> SEQUENCE: 19

Met Asp Gly Leu Thr Gln Gln Gln Arg Arg Glu Val Val Gly Leu Ile
1               5                   10                  15

Leu Ser Leu Thr Ser Ser Ala Ser Thr Ser Ala Gly Asp Leu Thr Gln
                20                  25                  30

Ile Arg Glu Arg Leu Ser Ala Leu Glu Ser Ala Thr Ala Ser Leu Asn
            35                  40                  45

Glu Ser Ile Asn Thr Ala Leu Ser Lys Leu Val Asp Leu Ser Ala Ser
50                  55                  60

Leu Asp Asn Val Ala Ala Ser Leu Ala Glu Thr Lys Val Glu Val Asn
65                  70                  75                  80

Ser Leu Val Ser Asp Val Gln Gly Leu Arg Thr Ser Leu Asp Ser Ser
                85                  90                  95

Ala Ser Glu Leu Ala Ser Leu Ser Ser Leu Val Arg Asp His Gly Ser
            100                 105                 110

Ser Ile Ala Ser Leu Gln Lys Glu Val Ser Val Leu Ser Gly Glu Val
        115                 120                 125

Gly Asn Leu Lys Thr Ser Val Ser Ser Gln Gly Leu Thr Ile Thr Ser
130                 135                 140

Leu Glu Lys Leu Val Glu Ala Leu Gly Gly Ser Ser Thr Thr Leu
145                 150                 155                 160

Ser Phe Ala Asp Pro Leu Lys Leu Glu Ala Gly Thr Val Ser Leu Glu
                165                 170                 175

Val Asp Pro Tyr Phe Cys Ser Val Asn Arg Asn Leu Thr Ser Tyr Ser
            180                 185                 190

Ala Asn Ala Gln Leu Met Gln Phe Gln Trp Ser Val Lys Gly Glu Asp
        195                 200                 205

Gly Ala Ala Asn Ser Ile Asp Met Asp Val Asn Ala His Ser His Gly
210                 215                 220

Ser Arg Thr Asp Tyr Leu Met Ser Thr Lys Gln Ser Phe Thr Val Thr
225                 230                 235                 240

Thr Ser Pro Ala Thr Leu Val Phe Glu Leu Asp Arg Ile Val Ala Leu
                245                 250                 255

Pro Ser Asp Leu Ser Arg Leu Ile Pro Cys Tyr Gly Phe Gln Gln Ala
            260                 265                 270

Thr Phe Pro Val Asp Ile Ser Phe Gln Arg Asp Gly Val Ser His Thr
        275                 280                 285

Tyr Gln Val Tyr Gly Thr Tyr Thr Ser Ser Arg Val Phe Lys Ile Thr
    290                 295                 300

Phe Ser Pro Gly Ser
305

<210> SEQ ID NO 20
<211> LENGTH: 309
<212> TYPE: PRT
<213> ORGANISM: artificial
<220> FEATURE:
<223> OTHER INFORMATION: Group 1 isolate Ck-AR-100557 Td-2013

<400> SEQUENCE: 20

Met Asp Gly Leu Thr Gln Gln Gln Arg Arg Glu Val Val Gly Leu Ile
1               5                   10                  15

Leu Ser Leu Thr Ser Ser Ala Ser Thr Ser Ser Gly Asp Leu Thr Gln
            20                  25                  30

Ile Arg Glu Arg Leu Ser Ala Leu Glu Ser Ala Thr Ala Ser Leu Asn
            35                  40                  45

Glu Ser Ile Asn Thr Ala Leu Ser Lys Leu Val Asp Leu Ser Ala Ser
 50                  55                  60

Leu Asp Asn Val Ala Ala Ser Leu Ala Glu Thr Lys Val Glu Val Asn
 65                  70                  75                  80

Ser Leu Val Ser Asp Val Gln Gly Leu Arg Thr Ser Leu Asp Ser Ser
                85                  90                  95

Ala Ser Glu Leu Ala Ser Leu Ser Leu Val Arg Asp His Gly Ser
            100                 105                 110

Ser Ile Ala Ser Leu Gln Lys Glu Val Ser Val Leu Ser Gly Glu Val
            115                 120                 125

Gly Asn Leu Lys Thr Ser Val Ser Ser Gln Gly Leu Thr Ile Thr Ser
            130                 135                 140

Leu Glu Lys Arg Val Glu Ala Leu Glu Gly Gly Ser Ser Thr Thr Leu
145                 150                 155                 160

Ser Phe Ala Asp Pro Leu Lys Leu Glu Ala Gly Thr Val Ser Leu Glu
                165                 170                 175

Val Asp Pro Tyr Phe Cys Ser Val Asn Arg Asn Leu Thr Ser Tyr Ser
                180                 185                 190

Ala Asn Ala Gln Leu Met Gln Phe Gln Trp Ser Val Lys Gly Glu Asp
            195                 200                 205

Gly Ala Ala Asn Ser Ile Asp Met Asp Val Asn Ala His Ser His Gly
210                 215                 220

Ser Arg Thr Asp Tyr Leu Met Ser Thr Lys Gln Ser Leu Thr Val Thr
225                 230                 235                 240

Thr Ser Pro Ala Thr Leu Val Phe Glu Leu Asp Arg Ile Val Ala Leu
                245                 250                 255

Pro Ser Asp Leu Ser Arg Leu Ile Pro Cys Tyr Gly Phe Gln Gln Ala
            260                 265                 270

Thr Phe Pro Val Asp Ile Ser Phe Gln Arg Asp Gly Val Ser His Thr
            275                 280                 285

Tyr Gln Val Tyr Gly Thr Tyr Thr Ser Ser Arg Val Phe Lys Ile Thr
            290                 295                 300

Phe Ser Pro Gly Ser
305

<210> SEQ ID NO 21
<211> LENGTH: 309
<212> TYPE: PRT
<213> ORGANISM: artificial
<220> FEATURE:
<223> OTHER INFORMATION: Group 2 isolate Ck-AR-100558 Td-2013

<400> SEQUENCE: 21

Met Ala Gly Leu Ser Pro Ser Gln Arg Arg Glu Val Val Ser Leu Ile
1               5                   10                  15

Leu Ser Leu Thr Ser Asn Ala Thr Ile Asn Pro Gly Asp Leu Thr Ser
            20                  25                  30

Ile Arg Glu Arg Leu Thr Ser Leu Glu Val Ser Thr Glu Ser Leu Tyr
            35                  40                  45

Arg Ser Ile Ser Ser Val Ser Asn Ala Val Ser Asp Ile Ser Ala Asp
 50                  55                  60

```
Leu Gln Asn Val Thr Arg Ala Leu Asp Asp Val Thr Ala Asn Leu Asn
 65                  70                  75                  80

Gly Met Arg Val Thr Ile Thr Thr Leu His Asp Ser Val Ser Thr Leu
                 85                  90                  95

Ser Thr Thr Val Thr Asp Leu Ser Gly Thr Ser Ser Ala His Ser Glu
            100                 105                 110

Ala Leu Ser Ser Leu Arg Thr Thr Val Asn Gly Asn Ser Thr Ile Ile
        115                 120                 125

Glu Asn Leu Lys Ser Asp Val Ser Ser Asn Gly Leu Ala Ile Thr Asp
    130                 135                 140

Leu Gln Ser Arg Val Lys Ser Leu Glu Ser Thr Ser Ser Ser Gly Leu
145                 150                 155                 160

Ser Phe Ser Pro Pro Leu Ser Ile Ala Asp Gly Val Val Ser Leu Asn
                165                 170                 175

Met Asp Pro Tyr Phe Cys Ser Gln Arg Val Ser Leu Thr Ser Tyr Ser
            180                 185                 190

Ala Glu Ala Gln Leu Met Arg Phe Gln Trp Met Ala Arg Gly Thr Asn
        195                 200                 205

Gly Ser Ser Asp Asn Ile Asp Met Asn Val Asn Ala His Cys His Gly
    210                 215                 220

Arg Arg Thr Asp Tyr Ile Met Ser Ser Thr Gly Gly Leu Thr Val Thr
225                 230                 235                 240

His Asn Ala Val Ser Leu Thr Phe Asp Leu Ser Tyr Ile Thr Ser Leu
                245                 250                 255

Pro Ser Asp Leu Ser Arg Leu Ile Pro Asn Ala Gly Phe Gln Val Ala
            260                 265                 270

Ser Phe Pro Val Asp Val Ser Phe Thr Arg Asp Ser Thr Thr His Ala
        275                 280                 285

Tyr Gln Ala Tyr Gly Ile Tyr Ser Ser Ser Arg Ala Phe Thr Ile Thr
    290                 295                 300

Phe Pro Thr Gly Gly
305

<210> SEQ ID NO 22
<211> LENGTH: 309
<212> TYPE: PRT
<213> ORGANISM: artificial
<220> FEATURE:
<223> OTHER INFORMATION: Group 2 isolate Ck-GA-98175 Td-2013

<400> SEQUENCE: 22

Met Ala Gly Leu Ser Pro Ser Gln Arg Arg Glu Val Val Ser Leu Ile
  1               5                  10                  15

Leu Ser Leu Thr Ser Asn Ala Thr Ile Ser Pro Gly Asp Leu Thr Thr
                 20                  25                  30

Ile His Glu Arg Leu Thr Ser Leu Glu Ala Ser Thr Glu Ser Leu Tyr
             35                  40                  45

Arg Ser Ile Ser Ser Met Ser Val Thr Val Ser Asp Val Ser Thr Asp
 50                  55                  60

Leu Gln Asn Val Thr Arg Ala Leu Asp Asp Val Ile Thr Asn Leu Asn
 65                  70                  75                  80

Gly Met Arg Ala Thr Ile Thr Ala Leu Gln Asp Ser Val Ser Thr Leu
                 85                  90                  95

Ser Thr Thr Val Thr Asp Leu Ser Thr Ser Ser Ala His Ser Glu
            100                 105                 110
```

-continued

```
Thr Leu Ser Ser Leu Arg Asn Thr Val Asn Gly Asn Ser Thr Thr Ile
            115                 120                 125
Gly Asn Leu Lys Ser Asp Val Ser Ser Asn Gly Leu Ala Ile Thr Asp
130                 135                 140
Leu Gln Ser Arg Val Lys Ser Leu Glu Ser Thr Ser Ser His Gly Leu
145                 150                 155                 160
Ser Phe Ser Pro Pro Leu Ser Val Ala Asp Gly Val Val Ser Leu Asn
                165                 170                 175
Val Asp Pro Tyr Phe Cys Ser Gln Arg Val Ser Leu Thr Ser Tyr Ser
            180                 185                 190
Ala Glu Ala Gln Leu Met Gln Phe Gln Trp Met Ala Arg Gly Ser Asn
        195                 200                 205
Gly Ser Ser Asp Asn Ile Asp Met Asn Val Asn Ala His Cys His Gly
    210                 215                 220
Arg Arg Thr Asp Tyr Ile Met Ser Ser Thr Gly Gly Leu Thr Val Thr
225                 230                 235                 240
Arg Asn Ala Val Ser Leu Thr Phe Asp Leu Ser Tyr Ile Thr Lys Leu
                245                 250                 255
Pro Ser Asp Leu Ser Arg Leu Ile Pro Ser Ala Gly Phe Gln Ala Ala
            260                 265                 270
Ser Phe Pro Ala Asp Val Ser Phe Thr Arg Asp Ser Thr Thr His Ala
        275                 280                 285
Tyr Gln Ala Tyr Gly Val Tyr Ser Ser Ser Arg Val Phe Thr Ile Thr
    290                 295                 300
Phe Pro Thr Gly Gly
305

<210> SEQ ID NO 23
<211> LENGTH: 309
<212> TYPE: PRT
<213> ORGANISM: artificial
<220> FEATURE:
<223> OTHER INFORMATION: Group 2 isolate Ck-MO-101582 Td-2013

<400> SEQUENCE: 23

Met Ala Gly Leu Ser Pro Ser Gln Arg Arg Glu Val Val Ser Leu Ile
1               5                   10                  15
Leu Ser Leu Thr Ser Asn

```
Ser Phe Ser Pro Pro Leu Ser Val Ala Asp Gly Ile Val Ser Leu Asn
                165                 170                 175

Met Asp Pro Tyr Phe Cys Ser Gln Arg Val Ser Leu Thr Ser Tyr Ser
            180                 185                 190

Ala Glu Ala Gln Leu Met Gln Phe Gln Trp Met Ala Arg Gly Ser Asn
        195                 200                 205

Gly Ser Ser Asp Asn Ile Asp Met Asn Val Asn Ala His Cys His Gly
    210                 215                 220

Arg Arg Thr Asp Tyr Ile Met Ser Ser Thr Gly Gly Leu Thr Val Thr
225                 230                 235                 240

Arg Asn Ala Val Ser Leu Thr Phe Asp Leu Ser Tyr Ile Thr Lys Leu
                245                 250                 255

Pro Ser Asp Leu Ser Arg Leu Ile Pro Ser Ala Gly Phe Gln Ala Ala
            260                 265                 270

Ser Phe Pro Ala Asp Val Ser Phe Thr Arg Asp Ser Thr Thr His Ala
        275                 280                 285

Tyr Gln Ala Tyr Gly Val Tyr Ser Ser Ser Arg Val Phe Thr Ile Thr
    290                 295                 300

Phe Pro Thr Gly Gly
305

<210> SEQ ID NO 24
<211> LENGTH: 309
<212> TYPE: PRT
<213> ORGANISM: artificial
<220> FEATURE:
<223> OTHER INFORMATION: Group 2 isolate Ck-AL-95524 Td-2012

<400> SEQUENCE: 24

Met Ala Gly Leu Ser Pro Ser Gln Arg Arg Glu Val Val Ser Leu Ile
1               5                   10                  15

Leu Ser Leu Thr Ser Asn Ala Thr Ile Asn Pro Gly Asp Leu Thr Ser
                20                  25                  30

Ile Arg Glu Arg Leu Thr Ser Leu Glu Val Ser Thr Glu Ser Leu Tyr
            35                  40                  45

Arg Ser Ile Ser Ser Val Ser Asn Ala Val Ser Asp Ile Ser Ala Asp
50                  55                  60

Leu Gln Asn Val Thr Arg Ala Leu Asp Asp Val Thr Ala Asn Leu Asn
65                  70                  75                  80

Gly Met Arg Val Thr Ile Thr Thr Leu His Asp Ser Val Ser Thr Leu
                85                  90                  95

Ser Thr Thr Val Thr Asp Leu Ser Thr Ser Ser Ala His Ser Glu
            100                 105                 110

Ala Leu Ser Ser Leu Arg Thr Thr Val Asn Gly Asn Ser Thr Ile Ile
        115                 120                 125

Glu Asn Leu Lys Ser Asp Val Ser Ser Asn Gly Leu Ala Ile Thr Asp
    130                 135                 140

Leu Gln Ser Arg Val Lys Ser Leu Glu Ser Thr Ser Ser Ser Gly Leu
145                 150                 155                 160

Ser Phe Ser Pro Pro Leu Ser Val Ala Asp Gly Val Val Ser Leu Asn
                165                 170                 175

Met Asp Pro Tyr Phe Cys Ser Gln Arg Val Ser Leu Thr Ser Tyr Ser
            180                 185                 190

Ala Glu Ala Gln Leu Met Arg Phe Gln Trp Met Ala Arg Gly Thr Asn
        195                 200                 205
```

-continued

```
Gly Ser Ser Asp Asn Ile Asp Met Asn Val Asn Ala His Cys His Gly
    210             215                 220
Arg Arg Thr Asp Tyr Ile Met Ser Ser Thr Gly Gly Leu Thr Val Thr
225             230             235                         240
His Asn Ala Val Ser Leu Thr Phe Asp Leu Ser Tyr Ile Thr Ser Leu
                245             250                 255
Pro Ser Asp Leu Ser Arg Leu Ile Pro Asn Ala Gly Phe Gln Val Ala
            260             265                 270
Ser Phe Pro Val Asp Val Ser Phe Thr Arg Asp Ser Thr Thr His Ala
        275             280                 285
Tyr Gln Ala Tyr Gly Ile Tyr Ser Ser Ser Arg Ala Phe Thr Ile Thr
    290             295                 300
Phe Pro Thr Gly Gly
305
```